United States Patent
Passaniti et al.

(10) Patent No.: US 10,329,246 B2
(45) Date of Patent: Jun. 25, 2019

(54) RUNX2 TRANSCRIPTION FACTOR INHIBITORS AND USES THEREOF

(71) Applicants: University of Maryland, Baltimore, Baltimore, MD (US); The United States of America as Represented by the Department of Veterans Affairs, Washington, DC (US)

(72) Inventors: Antonino Passaniti, White Hall, MD (US); MacKerell D. Alexander, Jr., Baltimore, MD (US)

(73) Assignees: University of Maryland, Baltimore, Baltimore, MD (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/708,872

(22) Filed: Sep. 19, 2017

(65) Prior Publication Data

US 2018/0086696 A1  Mar. 29, 2018

Related U.S. Application Data

(63) Continuation-in-part of application No. PCT/US2016/023257, filed on Mar. 18, 2016.

(60) Provisional application No. 62/135,224, filed on Mar. 19, 2015.

(51) Int. Cl.
| | |
|---|---|
| A61K 31/196 | (2006.01) |
| C07C 235/82 | (2006.01) |
| A61K 31/517 | (2006.01) |
| A61P 35/00 | (2006.01) |
| A61K 31/19 | (2006.01) |
| A61K 45/06 | (2006.01) |

(52) U.S. Cl.
CPC ............ *C07C 235/82* (2013.01); *A61K 31/19* (2013.01); *A61K 31/196* (2013.01); *A61K 31/517* (2013.01); *A61K 45/06* (2013.01); *A61P 35/00* (2018.01); *C07C 2601/14* (2017.05); *C07C 2602/42* (2017.05); *C07C 2603/94* (2017.05)

(58) Field of Classification Search
CPC ... A61K 31/19; A61K 31/196; A61K 2300/00
See application file for complete search history.

(56) References Cited

U.S. PATENT DOCUMENTS

2014/0256684 A1   9/2014 Beard et al.

FOREIGN PATENT DOCUMENTS

| WO | 2011006158 A2 | 1/2011 | | |
|---|---|---|---|---|
| WO | 2011163502 A1 | 12/2011 | | |
| WO | WO 2011/163502 A1 * | 12/2011 | ........... | A61K 31/167 |
| WO | 2014110476 A2 | 7/2014 | | |

OTHER PUBLICATIONS

Sancisi; American Association of cancer research; Mar. 13, 2015.*
Brusgard J. A Role for RUNX2 and TAZ in Promoting a Tumorigenic Phenotype in Luminal Breast Cancer Cells, Ph. D. Dissertation, Dec. 2014, University of Maryland, Baltimore, Molecular Medicine p. 1-127 (relevant pp. 1, 43, 44, 51, 55-58, 74, 80).
van Pel DM, Barrett IJ, Shimizu Y, Sajesh BV, Guppy BJ, Pfeifer T, McManus KJ, Hieter P. An Evolutionarily Conserved Synthetic Lethal Interaction Network Identifies FEN1 as a Broad-Spectrum Target for Anticancer Therapeutic Development, PLOS Genetics, 2013; 9(1), e1003254:1-11.
Brusgard JL, Choe M, Chumsri S, Renoud K, MacKerell Jr AD, Sudol M, Passaniti A. RUNX2 and TAZ-dependent signaling pathways regulate soluble E-Cadherin levels and tumorsphere formation in breast cancer cells Oncotarget. 2015; 6(29):28132-50. doi: 10.18632/oncotarget.4654.
Kuefer R, Hofer MD, Zorn CS, Engel O, Volkmer BG, Juarez-Brito MA, Eggel M, Gschwend JE, Rubin MA, Day ML., Assessment of a fragment of e-cadherin as a serum biomarker with predictive value for prostate cancer. Br J Cancer 2005; 92:2018-2023.
Cadoo KA, Fornier MN, Morris PG., Biological subtypes of breast cancer: current concepts and implications for recurrence patterns. Q J Nucl Med Mol Imaging 2013; 57:312-321.

(Continued)

*Primary Examiner* — Pancham Bakshi
(74) *Attorney, Agent, or Firm* — Benjamin Aaron Adler

(57) ABSTRACT

Provide herein are compounds with a general chemical structure of:

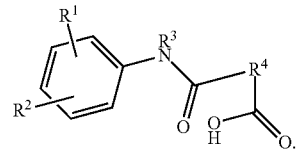

Substituents $R_1$ and $R_2$ independently are H, Cl, F, Br, $CH_3$, $CF_3$, SH, —N($C_{1-3}$alkyl)$_2$, —NHC(O)$C_{1-3}$alkyl, or —NHC(O)$C_{5-7}$cycloalkyl, substituent $R_3$ is H or $C_{1-3}$ alkyl and R4 is a bridged cycloalkene such as a bridged cyclohexene or a bridge-substituted cyclohexene. The compounds are therapeutics to treat a cancer, such as breast cancer, or metastatic cancers, to inhibit RUNX2 activity, such as protein expression, in a cancer cell and to increase survival of a subject with breast cancer.

22 Claims, 39 Drawing Sheets

Specification includes a Sequence Listing.

(56) References Cited

OTHER PUBLICATIONS

Siegel R, Naishadham D, Jemal A., Cancer statistics, 2013. CA Cancer J Clin 2013; 63:11-30.

Foley J, Nickerson NK, Nam S, Allen KT, Gilmore JL, Nephew KP, Riese DJ, EGFR signaling in breast cancer: bad to the bone. Semin Cell Dev Biol 2010; 21:951-960.

Ganapathy V, Banach-Petrosky W, Xie W, Kareddula A, Nienhuis H, Miles G, Reiss M., Luminal breast cancer metastasis is dependent on estrogen signaling. Clin Exp Metastasis 2012; 29: 493-509.

Ithimakin S, Day KC, Malik F, Zen Q, Dawsey SJ, Bersano-Begey TF, Quraishi AA, Ignatoski KW, Daignault S, Davis A, Hall CL, Palanisamy N, Heath AN, Tawakkol N, Luther TK, Clouthier SG, Chadwick WA, Day ML, Kleer CG, Thomas DG, Hayes DF, Korkaya H, Wicha MS., HER2 drives luminal breast cancer stem cells in the absence of HER2 amplification: implications for efficacy of adjuvant trastuzumab. Cancer Res 2013; 73:1635-1646.

Brouxhon SM, Kyrkanides S, Teng X, O'Banion MK, Clarke R, Byers S, Ma L., Soluble-E-cadherin activates HER and IAP family members in HER2+ and TNBC human breast cancers. Mol Carcinog 2013, 53(11): 893-906.

McDonald L1, Ferrari N, Terry A, Bell M, Mohammed ZM, Orange C, Jenkins A, Muller WJ, Gusterson BA, Neil JC, Edwards J, Morris JS, Cameron ER, Blyth K.., RUNX2 correlates with subtype-specific breast cancer in a human tissue microarray, and ectopic expression of Runx2 perturbs differentiation in the mouse mammary gland. Dis Model Mech 2014, 7(5): 525-534.

Das K, Leong DT, Gupta A, Shen L, Putti T, Stein GS, van Wijnen AJ, Salto-Tellez M., Positive association between nuclear Runx2 and oestrogen-progesterone receptor gene expression characterises a biological subtype of breast cancer. Eur J Cancer 2009; 45:2239-2248.

Onodera Y, Miki Y, Suzuki T, Takagi K, Akahira J, Sakyu T, Watanabe M, Inoue S, Ishida T, Ohuchi N, Sasano H., Runx2 in human breast carcinoma: its potential roles in cancer progression. Cancer Sci 2010; 101:2670-2675.

Barnes GL, Hebert KE, Kamal M, Javed A, Einhorn TA, Lian JB, Stein GS, Gerstenfeld LC., Fidelity of Runx2 activity in breast cancer cells is required for the generation of metastases-associated osteolytic disease. Cancer Res 2004; 64:4506-4513.

Pratap J, Javed A, Languino LR, van Wijnen AJ, Stein JL, Stein GS, Lian JB., The Runx2 osteogenic transcription factor regulates matrix metalloproteinase 9 in bone metastatic cancer cells and controls cell invasion. Mol Cell Biol 2005; 25:8581-8591.

Yagi R, Chen LF, Shigesada K, Murakami Y, Ito Y., A WW domain-containing yes-associated protein (YAP) is a novel ranscriptional co-activator. Embo J 1999; 18:2551-2562.

Cui CB, Cooper LF, Yang X, Karsenty G, Aukhil I., Transcriptional coactivation of bone-specific transcription factor Cbfa1 by TAZ. Mol Cell Biol 2003; 23:1004-1013.

Vitolo MI, Anglin IE, Mahoney WM Jr, Renoud KJ, Gartenhaus RB, Bachman KE, Passaniti A., The RUNX2 transcription factor cooperates with the YES-associated protein, YAP65, to promote cell transformation. Cancer Biol Ther 2007; 6:856-863.

Brouxhon SM, Kyrkanides S, Teng X, Raja V, O'Banion MK, Clarke R, Byers S, Silberfeld A, Tornos C, Ma L., Monoclonal antibody against the ectodomain of E-cadherin (DECMA-1) suppresses breast carcinogenesis: involvement of the HER/PI3K/Akt/mTOR and IAP pathways. Clin Cancer Res 2013; 19:3234-3246.

Cordenonsi M, Zanconato F, Azzolin L, Forcato M, Rosato A, Frasson C, Inui M, Montagner M, Parenti AR, Poletti A, Daidone MG, Dupont S, Basso G, Bicciato S, Piccolo S., The Hippo transducer TAZ confers cancer stem cell-related traits on breast cancer cells. Cell 2011; 147:759-772.

Hiemer SE, Szymaniak AD, Varelas X., The transcriptional regulators TAZ and YAP direct transforming growth factor 3-induced tumorigenic phenotypes in breast cancer cells. J Biol Chem 2014; 289: 13461-13474.

Kim J, Villadsen R, Sørlie T, Fogh L, Grønlund SZ, Fridriksdottir AJ, Kuhn I, Rank F, Wielenga VT, Solvang H, Edwards PA, Børresen-Dale AL, Rønnov-Jessen L., Bissell MJ, Petersen OW., Tumor initiating but differentiated luminal-like breast cancer cells are highly invasive in the absence of basal-like activity. Proc Natl Acad Sci U S A 2012; 109:6124-6129.

Liu C, Huang W, Lei Q., Regulation and function of the TAZ transcription co-activator. Int J Biochem Mol Biol 2011; 2:247-256.

Chan SW, Lim CJ, Guo K, Ng CP, Lee I, Hunziker W, Zeng Q, Hong W., A role for TAZ in migration, invasion, and tumorigenesis of breast cancer cells. Cancer Res 2008; 68:2592-2598.

Lei QY, Zhang H, Zhao B, Zha ZY, Bai F, Pei XH, Zhao S, Xiong Y, Guan KL., TAZ promotes cell proliferation and epithelial-mesenchymal transition and is inhibited by the hippo pathway. Mol Cell Biol 2008; 28:2426-2436.

Matteucci E, Maroni P, Luzzati A, Perrucchini G, Bendinelli P, Desiderio MA.., Bone metastatic process of breast cancer involves methylation state affecting E-cadherin expression through TAZ and WWOX nuclear effectors. Eur J Cancer 2013; 49:231-244.

Lee JM, Dedhar S, Kalluri R, Thompson EW., The epithelial-mesenchymal transition: new insights in signaling, development, and disease. J Cell Biol 2006; 172:973-981.

Thiery JP, Acloque H, Huang RY, Nieto MA., Epithelial-mesenchymal transitions in development and disease. Cell 2009; 139:871-890.

Valastyan S, Weinberg RA, Tumor metastasis: molecular insights and evolving paradigms. Cell 2011; 147: 275-292.

Najy AJ, Day KC, Day ML., The ectodomain shedding of E-cadherin by ADAM15 supports ErbB receptor activation. J Biol Chem 2008; 283:18393-18401.

David JM, Rajasekaran AK., Dishonorable discharge: the oncogenic roles of cleaved E-cadherin fragments.Cancer Res 2012; 72:2917-2923.

Grabowska MM, Day ML., Soluble E-cadherin: more than a symptom of disease. Front Biosci (Landmark Ed) 2012; 17:1948-1964.

Kuefer R, Hofer MD, Gschwend JE, Pienta KJ, Sanda MG, Chinnaiyan AM, Rubin MA, Day ML, The role of an 80 kDa fragment of E-cadherin in the metastatic progression of prostate cancer. Clin Cancer Res 2003; 9:6447-6452.

\* cited by examiner compound 1 compound 2 compound 3 compound 4 compound 5 compound 6 compound 7 compound 8 compound 9 compound 10 compound 11

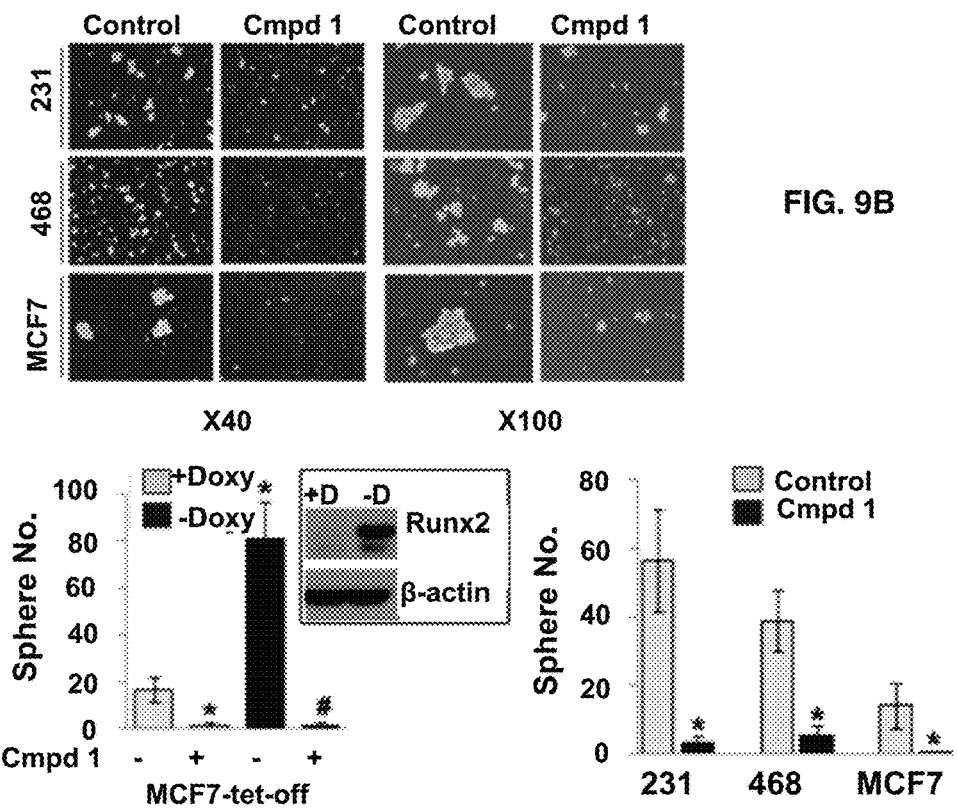
FIG. 9B
FIG. 9C
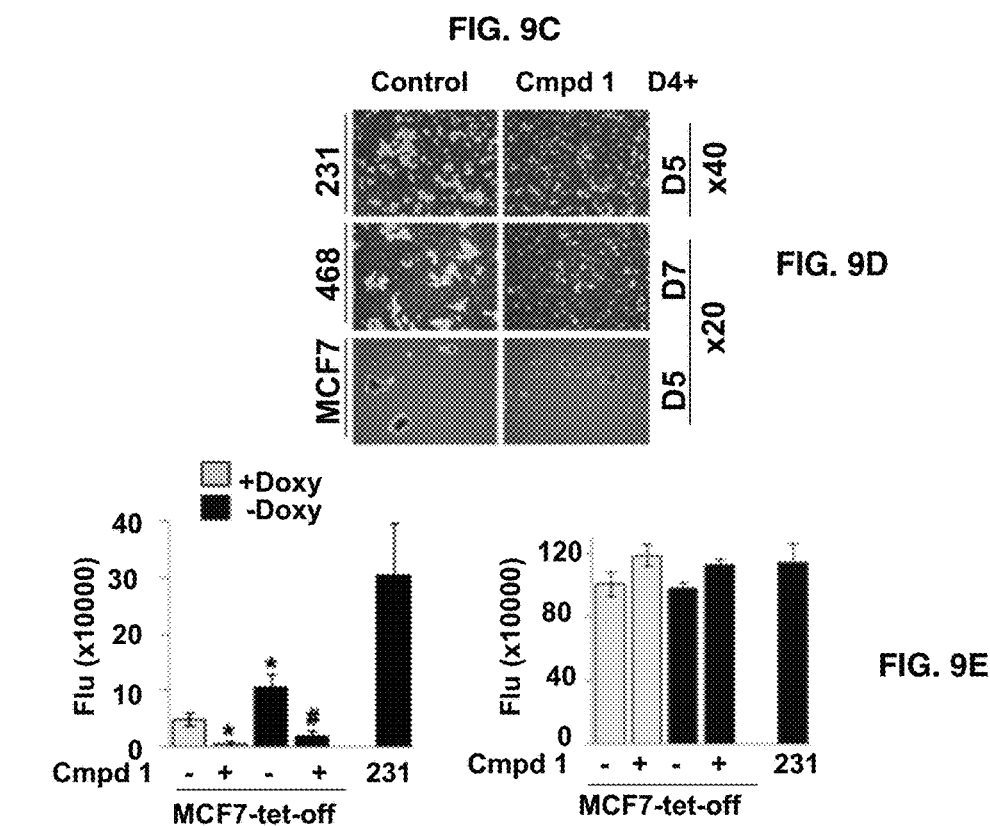
FIG. 9D
FIG. 9E

FIG. 14E            FIG. 14F

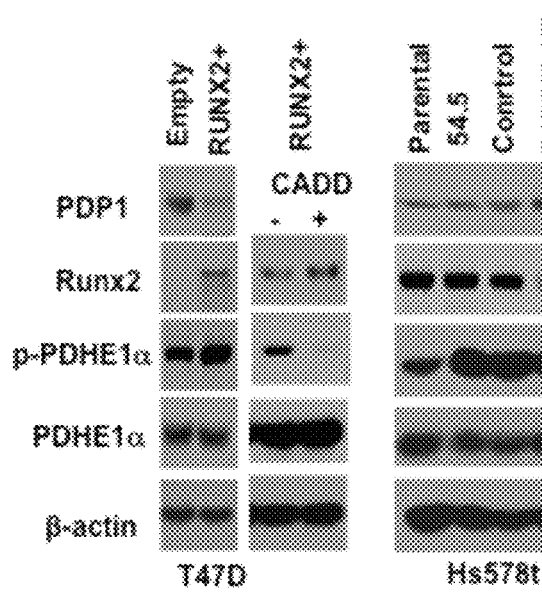
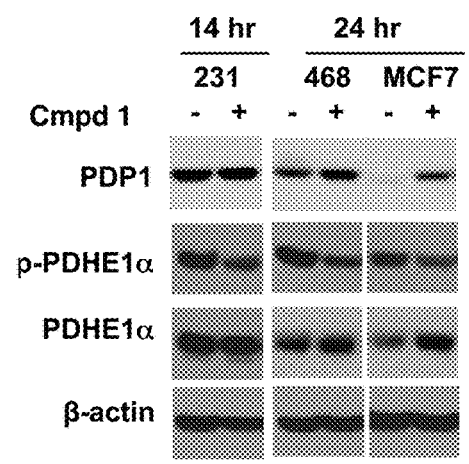
FIG. 25A
FIG. 25B
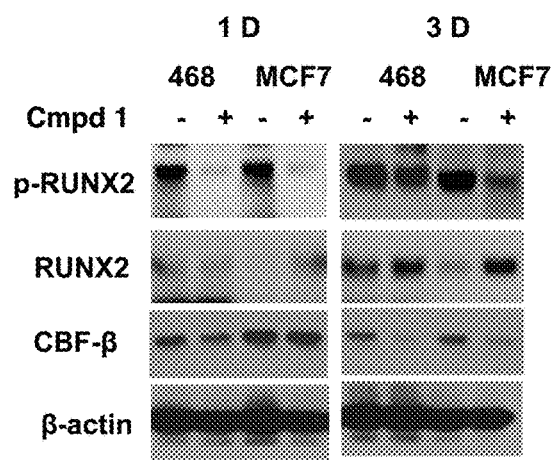
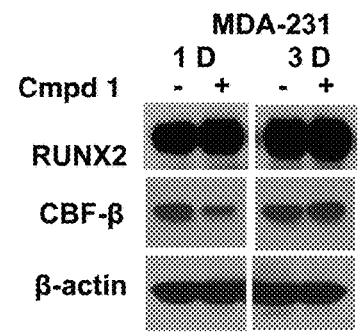
FIG. 25C
FIG. 25D

RUNX2 TRANSCRIPTION FACTOR INHIBITORS AND USES THEREOF

CROSS-REFERENCE TO RELATED APPLICATIONS

This application is a continuation-in-part under 35 U.S.C. § 120 of international application PCT/US2016/023257, filed Mar. 18, 2016, which claims benefit of priority under 37 C.F.R. § 1.119(e) of provisional application U.S. Ser. No. 62/135,224, filed Mar. 19, 2015, the entirety of both of which are hereby incorporated by reference.

FEDERAL FUNDING LEGEND

This invention was made with government support under Grant Number CA108846 awarded by the National Institutes of Health. The government has certain rights in the invention.

BACKGROUND OF THE INVENTION

Field of the Invention

The present invention relates to RUNX2 transcription factor inhibitors and their uses in cancer treatment. More specifically, the invention relates to derivatives and analogs of the RUNX2 transcription factor inhibitor compound 1 and their uses in treating breast cancer.

Description of the Related Art

Breast cancer is a heterogeneous disease and despite advances in treatment, it remains the second leading cause of cancer-related deaths among women. Luminal breast cancer has the highest rates of relapse, often localizes to the bone, and accounts for 50% of all metastatic-related breast cancer deaths in spite of the primary tumor being highly responsive to treatment. Given their high rate of relapse, it is clear current treatment modalities are insufficient to completely eradicate these heterogeneous tumors.

The HER2-targeted agent trastuzumab is the only FDA-approved for use in patients whose tumors are clinically defined as HER2 amplified. Early clinical trials have shown a 50% reduction in recurrence rates in patients with luminal breast cancer treated with combination trastuzumab/chemotherapy over patients treated with chemotherapy alone. Ductal carcinomas in situ (DCIS) also express HER2 prior to a transition to an invasive phenotype, suggesting there may be clinical benefit to treating early disease with HER2-targeted agents even in the absence of HER2 amplification.

RUNX2, an osteoblast transcription factor, is expressed in developing breast epithelial cells and is enriched in the mammary stem cell population responsible for terminal end bud differentiation. RUNX2 is expressed in early stage ER+ breast cancer above normal levels found in the breast epithelia. In basal-type breast cancer cell lines RUNX2 promotes an osteomimetic phenotype and metastasis to the bone through transcriptional activation of osteopontin, MMPs, and VEGF. The RUNX2 binding partners, YAP and TAZ are WW domain-containing transcriptional coactivators that promote cell transformation, osteogenesis, or stem cell self-renewal.

TAZ is a nuclear effector of the Hippo tumor suppressor pathway that has been implicated in promoting breast cancer progression. RUNX2 was recently shown to be upregulated in a subpopulation of luminal A MCF7 cells that share molecular characteristics with a more invasive breast cancer phenotype, including genes associated with stem cell renewal, and enhanced tumorsphere-forming capacity. Disruption of cell:cell contacts (Hippo pathway inactivation) results in reduced phosphorylation of TAZ leading to nuclear translocation and interaction with transcription factors that regulate expression of cell proliferation and anti-apoptotic genes. TAZ is upregulated in 20% of breast cancer patients and is expressed in many breast cancer cell lines where it has been shown to increase migration, invasion, tumorigenesis, drug resistance, and to promote an EMT. TAZ and RUNX2 have both been independently implicated in mediating metastasis to the bone but a cooperative role in breast cancer has not been reported.

Although an epithelial-mesenchymal transition (EMT) in breast cancer is characterized by downregulation of E-Cadherin, it is becoming increasingly clear that cells may also disseminate from the primary tumor without undergoing an EMT or downregulating E-Cadherin expression. An alternative pathway involving secretion of an oncogenic E-Cadherin ectodomain (sE-Cad; 80 kDa) was reported to mediate migration, invasion, and proliferation while maintaining epithelial morphology. sE-Cad functions in an autocrine and paracrine manner to activate survival and metastatic programs by interacting with ErbB receptors. In addition, sE-Cad binds full length E-Cadherin resulting in the destabilization of adherens junctions. sE-Cad has been proposed as a functional metastatic biomarker in many cancers including, but not limited to, breast cancer. RUNX2 expression in luminal breast cancer cells results in nuclear TAZ localization and expression of sE-Cad. TGFβ enhances the RUNX2-mediated expression of sE-Cad and upregulation of HER2 in MCF7 cells. RUNX2 associated with TAZ immune complexes and knockdown of TAZ inhibited RUNX2 and HER2 mediated tumorsphere formation.

Thus, there is a recognized need in the art for inhibitors of RUNX2 as cancer therapeutics. The prior art is deficient in RUNX2 inhibitors or derivatives or analogs thereof and cancer treatments via these inhibitors. The present invention provides this longstanding need and desire in the art.

SUMMARY OF THE INVENTION

The present invention is directed to a compound having the chemical structure:

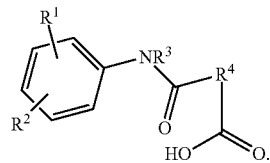

The $R_1$ and $R_2$ substituents independently are H, Cl, F, Br, $CH_3$, $CF_3$, SH, —$N(C_{1-3}alkyl)_2$, —$NHC(O)C_{1-3}alkyl$, or —$NHC(O)C_{5-7}cycloalkyl$, the $R_3$ substituent is H or $C_{1-3}$ alkyl and the $R_4$ substituents is

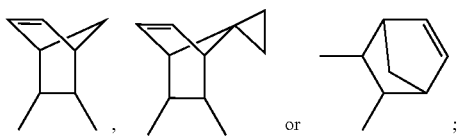

or a pharmaceutically acceptable salt thereof.

The present invention is directed to a related compound having the chemical structure:

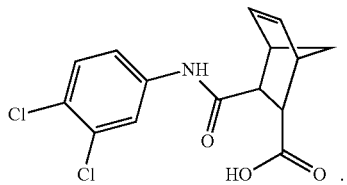 [SMILES: O=C(O)C1C2C=CC(C2)C1C(=O)Nc1ccc(Cl)c(Cl)c1]

The present invention also is directed to a pharmaceutical composition comprising any of the compounds described herein and a pharmaceutically acceptable carrier.

The present invention is directed further to a method for treating a cancer in a subject. The method comprises administering to the subject a dose of one or more of the compounds described herein effective to inhibit a RUNX2 activity, thereby treating the cancer. The present invention is directed to a related method further comprising the step of administering one or more other cancer drugs.

The present invention is directed further still to a method for inhibiting RUNX2 activity in a cancer cell. The method comprises contacting the cancer cell with one or more of the compounds described herein.

The present invention is directed further still to a method for treating a metastatic cancer in a subject. The method comprises administering to the subject a dose of one or more of the compounds described herein effective to inhibit a RUNX2 activity, thereby treating the metastatic cancer. The present invention is directed to a related method further comprising the step of administering one or more other cancer drugs.

The present invention is directed further still to a method for treating breast cancer in a subject. The method comprises administering to the subject a dose of one or more compounds described herein effective inhibiting RUNX2. The present invention is directed to a related method further comprising the step of administering one or more other cancer drugs.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3A shows that low RUNX2 expression was significantly associated with longer median survival of 80 months compared to 117.5 months for high RUNX2 expression (p=0.016). FIG. 3B shows that RUNX2 promotes attachment and invasion of MCF7 RUNX2-expressing breast cancer cells. Adhesion of MCF7 cells to tissue culture plates coated with fibronectin, extracellular matrix (ECM), or to a monolayer of EC was measured 120 min after adding tumor cells. Cell numbers indicate cells/field at high magnification (40×). Representative photographs depict MCF7 cell spreading on fibronectin, ECM, or endothelial cells monolayer 16 hr after adhesion. Arrows indicate areas where MCF7 tumor cells have invaded through the endothelial cell monolayer and attached to the underlying matrix. FIG. 3C shows that RUNX2 promotes tumorsphere formation. MCF7 RUNX2 Tet.OFF cells were resuspended in basal media for 7 days supplemented with (gray bars) or without (black bars) 2 ng/mL TGFβ in ultra-low attachment plates. Tumorsphere diameter was calculated from photographic images. The number of colonies measured is indicated in each bar graph and designated by "n". Statistical analysis (Student's t-test or ANOVA) was used to determine significance between RUNX2 positive or RUNX2 negative treatment groups. Representative photos of colonies are shown.

FIG. 4A shows that compound 1 suppresses in vitro BC cell growth in a cell growth assay in non-tumorigenic (left) and BC cell lines (middle). Cells were treated with compound 1 for 72 hrs, and cell growth was determined by crystal violet staining. Data presented as mean±SD. Experiments were done in triplicate and repeated twice. Expression of RUNX proteins in non-tumorigenic cells was determined by western blot analysis (right). FIG. 4B shows a time-dependent decrease of MDA-231 and MCF7 cell growth by compound 1. *, P<0.05 compared to vehicle control at indicated time. FIG. 4C shows a time-dependent decrease of ectopic RUNX2-expressing MCF7 and T47D cells compared to Empty controls. Cell growth was calculated as percentage (%) absorbance at indicated time point relative to absorbance of cells at Day 0. *, P<0.05 compared to Empty controls treated with vehicle alone (0.1% DMSO). #, P<0.05 compared to RUNX2-expressing cells with vehicle alone. *, and #, P<0.05 considered significant. FIG. 4D shows the cell population at each phase of the cell cycle as analyzed by flow cytometry. MDA-231 cells accumulated at the G1 and G2/M phase whereas MCF7 and MDA-468 cells were at the G1 phase after compound 1 treatment.

FIG. 5A is a cell growth assay in TNBC and luminal type BC cell lines. #, P<0.05 compared to vehicle controls. In FIG. 5B MDA-231, MDaA-468 and MCF7 cells were treated with compound 1 for 24 hrs or 72 hrs, and cellular apoptosis was determined by the Caspase-3/7 assay. In FIG. 5C MCF7-tet-off cells with or without doxy removal and T47D-Empty and T47D-RUNX2 cells were treated with compound 1 for 24 hrs and cellular apoptosis was determined by the Caspase-3/7 assay. Data are presented as luminescence intensity (Luc X 10,000). –, Vehicle controls; +, compound 1-treated cells.

In FIG. 6A T47D-Empty and T47D-RUNX2 cells were treated with compound 1 for 14 days, and clonogenic assay was performed. Photos were taken from colonies in 6-well plate (upper) and under a microscope at ×40 magnification (middle), and colonies were counted (lower). *, P<0.05 compared to the T47D-Empty cells with vehicle alone; #, P<0.05 compared to the T47D-RUNX2 with vehicle alone. –, Vehicle controls; +, compound 1-treated cells. In FIG. 6B a clonogenic survival assay was performed to determine cell survival of BC cell lines after compound 1 treatment (50 µM) for 2~3 weeks. Colonies were counted after crystal violet staining. MDA-468 and BT474 did not survive after compound 1 treatment whereas mesenchymal TNBC (MDA-231 and Hs578t) were less sensitive to compound 1 (survival >50%). Data presented as mean±SD. Experiments were done in triplicate and repeated twice. *, P<0.05 compared to control considered significant. FIG. 6C are photographs of the colonies. The periods of compound 1 treatment are indicated for each cell line. FIG. 6D are photographs of single colonies in MDA-468 cells taken in ×40 and ×100 magnification. FIGS. 6E-6F show the results of anchorage-independent cell growth assays performed with breast cancer cell lines. Colonies were counted and photographed under a microscope after 2~3 weeks of compound 1 treatment.

FIG. 7A are photographs of colony formation illustrating cell survival of various breast cancer cell lines after compound 1 treatment (50 µM) for 2~3 weeks. FIG. 7B illustrates anchorage-independent growth in soft agar of MCF7.TetOFF cells expressing RUNX2 (–doxy) or control not expressing RUNX2 (+doxy) treated with compound 1 (50 µM). The number of colonies were determined after 8 days.

FIGS. 9A-9F show that compound 1 inhibits tumorsphere formation and in vitro invasion of BC cells. In FIGS. 9A-9C compound 1 was added at the initial day of cell plating. Tumorspheres of MCF7-tet-off (–Doxy) cells were photographed for 18 days at ×40 and ×100 magnifications (FIG. 9A), and counted at the final day at ×40 magnification (FIG. 9C). Tumorspheres of MDA-231, MDA-468 and MCF7 cells at day 7 are shown (FIG. 9B). Spheres of MDA-231 and MCF7 cells were counted at day 18 with ×20 magnification. Spheres of vehicle-treated MDA-468 cells were counted at day 7 with ×20 magnification as they became fragile and disrupted 7 days after incubation. In FIG. 9C sphere number (No.) was counted from 9 fields per well. Data presented as mean±SD. Experiments were done in triplicate and repeated three times. *, P<0.05 compared to +Doxy; #, P<0.05 compared to –Doxy with vehicle treatment. Box, RUNX2 induction upon Doxy removal from MCF7-tet-off cells (–D). In FIG. 9D to ensure robust sphere formation, compound 1 was added 4 days after cell plating (D4+), and cells were further incubated for 5 days (D5) or for 7 days (D7). In FIG. 9E the cellular invasive ability of MCF7-tet-off cells (left) was evaluated by the 96 Well BME Cell Invasion Assay and xCELLigence systems in vitro, respectively. In parallel, similar amount of cells were plated in separate plates and treated with compound 1 for 24 hrs, and Calcein-AM assay was performed (right). Highly metastatic MDA-231 cells were used as a positive control for cellular invasion. Data are presented as fluorescent intensity (Flu). In FIG. 9F the average Cell Index (impedance-based signals) between control and compound 1-treated cells showed little difference in 24 hrs, but decreased by compound 1 in 48 hrs. Medium without cells was used as a negative control.

In FIGS. 10A-10B ectopic RUNX2-expressing T47D and MCF7 cells with their Empty controls were transfected with indicated luciferase plasmids and treated with compound 1 for 48 hrs. Relative Luc activity (Fold) was calculated from the ratio of target gene Luc activity to pGL3 activity after normalization of pRenilla activity. Increasing concentrations of compound 1 are indicated for each set of data. Data presented as mean±SD. Experiments were done in triplicate and repeated twice. P values are indicated and <0.05 were considered significant. FIG. 10C shows that compound 1 does not inhibit the activity of promoters that do not have Runt binding sequences. MCF7-RUNX2 and MCF7-Empty cells were transfected with COX-2 (P2-274)-Luc and control plasmids (PXP2-Luc) (left). In separate experiments, cells were transfected with pNF-kb-Luc plasmids. After 6 hrs, cells were treated with compound 1 (0~50 mM) in the absence (1×PBS-0.1% BSA) or in the presence of TNF-a (20 ng/ml) for 24 hrs (right). n.s., not significant. 0.1% DMSO was used as a vehicle control.

In FIG. 11A T47D-RUN2 and T47D-Empty cells were transfected with the indicated luciferase plasmids and treated with compound 1 for 48 hrs. Relative Luc activity (Fold) was calculated from the ratio of indicated luciferase plasmids activity to pGL3 activity after normalization of pRenilla activity. Data preented as mean±SD. Experiments were done in triplicate and repeated twice. P<0.05 is considered significant. In FIG. 11B MDA-231 cells that express both RUNX1 and RUNX2 and BT474 cells that express only RUNX1 among RUNX family proteins were transfected with pMMP13-Luc plasmids and treated with compound 1 for 48 hrs. *, P<0.05 compared to pGL3-Luc with vehicle control. #, P<0.05 compared to pMMP13-Luc with vehicle control. n.s., not significant. Box, MMP13 mRNA expression in BT474 cells was confirmed by RT-PCR analysis. MDA-231 cells were used for a positive control.

In FIG. 12A Q-RT-PCR analyses of MMP13, VEGF, and MMP9 were performed in ectopic RUNX2-expressing T47D and MCF7 cells. Cells were treated compound 1 (50 μM) for 72 hrs. *, P<0.05 compared to Empty controls with vehicle alone (−); #, P<0.05 compared to RUNX2-expressing cells with vehicle control. FIG. 12B shows Q-RT-PCR analyses of RUNX2 target genes in MDA-231 cells. Cells were treated with compound 1 (50 μM) for 6 hrs. Similar results were observed in cells treated with compound 1 for 24 hrs (data not shown). *, P<0.05 compared to vehicle control (0.1% DMSO).

FIG. 13C shows the levels of glucose in the cell culture medium prepared from breast cancer cells treated with or without compound 1 for 24 hrs.

FIGS. 14A-14G show that compound 1 alters glucose consumption and lactate production. The levels of glucose (FIGS. 14A-14C) and lactate (FIGS. 14D-14F) were measured in the cell culture medium prepared from BC cells treated with or without compound 1 treatment for 6 hrs for Ectopic RUNX2-expressing MCF7 and T47D cells (FIGS. 14A, 14D), MDA-231, MDA-468 and MCF7 cells (FIGS. 14B, 14D) and Hs578t cells with RUNX2 KD (FIGS. 14C, 14F). Data presented as mean±SD. Experiments were done in triplicate and repeated twice. *, P<0.05 compared to Empty controls with vehicle alone, to untreated control, or to NTC; #, P<0.05 compared to RUNX2 expressing cells with vehicle controls. P<0.05 considered significant. FIG. 14G shows the Q-RT-PCR analysis for Glut-1 and LDHA mRNA expressions in ectopic RUNX2-expressing T47D and MCF7 cells. Cells were treated compound 1 (50 μM) for 72 hrs.

FIG. 15A shows the compensatory expression of RUNX1 and RUNX2. Left, Pa, parental Hs578t cells; Neg, a negative clone of RUNX2 KD cells (54.5); NTC, a clone for non-targeting control; 55.5, a positive clone for RUNX2 KD. Clones were established under puromycin selection. BT549 cells transfected with RUNX2 or NTC siRNA for 48 hrs. β-actin was used a loading control. Middle, 55.5 cells transfected RUNX1 or NTC siRNA for 48 hrs. Right, Q-RT-PCR analysis in NTC and 55.5 cells to determine the levels of RUNX1 and RUNX2. Data presented as mean±SD. Experiments were done in triplicate and repeated twice. *, P<0.05 compared to NTC was considered significant. In FIG. 15B (left) MCF7-tet-off cells were treated with Doxycyclin (+D) for RUNX2 repression and removed (−D) for RUNX2 induction. MCF7-RUNX2 and MCF7-Empty cells were cloned and grown under G418 selection. In FIG. 15B (right) T47D-Empty (E) and T47D-RUNX2 (RUNX2) cells were treated with compound 1 (50 μM) for 72 hrs, and isolated protein lysates were processed for western blot analysis with indicated antibodies. −, vehicle; +, compound 1. FIG. 15C is a Q-RT-PCR analysis in MCF7 and T47D cells expressing ectopic RUNX2 and Empty controls. *, P<0.05 compared to Empty controls with vehicle alone; #, P<0.05 compared to RUNX2-expressing cells with vehicle alone. −, Vehicle controls; +, compound 1-treated cells. In FIG. 15D BC cell lines were treated with compound 1 for indicated time periods, and RUNX2 and RUNX1 expression levels were determined by western blot analysis.

In FIGS. 16A-16C CBF-β expression was determined by western blot analysis. MDA-231 and BT474 cells were transfected with RUNX1, RUNX2 or NTC siRNA for 48 hrs. Compound 1 (50 μM) was treated for 72 hrs. Otherwise, time periods for treatment are indicated in various BC cell lines. Pa, parental Hs578t cells; Neg, a negative clone of RUNX2 KD cells (54.5); NTC, a clone for non-targeting control; 55.5, a positive clone for RUNX2 KD. FIG. 16D shows changes in RUNX2, RUNX1 and CBF-β protein stability under Cycloheximde (CHX, 25 μg/ml) and/or compound 1 (50 μM) treatment for 0, 2, 4 and 6 hrs. In FIG. 16E MDA-468 and MCF7 cells were pre-treated (Pre-T) with MG132 (10 μM) for 1 hr, and then incubated with or without compound 1 in the presence of MG132 for further 18 hrs (left). In separate experiments, MDA-468 and MCF7 cells were pre-treated (Pre-T) with or without compound 1 for 6 hrs, and MG132 was added for further incubation for 18 hrs (right). In FIG. 16F S451-p-RUNX2 levels were determined in MCF7 and T47D cells expressing ectopic RUNX2 after compound 1 (50 μM) treatment for 72 hrs. MDA-231, MDA-468 and MCF7 cells were treated with compound 1 for 24 hrs or 72 hrs.

FIG. 18A shows endogenous RUNX2 expression in MCF7Parental, T47D, and HCC1428 BC cells. Nuclear protein fractions were obtained using the High/Low salt extraction method detailed in FIG. 2A. Cells were grown in full media (DMEM for MCF7 parental; RPMI for T47D and HCC1428) and then fractionated. Proteins were resolved by SDS-PAGE and RUNX2 protein bands were visualized using a RUNX2 specific antibody (Cell Signaling) to detect endogenous RUNX2 and FLAG-tagged RUNX2. FIG. 18B shows that RUNX2 does not promote an EMT. MCF7 cells expressing ectopic RUNX2 or Hs578t cells expressing endogenous RUNX2 were grown for 3 days in + or − Doxycycline media or in full media, respectively. Cells were starved overnight in minimal DMEM supplemented with 2% FBS and 1 mM glucose and treated with 2 ng/mL TGFβ or left untreated for 48 hr. Nuclear/Cytoplasmic extracts were obtained using a High/Low salt protocol and proteins were resolved by SDS-PAGE. Immunoblots were probed with antibodies for E-Cadherin (120 kDa; 80 kDa), N-Cadherin (135 kDa), ER-66 kDa), Vimentin (57 kDa), RUNX2 (60 kDa MCF7; 55 kDa Hs578t), or β-actin (Sigma-Aldrich). FIG. 18C shows that YAP expression and localization are not affected by RUNX2 in MCF7 cells. MCF7 Tet.OFF cells cultured in the presence (doxycycline+, RUNX2 negative) or absence (doxycycline−, RUNX2 positive) of doxycycline were analyzed for changes in YAP localization using specific antibodies. YAP was detected in both cytoplasmic and nuclear fractions of both RUNX2 positive and negative cells.

FIG. 19A shows that higher levels of nuclear TAZ are found in RUNX2 positive cells. MCF7 Tet.OFF cells were grown in the presence (RUNX2−) or absence (RUNX2+) of doxycycline for 3 days and starved 16 hr in minimal DMEM supplemented with 1 mM glucose and 2% FBS (t=0). Cells were then treated for 48 hr with 2 ng/mL TGFβ with or without EGTA (500 μM or 1 mM). Cytoplasmic and nuclear extracts were resolved by SDS-PAGE and immunoblots were probed with antibodies for YAP/TAZ (50 kDa), FLAG (RUNX2, 60 kDa), and β-Actin (42 kDa). Cytoplasmic and nuclear TAZ (50 kDa) protein bands were normalized to β-Actin, quantified using Image-J, and graphed as fold-change relative to RUNX2 negative cells. FIG. 19B shows that RUNX2 and TAZ associated in the same immune complex. Cells were either cultured in Full Media (DMEM, 10% FBS) or starved in minimal DMEM media supplemented with 1 mM glucose and 2% FBS for 16 hr. Nuclear lysates (400 µg) were immunoprecipitated (IP) using YAP/TAZ antibody, resolved by SDS-PAGE, and immunoblots were probed for RUNX2 and TAZ. To visualize TAZ expression a conformation-specific Rabbit IgG was used. Rabbit IgG and beads alone were used as controls. Inputs are nuclear lysates. FIG. 19C shows TAZ knockdown in MCF7 Tet.OFF RUNX2 cells. MCF7 Tet.OFF RUNX2 cells were treated with siRNA targeting three different regions of the TAZ mRNA or scrambled siRNA control. Protein levels of TAZ (50 kDa) were assayed 96 hr post-transfection. FIG. 19D shows that knockdown of TAZ protein inhibits tumorsphere formation. MCF7 Tet.OFF RUNX2 cells were transfected with TAZ siRNA or scrambled control and 24 hr post transfection cells were scraped from dishes and resuspended in basal media supplemented with 2 ng/mL TGFβ in ultra-low attachment plates. After growth for 12 days, wells were photographed and tumorsphere sizes were measured from photographic images. Statistical analysis was performed using Student's t-test or ANOVA to determine significance between RUNX2 treatment groups. Representative photos of colonies are shown. FIG. 19E shows inhibition of TAZ nuclear localization in RUNX2 positive MCF7 and HCC1428 cells treated with compound 1. MCF7 Tet.OFF RUNX2 cells were grown with (RUNX2−) or without (RUNX2+) doxycycline and treated for 24, 48, or 72 hr with 50 µM compound 1 drug. Nuclear proteins were collected using the High/Low salt extraction method and resolved by SDS-PAGE. Proteins were visualized using antibodies against YAP/TAZ (50 kDa) and β-actin (42 kDa). TAZ protein bands were quantified using Image-J and normalized to β-actin. Fold changes relative to untreated cultures are indicated. TAZ nuclear protein levels were unaffected in compound 1-treated RUNX2 negative cells (MCF7+doxycycline; 72 hr).

FIG. 20A shows that RUNX2 increases the production of sE-Cad associated with the cell surface in response to TGFβ. MCF7 Tet.OFF cells were grown in the presence (RUNX2−) or absence (RUNX2+) of doxycycline for 3 days and starved 16 hr in minimal DMEM supplemented with 1 mM glucose and 2% FBS (t=0). Cells were then treated for 48 hr with 2 ng/mL TGFβ with or without EGTA (500 µM or 1 mM). Cytoplasmic and nuclear fractions were obtained and resolved by SDS-PAGE. Immunoblots were probed with antibodies for E-Cadherin (120 kDa=full length; 80 kDa=sE-Cad), FLAG (RUNX2; 60 kDa), and β-Actin (42 kDa). FIG. 20B shows that RUNX2 positive MCF7 cells secrete higher levels of sE-Cad. Conditioned media from MCF7 Tet.OFF cells were collected following a 16 hr starvation in minimal DMEM supplemented with 1 mM glucose and 2% FBS (t=0) or after treatment with 2 ng/mL TGFβ for 48 hr. Conditioned media were centrifuged to remove cellular debris, and immunoprecipitated using 0.5 µg of E-Cadherin antibody. Proteins were eluted from beads and separated by SDS-PAGE followed by Western blot with antibodies to detect full-length (120 kDa) and ectodomain (80 kDa) sE-Cad. FIG. 20C shows sE-Cad-mediated tumorsphere formation in RUNX2-expressing MCF7 cells. MCF7 cells were cultured in suspension in basal media supplemented with 2 ng/mL TGFβ with or without (TGFβ untreated ctrl and IgG isotype control) an E-Cadherin specific antibody, DECMA-1. After 10 days, wells were photographed and tumorsphere sizes were measured from photographic images. Statistical analysis was performed using Student's t-test or ANOVA. FIG. 20D shows that treatment with compound 1 inhibits sE-Cad production. MCF7 Tet.OFF cells were and treated for 24, 48, or 72 hr with 50 µM compound 1. Cytoplasmic fractions were obtained using the High/Low salt extraction method and proteins were resolved by SDS-PAGE. Proteins were visualized using antibodies against E-Cadherin (Full length=120 kDa; sE-Cad=80 kDa) and β-actin (42 kDa). SDS-PAGE was performed in triplicate and results were quantified. FIG. 20E shows the effect of TAZ knockdown on sE-Cad production. TAZ siRNA#1 (FIG. 18C) was used to reduce TAZ levels and the expression of E-Cadherin (120 kDa and 80 kDa), TAZ (cytoplasmic or nuclear) and RUNX2 (FLAG) was determined by Western blot. Quantitation represents results from 3 separate gels.

FIG. 21A shows that TGFβ treated RUNX2 positive MCF7 cells express HER2. MCF7 Tet.OFF cells were grown in the presence (RUNX2−) or absence (RUNX2+) of doxycycline for 3 days and starved for 16 hr in minimal DMEM supplemented with 1 mM glucose and 2% FBS (t=0). Cells were then treated for 48 hr with 2 ng/mL TGFβ with or without EGTA (500 µM or 1 mM). Cytoplasmic and nuclear fractions resolved by SDS-PAGE and immunoblots were probed with antibodies for HER2 (180 kDa), FLAG (RUNX2; 60 kDa), or β-Actin (42 kDa). FIG. 21B shows that TGFβ cells expressing RUNX2 are sensitive to Herceptin. MCF7 RUNX2 Tet.OFF cells were cultured in suspension in basal media for 10 days supplemented with 2 ng/mL TGFβ with or without (IgG isotype control) 10 µg/mL Herceptin (replenished every 2-3 days). Representative photos of colonies are shown. FIG. 21C shows that TGFβ RUNX2 positive cells are sensitive to Lapatinib treatment. MCF7 RUNX2 Tet.OFF cells were cultured in suspension for 15 days in 2 ng/mL TGFβ with or without (DMSO control) 1 µM lapatinib. Representative photos of colonies are shown.

In FIG. 22A HCC1428 luminal BC cells that express E-Cadherin were treated with recombinant soluble E-Cadherin (rsE-Cad) for 24 hr and total cell extracts were analyzed for phosphorylation of the Lats1/2 tumor suppressors. Phospho.Lats1/2 and total Lats1/2 levels declined with rsE-Cad treatment consistent with TAZ translocation to the nucleus, where it acts as an oncogene with RUNX2. FIG. 22B shows that RUNX2 targeting with compound 1 increases pLats1 and total Lats1/2. MCF7 cells expressing RUNX2 (Tet.OFF) were treated with compound 1 drug for 24 hours and total cell extracts were analyzed for phosphp.Lats1/2, total Lats1/2, and RUNX2 expression.

In FIG. 23A PDH enzymatic activity was determined in doxycycline-responsive MCF7-tet-off (left) and Hs578t-Control or RUNX2 KD cells (right) or non-targeting control siRNA (NTC=RUNX2+) versus RUNX2 KD (55.5 cells=RUNX2 KD) using an antibody-specific microtiter plate assay. Results are expressed as the change in Absorbance at 450 nm per minute per mg protein ($\Delta mOD_{450}$/min/mg) (*$p<0.05$). In FIG. 23B PDH activity was determined in MDA-MB-468 (left) and MCF7 (right) BC cell lines with or without compound 1 treatment (50 µM) for the indicated time period.

In FIG. 24A MDA-231 or BT-474 breast cancer cells were treated with 50 µM compound 1 for 3 hr or 1-3 days. FIG. 24B shows controls T47D-Vector control or T47D-RUNX2-clone #10 overexpressing cells; MCF7-Vector Control or RUNX2-clone #2 overexpressing cells treated with 50 µM compound 1 for 1 day.

FIGS. 25A-25D demonstrate that RUNX2 and compound 1 regulates PDH complex. FIG. 25A shows that RUNX2 increases PDHE1α phosphorylation (Ser293), but decreases PDP1 level. In contrast, RUNX2 KD decreases PDHE1α phosphorylation but increases PDP1. Immunoblot analyses were performed using antibodies indicated in T47D-RUNX2 and -Empty cells (left) and in Hs578t cells (middle). Parental, non-transfectant; 54.5, a negative clone for RUNX2 KD; Control, non-targeting control; RUNX2 KD, a positive control for RUNX2 KD. In FIG. 25B MDA-MB-231, MDA-MB-468 and MCF7 cells were treated with compound 1 (50 µM) for indicated time period and the expression of PDP1, p-PDHE1α and total PDHE1α were determined. FIG. 2C shows that compound 1 inhibits RUNX2 phosphorylation and levels of RUNX2 cofactor, CBFβ. FIG. 25D shows that compound 1 inhibits CBFβ levels in MDA-231 cells.

In FIG. 26A MDA-231, MDA-468, MCF7, and BT-474 breast cancer cells were treated with compound 1 (50 µM) for 1-3 days. Complex I activity increased in MDA-468 and MCF7 cells. In FIG. 26B T47D-Vector control or T47D-RUNX2-clone #10 overexpressing cells; MCF7-Vector Control or RUNX2-clone #2 overexpressing cells were treated with 50 µM compound 1 for 1 day.

In FIG. 27A MDA-231, MDA-468, MCF7 and BT474 breast cancer cells were treated with compound 1 (0-100 µM) for 6-18 hours and ROS production in response to H2O2 treatment (2 mM) was measured with luciferase-based luminometer assay. In FIG. 27B T47D-Vector control or T47D-RUNX2-clone #10 overexpressing cells; MCF7-Vector Control or RUNX2-clone #2 overexpressing cells were treated with 50 µM compound 1 for 6 hours.

FIG. 28A shows RUNX2 expression in normal mammary gland (N) and mammary tumor samples (T) isolated from age-matched wild-type or MMTV-PyMT transgenic mice. FIG. 28B shows that no significant decrease on body weight was observed in compound 1-injected MMTV-PyMT mice. Values in y-axis are % body weight from day 1. FIG. 28C shows RUNX2 expression in consecutive passages of the TNBC-PDX Br-001 model. Protein lysate from MDA-231 cells was used as a positive control. Percentage of body weight from day 1 in TNBC-PDX Br-001 bearing mice (FIG. 28D) and 231-luc injected NGS mice (FIG. 28E).

FIGS. 29A-29I show that compound 1 suppresses in vivo BC cell growth and metastasis. In FIG. 29A MMTV-PyMT female mice were injected with compound 1 for 45 days, and detection of first palpable tumors (tumor onset) was depicted. Vehicle (10% DMSO in 90% PBS) was injected in mice for 0 mg/kg compound 1. Data represent combined results from two separate experiments. The range of vehicle control was 1~44, of 1 mg/kg compound 1 was 15~45, of 5 mg/kg compound 1 was 1~45, and of 20 mg/kg compound 1 was 22~45. Mode/Frequency of vehicle control was 39/9, of 1 mg/kg compound 1 was 43/8, of 5 mg/kg compound 1 was 43/11, and of 20 mg/kg compound 1 was 40/9. *, P=0.0086; , P=0.0051, *, P=0.0007 (Mann-Whitney test). P<0.05 considered significant. Black lines, median values in each group. FIG. 29B, left, shows the tumor incidence (tumor number per mouse) determined by palpation of all 10 mammary glands from day 1 to day 90. Data presented as mean±SE. *, P=0.037; **, P=0.008 (Student's t-test). FIG. 29B, right, shows the fraction of mice with tumors (%) at the final day. Note, no mice treated with 20 mg/Kg of compound 1 had over 6 tumors. *, P=0.007; **, P=0.05 (Student's t-test). FIG. 29C shows the median tumor weight with min/max values depicted via Box/Whisker plot. Tumors were excised from control mice (n=13), 1 mg/Kg (n=15), 5 mg/Kg (n=20) and 20 mg/Kg compound 1-treated mice (n=17), and weighed after mice were sacrificed. *, P=0.0034; , P=0.0002, *, P=0.0005 (Mann-Whitney test). In FIG. 29D representative tumors excised from a mouse are shown. Scale bar, 2 cm. FIG. 29E is an analysis of Ki67- and RUNX2-positive proliferating cells within MMTV-PyMT mice. Shown are representative fields from 3 separate tumors per group. $2^{nd}$ antibody alone was used as a negative control. Scale bar=100 mm. In FIG. 29F TNBC-PDX Br-001-bearing mice were treated with compound 1, and tumor volume (mean±SEM) was determined for 11 days. *, P=0.002; **, P=0.005 (Student's t-test). FIG. 29G is an IHC analysis of Br-001 tumors with Ki-67 and RUNX2 antibody. Scale bar=100 mm. The lung retention of MCF7-tet-off-Luc (−Doxy) cells that express ectopic RUNX2 (FIG. 29H) and 231-Luc cells (FIG. 29I) was monitored by BLI analysis. Vehicle or 10 mg/kg compound 1 was administrated into NSG mice. Data presented as mean±SE of PI (Photon Intensity) (Student's t-test), and P<0.05 compared with control were considered significant (left). Left, Representative images.

FIG. 3A illustrates cell proliferation. MDA-231 TNBC cells were treated with compound 1 in the presence or absence of CDK2 inhibitor (SU9516), CDK4 inhibitor (CdK4.I-II) or CDK4/6 inhibitor (Paloma; palbociclib) for 6 days and cell growth was determined by crystal violet staining. Data presented as mean±SD. Experiments were done in triplicate and repeated twice. Half-maximal inhibition is indicated by the dotted line. FIG. 30B shows in colony focus assays that compound 1 increases CDK inhibitor Palbociclib drug sensitivity. MDA-231, MCF7, or MDA-468 cells were treated with the indicated drug combinations (one time) for 9-13 days. Colonies were counted after crystal violet staining. Similar trend was observed in cells treated with CDK4.I-II (data not shown). *P<0.005; **P<0.0005.

DETAILED DESCRIPTION OF THE INVENTION

Figure 1A:
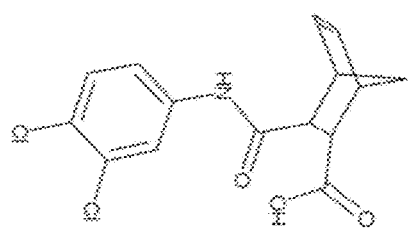
FIGS. 1A-1K depict the structures of compound 1 and analog compounds 2-11 and their percent similarity to compound 1.
Figure 1B:
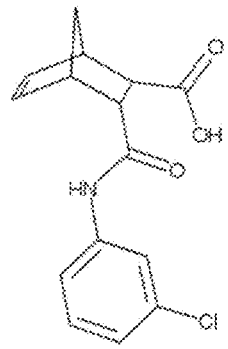
Figure 1C:
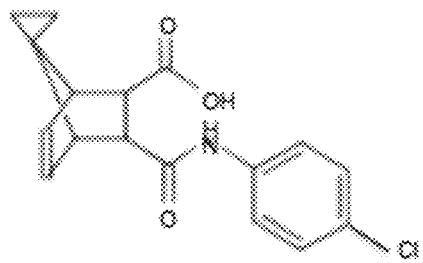
Figure 1D:
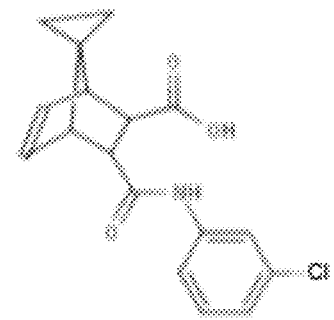
Figure 1E:
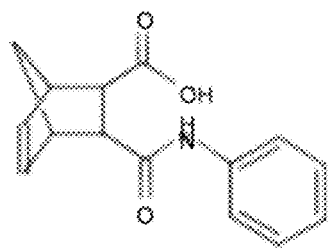
Figure 1F:
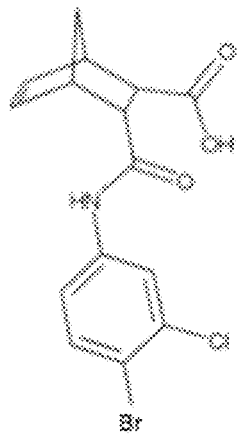
Figure 1G:
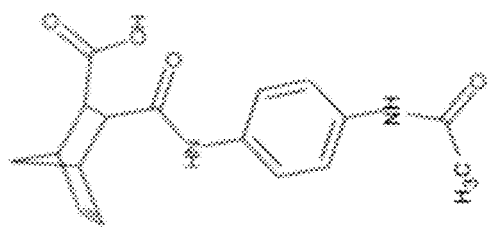
Figure 1H:
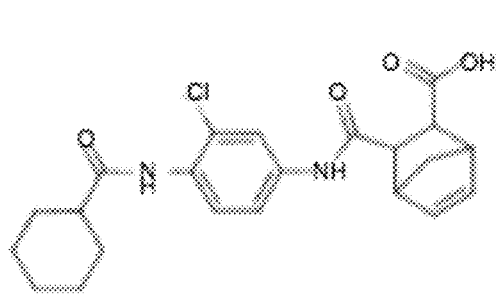
Figure 1I:
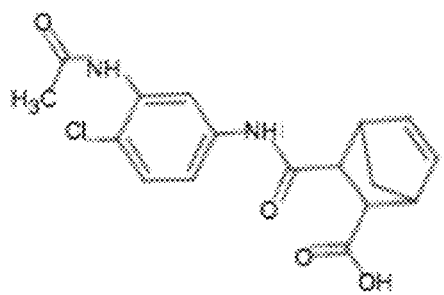
Figure 1J:
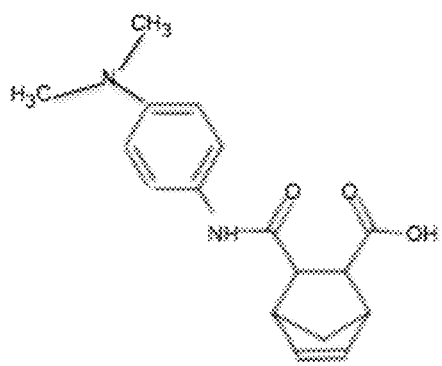
Figure 1K:
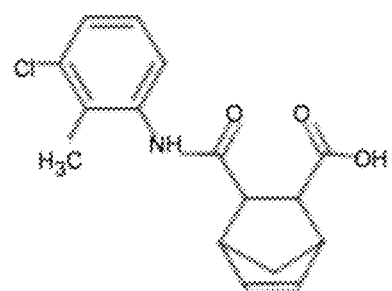

As used herein, the term "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method described herein can be implemented with respect to any other method described herein.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, "comprise" and its variations, such as "comprises" and "comprising," will be understood to imply the inclusion of a stated item, element or step or group of items, elements or steps but not the exclusion of any other item, element or step or group of items, elements or steps unless the context requires otherwise. Similarly, "another" or "other" may mean at least a second or more of the same or different claim element or components thereof.

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the terms "compound", "inhibitory compound" and "inhibitor" refer to a chemical entity effective to inhibit an activity of RUNX2 in a cancer cell such as, but not limited to, inhibiting RUNX2 protein, inhibiting RUNX2 over expression or inhibiting RUNX2 gene.

As used herein, the term "contacting" refers to any suitable method of bringing a compound or a composition into contact with a cell. For in vivo applications, any known method of administration is suitable as described herein.

As used herein, the term "subject" refers to any human or non-human recipient of the compounds or pharmaceutical compositions thereof described herein.

In one embodiment of the present invention there is provided a compound having the chemical structure:

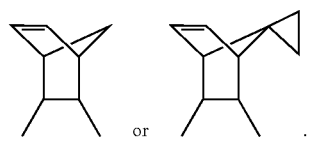

where $R_1$ and $R_2$ independently are H, Cl, F, Br, $CH_3$, $CF_3$, SH, $-N(C_{1-3}alkyl)_2$, $-NHC(O)C_{1-3}alkyl$, or $-NHC(O)C_{5-7}cycloalkyl$; $R_3$ is H or $C_{1-3}$ alkyl; and $R_4$ is

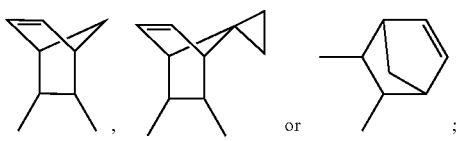

or a pharmaceutically acceptable salt thereof.

In one aspect of this embodiment $R_3$ may be NH. In another aspect $R_1$ and $R_2$ $R_1$ and $R_2$ independently may be H, Cl, Br, or $-NHC(O)CH_3$, $R_3$ is NH and $R_4$ is

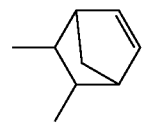

In yet another aspect $R_1$ and $R_2$ independently may be H, Cl, $CH_3$, $-NHC(O)CH_3$, $-NHC(O)cyclohexane$, or $-N(CH_3)_2$, $R_3$ may be NH and $R_4$ may be

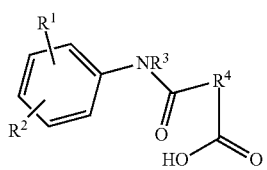

Particularly, compounds of this embodiment are those depicted in FIGS. 1A-1K.

In another embodiment of the present invention there is provided a compound having the chemical structure:

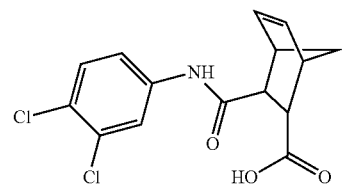 [SMILES: O=C(O)C1C2C=CC(C2)C1C(=O)Nc1ccc(Cl)c(Cl)c1]

or a pharmaceutically acceptable salt thereof.

In a related embodiment the present invention provides a pharmaceutical composition comprising the compound as described supra and a pharmaceutically acceptable carrier.

In yet another embodiment of the present invention there is provided a method for treating a cancer in a subject, comprising administering to the subject a dose of one or more compounds as described supra effective to inhibit a RUNX2 activity, thereby treating the cancer. Further to this embodiment the method comprises administering one or more other cancer drugs. Non-limiting examples of cancer drugs are Herceptin, Lapatinib, or DECMA1 antibody. In both embodiments the cancer may be breast cancer, osteosarcoma, ovarian cancer, prostate cancer, melanoma, Ewing sarcoma, pancreatic cancer, thyroid cancer, leukemia, head/neck cancer, colorectal cancer, liver cancer, lung, pituitary cancer, gliomas, esophageal cancer, or multiple myeloma. Alternatively, the cancer may be a metastatic cancer.

In a related embodiment the present invention provides a method for treating breast cancer in a subject comprising administering to the subject a dose of one or more compounds as described supra effective to inhibit RUNX2, thereby treating the cancer. A further embodiment comprises administering one or more other cancer drugs as described supra. In these embodiments the breast cancer may comprise metastases thereof.

In yet another embodiment of the present invention there is provided a method for treating a metastatic cancer in a subject, comprising administering to the subject a dose of one or more compounds of described herein effective to inhibit a RUNX2 activity, thereby treating the metastatic cancer. A further embodiment comprises administering one or more other cancer drugs as described supra. In both embodiments the metastatic cancer may originate from a breast cancer, a lung cancer, a melanoma, a colorectal cancer, a prostate cancer, or a pancreatic cancer.

In yet another embodiment of the present invention there is provided a method for inhibiting RUNX2 activity in a cancer cell, comprising contacting the cancer cell with one or more of the compounds as described supra. In this embodiment the cancer cells may comprise a breast cancer, an osteosarcoma, an ovarian cancer, a prostate cancer, a melanoma, a Ewing sarcoma, a pancreatic cancer, a thyroid cancer, a leukemia, a head/neck cancer, a colorectal cancer, a liver cancer, a lung, a pituitary cancer, a gliomas, an esophageal cancer, or a multiple myeloma.

Provided herein are compounds or inhibitory compounds effective to inhibit RUNX2 activity in a cancer. The compounds may have the general chemical structure of:

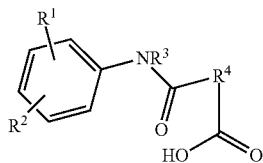

or may be a suitable pharmacologically effective salt thereof. Generally, $R_1$, $R_2$ and $R_3$ substituents may comprise independently, hydrogen, a halogen, a haloalkyl, a short chain alkyl, an alkylamide, a cycloalkylamide or an alkylamine. In non-limiting examples the alkyl moiety is a such as a $C_{1-3}$ alkyl chain and the cycloalkyl moiety is a such as a $C_{5-7}$ ring. The $R_4$ substituent is a bridged cycloalkenyl ring for example, but not limited to, a cyclohexene ring with a small alkyl bridge, such as a methylene bridge. Optionally, the bridge may be substituted with a small cycloalkyl ring, such as a cyclopropane ring. The compounds of the present invention encompass homologs, bioisosteres and/or positional isomers of the general chemical structure.

For example, the inhibitory compound may be 3-(N-(3, 4-dichlorophenyl)carbamoyl)-5-norbornene-2-carboxylic acid (compound 1) and have the chemical structure of:

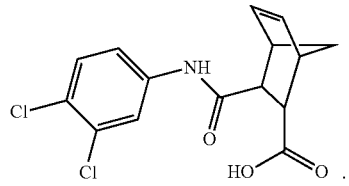 [SMILES: O=C(O)C1C2C=CC(C2)C1C(=O)Nc1ccc(Cl)c(Cl)c1]

This compound may be utilized as a lead compound to screen for chemically-related analogs, such as, but not limited to, analogs with a high homology. Screening methods for drug analogs are well-known in the art. Particularly, compound 1 of the present invention is depicted in FIG. 1A and analog compounds 2-11 are depicted in FIGS. 1B-1K.

Also provided are pharmaceutical compositions of the RUNX2 inhibitory compounds. As is known and standard in the art, the inhibitory compounds are formulated with, although not limited to, a pharmacologically acceptable carrier, diluent or excipient. The phrase "pharmaceutically acceptable" refers to molecular entities and compositions that do not produce an adverse, allergic or other untoward reaction when administered to an animal, such as, for example, a human, as appropriate. The preparation of an pharmaceutical composition that contains an inhibitory compound and/or additional drug will be known to those of skill in the art in light of the present disclosure, as exemplified by Remington's Pharmaceutical Sciences, 18th Ed. Mack Printing Company, 1990, incorporated herein by reference.

These carriers include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, gels (e.g., gelatin), dyes, such like materials and combinations thereof, as would be known to one of ordinary skill in the art. Except insofar as any conventional carrier is incompatible with the active ingredient, its use in the therapeutic or pharmaceutical compositions is contemplated.

The inhibitory compounds described herein and other RUNX2 inhibitors may be administered orally or parenterally. An oral composition may comprise one or more binders, excipients, disintegration agents, lubricants, flavoring agents, and combinations thereof. A composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

For parenteral administration, in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The inhibitory compounds and compositions described herein may be used to treat one or more types of cancers. These RUNX2 inhibitory compounds, compositions and methods have one or more benefits over existing treatments. While many of the working examples are described for the treatment of breast cancer, such as luminal breast cancer, a person having ordinary skill in the art would readily understand that the teachings provided herein can be used to treat other types of cancer including but not limited to osteosarcoma, breast, ovarian, prostate, melanoma, Ewing sarcoma, pancreatic, thyroid, leukemia, head/neck, colorectal, liver, lung, pituitary, gliomas, esophageal, and multiple myeloma. Moreover, these inhibitory compounds and compositions may be used to target and treat metastases or metastatic cancers, such as, but not limited to, metastases originating from breast cancer, lung cancer, melanoma, colorectal cancer, prostate cancer, and pancreatic cancer or other. As such, these inhibitory compounds and compositions inhibit or decrease metastasis or the incidence of metastasis by decreasing migration of cancer cells from the cancer.

The inhibitory compounds and compositions described herein may be administered independently or in combination with one or more known drugs, such as cancer drugs or anti-cancer agents. Examples of cancer drugs are Herceptin, Lapatinib, and DECMA1 antibody. A non-limiting dosage range for compound 1 for example is about 1 mg/kg and 20 mg/kg.

Generally, it is known in the art that a dosage amount or therapeutically effective amount of an inhibitory compound and/or other known drug or pharmaceutical compositions of the present invention administered to a human or animal patient can be determined by physical and physiological factors such as body weight, severity of condition, the type of cancer being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The following example(s) are given for the purpose of illustrating various embodiments of the invention and are not meant to limit the present invention in any fashion.

EXAMPLE 1

Methods and Materials
Cell Culture

The MCF7 breast cancer cell line with inducible RUNX2 expression (ER+ MCF7) was prepared using the BD™ Tet-Off System (BD Biosciences). RUNX2– MCF7 cells are ER+ and express wild type p53, PTEN, c-myc, and ras, but do not express p16. MCF7 cells containing tTA (Tetracycline-controlled transactivator) regulatory vector (G418 resistant) were purchased from Clontech (Mountain View, Calif.), infected with retroviral vectors expressing RUNX2, and selected with 200 µg/ml hygromycin B. Cells were frozen within three passages and maintained in DMEM (Corning) containing 10% Tet-Approved FBS (Clontech) and the antibiotics G418 (100 µg/ml; Sigma), hygromycin B (200 µg/ml; Roche), and doxycycline (2 µg/ml; Sigma) to repress RUNX2 expression (+Dox). To express RUNX2, cells were grown in the same media but in the absence of doxycycline (–Dox) for 72 hours to achieve maximal RUNX2 protein levels. T47D and HCC1428 luminal breast cancer cells were obtained from ATCC (Manassas, Va.) and were a gift from Dr. Stuart Martin (University of Maryland). They were maintained in RPMI (Corning) containing 10% FBS (Gemini; #100-106) with 1% Pen/Strep (Gemini; #400-109). T47D luminal breast cancer cells was also supplemented with 0.2 Units/mL bovine insulin (Sigma; #10516). To validate EMT markers, the triple negative Hs578t cells were obtained from ATCC (Manassas, Va.) and maintained in DMEM (Corning) supplemented with 5% FBS (Gemini) and 1% Pen/Strep (Gemini). MDA-MB-231-Luc-Hyg (231-Luc) and MCF7-tet-off-Luc-Puro cells stably expressing firefly luciferase (Luc) were cloned under hygromycin (250 µg/ml) and puromycin (0.5 µg/ml) selection, respectively. The bioluminescence intensities in 231-Luc and MCF7-tet-off-Luc (–Doxy) were over 600 and 900-fold higher than those in parental MDA-231 and MCF7-tet-off (–Doxy), respectively indicating that the bioluminescence intensity of these cells was sufficient for in vivo bioluminescence imaging analysis.

Suspension Culture—Tumorsphere Formation

MCF7 Tet.OFF cells were grown in the presence (+Dox, RUNX2 negative) or absence (–Dox, RUNX2 positive) of doxycycline for 3 days. Cells were then scraped and counted. 60,000 cells were plated in each well of a 6-well ultra-low attachment plate (Corning; 3471) in Promocell Basal Medium (Promocell; c-22211) complete with Supplement Mix (Promocell; c-39216). Cells were then treated with or without 2 ng/mL TGFβ (R&D Systems; 240-B-002). After growth for 10-15 days, wells were photographed and tumorsphere diameters were measured from photographic images (mm). Colony diameters were calculated using the formula: (L+W)/2. Representative photographs were obtained at 4× magnification. Other treatments included: 50 µM compound 1 (ChemBridge Corporation; 5221975), 20 µg/mL DECMA-1 (Sigma-Aldrich; U3254), 10 µg/mL Herceptin (replenished every 2-3 days; the University of Maryland Marlene and Stuart Greenebaum Cancer Center), and 1 µM Lapatinib (kind gift from Dr. Anne Hamburger at the University of Maryland Baltimore). For TAZ siRNA knockdown experiments, TAZ siRNA was transfected (as below) into MCF7 Tet.OFF cells and 24 hr later cells were scraped and placed into suspension as described above. Small-Interfering RNA (siRNA) pool targeting RUNX1, RUNX2, and non-targeting control were purchased from Dharmacon, and transfected into cells using RNAiMAX Reagent (Invitrogen). Western blot analysis was performed 48 hrs after transfection.

Western Blot and Antibody Protocols

MCF7 cells were grown to subconfluence in the presence or absence of doxycycline for 72 hr in full media as described above. Cells were then treated in minimal DMEM (Sigma, D5030) containing 0.1% BSA, 1% L-glutamine, 2% Tet-Approved FBS, and 1 mM glucose for 16 hours followed by treatment with 2 ng/mL TGFβ (R&D Systems, 240-B-002) for 48 hours in the presence or absence of EGTA to examine sE-Cad expression levels, TAZ localization, and HER2 expression levels. Cells were washed with PBS and scraped from plates. Cytoplasmic and nuclear lysates were obtained using the Low/High Salt extraction method [50]. Cytoplasmic extracts were obtained by resuspending cells in NP40 containing Hypotonic Buffer (10 mM HEPES pH 7.4, 1.5 mM $MgCl_2$, 10 mM KCl, 0.5% NP40) followed by a 30 min incubation on ice and centrifugation. Nuclear extracts were obtained by resuspending the nuclear pellet in an equal volume of low salt buffer (10 mM HEPES, 25% glycerol, 1.5 mM $MgCl_2$, 20 mM KCl, 0.2 mM EDTA) followed by high salt buffer (10 mM HEPES, 25% glycerol, 1.5 mM $MgCl_2$, 800 mM KCl, 0.2 mM EDTA) followed by vortexing, 30 min incubation on ice, another vortex, and centrifugation. Samples were resolved on 4-12% Bis-Tris polyacrylamide gradient gels (Invitrogen) and transferred to PVDF membranes (Millipore). Membranes were probed with antibodies listed below followed by development with enhanced ECL (Millipore). Proteins were visualized using antibodies recognizing: E-Cadherin (Abcam, HECD-1, ab1416), YAP/TAZ (Cell Signaling, D24E4, #8418), FLAG antibody (from Dr. Chen-Yong Lin at Georgetown University, Washington D.C.), RUNX2 (Cell Signaling, D1L7F, #12556), HER2 (Santa Cruz, C-18, sc-284), ER-α (Santa Cruz, G-20, sc-544), N-Cadherin (Abcam, ab18203), Vimentin (Santa Cruz, V9, sc-6260), Histone H2A (Cell Signaling, #2578), β-actin (Sigma/Aldrich), GAPDH (Cell Signaling, 14C10,

2118), and YAP (Novus Biologicals). Protein levels were normalized to actin and quantified using NIH Image-J software.

Immunoprecipitation/Co-Immunoprecipitation Assay (IP/Co-IP)

Conditioned media was collected from MCF7 cells cultured in the presence (RUNX2 negative) or absence (RUNX2 positive) of doxycycline in minimal DMEM (Sigma, D5030) containing 0.1% BSA, 1% L-glutamine, 2% Tet-Approved FBS, and 1 mM glucose for 16 hours followed by treatment with 2 ng/mL TGFβ (R&D Systems, 240-B-002) for 48 hours. Conditioned Media was carefully removed from cells and remaining cellular debris was pelleted briefly by centrifugation. Conditioned Media protein levels were estimated using the Bradford assay. 200 µg of protein was suspended in 200 µL Co-IP buffer (50 mM Tris pH 7.5, 150 mM NaCl, 1 mM EDTA, 1 mM EGTA, 1% Triton X-100, 0.5% NP-40) and precleared in 20 µL of a 50% slurry of Protein G-Sepharose (GE Healthcare, 17-0618-01) for 30 minutes. Precleared supernatants were then incubated overnight with 0.5 µg of E-Cadherin antibody (Abcam, HECD-1, ab1416). Protein G-Sepharose was added for 1 hour and the precipitated complexes were washed with Co-IP buffer. Proteins were eluted from the beads using 0.1M Glycine buffer (pH 2.5), treated with 1×SDS loading buffer containing β-mercaptoethanol, and heated at 97° C. for 10 min. Samples were resolved on a 4-12% Bis-Tris polyacrylamide gel (Invitrogen) and transferred to PVDF membranes (Millipore). Immunoblots were probed for E-Cadherin (Abcam, HECD-1, ab1416) followed by development with enhanced ECL (Millipore).

To test for RUNX2 and TAZ protein interaction, nuclear lysates were obtained using NucBuster (Novagen) from MCF7 cells grown in full media or cultured in the presence (RUNX2 negative) or absence (RUNX2 positive) of doxycycline in minimal DMEM (Sigma, D5030) containing 0.1% BSA, 1% L-glutamine, 2% Tet-Approved FBS, and 1 mM glucose and 2 ng/mL TGFβ for 4 and 24 hours. Briefly, 400 µg of protein was resuspended in Co-IP buffer to a final volume of 200 µL. Lysates were precleared with 35 µL of a 50% slurry of Protein G-Sepharose (GE Healthcare) for 1 hr. Precleared nuclear lysates were then incubated with 4 µL of YAP/TAZ antibody (Cell Signaling) overnight. Protein G-Sepharose was added for 1 hour and the precipitated complexes were washed with Co-IP buffer. Proteins were eluted from the beads using 0.1M Glycine buffer (pH 2.5), treated with 1×SDS loading buffer containing β-mercaptoethanol, and heated at 97° C. for 10 min. Samples were resolved on a 4-12% Bis-Tris polyacrylamide gel (Invitrogen) and transferred to PVDF membranes (Millipore). Immunoblots were probed for RUNX2 (Cell Signaling, D1L7F, #12556), and YAP/TAZ (Cell Signaling, D24E4, #8418) followed by development with enhanced ECL (Millipore). To visualize the TAZ protein band a conformation specific rabbit secondary antibody was used (Cell Signaling, L27A9, #5127). Rabbit IgG and beads alone were used as Co-IP controls.

siRNA Mediated Knockdown of TAZ

TAZ knockdown was performed in MCF7 Tet.OFF cells using Custom 23mer desalted siRNA oligonucleotides from Sigma and a Universal Scrambled Negative Control siRNA Duplex from Origene (Catalog No. SR30004): TAZ siRNA #1: 5'-GACA UGAGAUCCAUCACUAUU-3' (SEQ ID NO: 1), TAZ siRNA #2: 5'-GGACAAACACCCAU GAACAUU-3' (SEQ ID NO: 2) and TAZ siRNA #3: 5'-AAGCCUAGCUCGUGGCGGAUU-3' (SEQ ID NO: 3). Briefly, MCF7 Tet.OFF cells were grown in the absence or presence of doxycycline for 3 days and then transfected with corresponding siRNA's using Lipofectamine-2000 (Life Technologies). RIPA extracts were obtained 48 hr post transfection and total protein was analyzed by Western blot (see above) and probed for TAZ protein expression. Protein levels were normalized to actin and quantified using NIH Image-J software.

To assay for sE-Cad levels, MCF7 Tet.OFF cells were grown in the absence or presence of doxycycline for 3 days and then transfected with TAZ siRNA #1 using Lipofectamine-2000. Cells were trypsinized, replated 24 hours later, and allowed to reattach. After 72 hours, nuclear and cytoplasmic extracts were obtained using the High/Low salt extraction method described above and analyzed for sE-Cad, TAZ, and RUNX2. Protein levels were normalized to actin and quantified using NIH Image-J software.

Drug Treatments with Compound 1

The compound 1 (MF=$C_{15}H_{13}Cl_2NO_3$) has a molecular weight of 326.175, a high Log P value of 3.25 (logarithm of its partition coefficient between n-octanol and water, a measure of the compound's hydrophilicity with low hydrophilicity=high Log P), a low Log SW of −4.35 (measure of aqueous solubility), three rotatable bonds, a hydrogen bonding donor/acceptor ratio of 2/3 (Hdon/Hacc), a polar surface area of 66.4 (tPSA; indicative of good cell membrane permeability), and an IC50 of 10 nM in D-ELISA DNA binding assays. MCF7 Tet.OFF cells were pretreated in the absence or presence of doxycycline for 3 days. RUNX2 transiently transfected T47D or HCC1428 breast cancer cells were grown in media that was then replaced with full media (as listed in the cell culture section) and treated with or without 50 µM compound 1. Cells were allowed to grow for 24, 48, and 72 hours. Nuclear and cytoplasmic extracts were obtained using High/Low salt extraction method and protein levels analyzed by Western blot (see above).

Attachment and Invasion Assay

Tissue culture plates were coated with Fibronectin (1 µg/ml), extracellular matrix (ECM; from endothelial cells cultured to confluence and treated with 5 mM EDTA to remove cells), or with confluent endothelial cells (human bone marrow endothelial cells). MCF7.Tet.OFF cells (RUNX2 negative and RUNX2 positive cultured in the presence (+Dox, RUNX2 negative) or absence (−Dox, RUNX2 positive) of doxycycline for 3 days) were added to the indicated plates for 120 min in D5030W media (Sigma) containing 0.1% FBS, 5 mM glucose, and 2 ng/ml TGFβ. The number of cells/field attached to Fibronectin, ECM, or endothelial monolayer was counted from 3-4 fields/well.

TCGA RUNX2 Protein Analysis

The Cancer Genome Atlas (TCGA) data was obtained from the online cbioportal (cbioportal.org/public-portal). The results shown represent protein expression and are based upon data generated by the TCGA Research Network (cancergenome.nih.gov). Briefly, cellular proteins were extracted and denatured in SDS sample buffer. After serial dilution of each sample, cell lysates were arrayed on nitrocellulose-coated slides and probed with specific RUNX2 and HRP-coupled antibodies to detect a signal by DAB colorimetric reaction. Spot densities were determined by MiroVigene, (automatic spot finding and background subtraction) and protein concentrations were determined by super curve fitting and normalized for protein loading.

DNA-Binding Enzyme-Linked Immunosorbent Assay (D-ELISA)

A microtiter plate-based D-ELISA was performed as described. Briefly, nuclear proteins were isolated from HBME-1 cells that express all three RUNX proteins and bound to double-stranded DNA oligonucleotides of human osteocalcin and MMP13 (forward primer: 5'-TTC TAC CAC AAA CCA CAC TCG TTC TAC CAC AAA CCA CAC TCG TTC TAC CAC AAA CCA CAC TCG-Biotin-3', SEQ ID NO: 4 and reverse primer: 5'-CGA GTG TGG TTT GTG GTA GAA CGA GTG TGG TTT GTG GTA GAA CGA GTG TGG TTT GTG GTA GAA-Biotin-3', SEQ ID NO: 5). Vehicle (0.05% DMSO) or compound 1 at different concentrations were incubated with the proteins and DNA oligonucleotide mixture in Avidin-coated 96-well plates. DNA-bound RUNX proteins were captured with specific antibodies (Cell Signaling Technologies). Primary and secondary antibody dilution was 1:500 and 1:10,000, respectively.

Chromatin Immunoprecipitation (ChIP) Assay

ChIP was performed using a kit (Cell Signaling Technologies) as per manufacturer's instructions. Briefly, cells were crosslinked with 1% formaldehyde and 1.5 mmol/L ethylene glycol bis[succinimidylsuccinate] at room temperature. Crosslinked chromatin was subsequently harvested, sheared, and precipitated with RUNX2 antibody or nonspecific IgG control (Cell Signaling Technologies). Precipitated DNA was treated with proteinase K, purified and processed for PCR, and amplified PCR products (99 bp) were visualized in 4% agarose gel. Fold enrichment of precipitated DNA over input chromatin was determined in triplicate by quantitative-PCR. PCR primers were designed to amplify regions on the MMP13 proximal promoter region adjacent to the TSS where the Runt binding element resides. Forward primer: 5'-GGT TTT GAG ACC CTG CTG AA-3', SEQ ID NO: 6 (−229 bp~−209 bp) and Reverse primer: 5'-CGT GGC GAC TTT TTC TTT TC-3', SEQ ID NO: 7, (−150 bp~−131 bp).

Cell Growth Assay

Cells were plated on 96-well (30,000 cells/well) or 24-well plates (50,000 cells/well). After CADD522 (0~100 µM) addition, cells were incubated for 24~72 hrs. Cells were stained with crystal violet (0.5% in Methanol:Acetic Acid=3:1) and washed with PBS. Crystal violet was solubilized in DMSO and measured in a microplate reader at 592 nm.

Cell Cycle Analysis

Cells ($1 \times 10^6$ cells/ml) were starved in serum-free medium for 24 hrs, and released in 10% serum-medium with or without compound 1 (50 µM) for 16~24 hrs for cell cycle transition. Cells were then fixed in 70% ethanol at 4° C. for 1 hr, resuspended in 1 ml PBS containing 20 µg/ml propidium iodide, 20 µg/ml RNase A, incubated for 30 min at room temperature, and analyzed with a Becton Dickinson LSR-II at the Flow Cytometry Core Laboratory at the University of Maryland. Ten thousand events per sample were collected and analyzed using the Cell-Quest (BD Biosciences).

Caspase 3/7 Assay

Cells were cultured in 96-well plates (30,000 cells/well). After compound 1 treatment for 24~72 hrs, cellular apoptosis was analyzed using the Caspase-Glo 3/7 Assay kit (Promega) according to the manufacturer's instructions.

Clonogenic Survival Assay

Cells were plated on 6-well plates (200~500 cells/well). After compound 1 (50 µM) treatment, cells were incubated for 2~3 weeks without changing media. Colonies were fixed in Methanol-Acetic Acid solution (3:1) and stained with crystal violet (0.5%). After washing, colonies were photographed and counted.

Anchorage-Independent Cell Growth Assay

Cells (10,000) were mixed in 1 ml of 0.3% low-melting agarose over a 0.6% agar bottom layer in normal growth media. The medium (600 µl) with or without compound 1 (50 µM) on soft agar was changed three times a week for 2~3 weeks. Images of MDA-231 and MCF7 were taken using Nikon Eclipse TE-2000S microscope with Zen Pro image software, and of MDA-468 using Olympus CKX41 microscope with Q-Capture Pro 7 image software at indicated magnifications under the same exposure settings for corresponding vehicle and drug treatments.

Tumorsphere Assay

Single cell suspensions (100,000 cells/well) were plated in 6-well ultra-low attachment plates (Corning) with 5 ml of EGM-2 supplemented with bullet kit (Lonza) and 2% FBS. compound 1 (50 µM) was added at the day of the plating or 4 days after plating. Tumorspheres were continuously photographed for 18 days and counted at the final day. Spheres were counted at 9 fields per well and averaged from triplicate.

Cell Invasion Assay

MCF7-tet-off cells were grown in the media with (+Doxy) or without doxycycline (−Dox) for 72 hours. Cells were then treated with compound 1 (50 µM) for 24 hrs, and trypsinized and suspended in serum-free media. Cells were re-plated in the top chamber precoated with 0.1×BME (Cultrex), and growth medium supplemented with 10% FBS was used as a chemoattractant in the bottom chamber. compound 1 was added to both chambers and incubated for 16 hrs. Cellular invasion was analyzed according to the 96 Well BME Cell Invasion Assay protocol (Cultrex).

Cell-Electrode Impedance Invasion Assay (xCELLigence System)

Real-time monitoring of cellular invasion was examined using an electrical impedance assay with an xCELLigence RTCA SP real-time cell-sensing device (Roche Applied Science). Matrigel (20 µl of 0.5 mg/ml) was pre-coated in the upper chamber of CIM plates and polymerized for 4 h and MDA-231 cells (75,000) were seeded onto wells containing growth medium with vehicle (0.1% DMSO) or compound 1 (50 µM). Impedance-based signals were measured every 5 minutes for 48 hrs according to the manufacturer's instructions. The invasive activity is expressed as the cell index (mean±SD) of duplicate wells. Three independent experiments were performed. In parallel, MDA-231 cells were plated onto wells with serum-free medium and the assay was performed.

Luciferase-Promoter Reporter Assays

Cells were plated in 96-well plates (30,000 cells/well) and incubated overnight. Cells were co-transfected with indicated luciferase-reporter plasmids (25 ng/well) and pSV-Renilla-Luc (Promega) (15 ng/well) for 6 hrs and compound 1 (0~100 mM) was further treated for 18~48 hrs. COX-2 (P2-274)-Luc (−170 bp~+104 bp) and control plasmids (PXP2-Luc) were kindly provided by Dr. Miguel A. Iñiguez (Universidad Autónoma de Madrid, Spain), and pNF-kb-Luc was from Dr. Hancai Dan (University of Maryland). Luciferase assay was performed using the Dual-Glo Luciferase Assay Systems as per manufacturer's recommendation (Promega).

Quantitative Real Time-RT-PCR (Q-RT-PCR)

Total RNA was extracted using TRIzol (Life Technologies). One µg of total RNA was reverse transcribed with oligo-(dT) primer using the SuperScript first-strand synthesis system (Invitrogen) to synthesize cDNA. One µl of each cDNA was used for real-time RT-PCR using QuantiFast SYBR Green PCR Kit (Promega). mRNA expression of gene of interest relative to β-actin was calculated based on the threshold cycle ($C_t$) as $2^-D(DCt)$ method. Primer sequences are listed in Table 1.

TABLE 1

Q-RT-PCR Primers

| | Forward (5'-3') | Reverse (5'-3') |
|---|---|---|
| RUNX1 | TGTCGGTCGAAGTGGAAGAGGGAA (SEQ ID NO: 8) | AGCTCCCGGGCTTGGTCTGA (SEQ ID NO: 9) |
| RUNX2 | TGCCTGCCTGGGGTCTGTA (SEQ ID NO: 10) | CGGGCCCTCCCTGAACTCT (SEQ ID NO: 11) |
| VEGF | CTTGCCTTGCTGCTCTAC (SEQ ID NO: 12) | TGGCTTGAAGATGTACTCG (SEQ ID NO: 13) |
| Glut-1 | CGGGCCAAGAGTGTGCTAAA (SEQ ID NO: 14) | TGACGATACCGGAGCCAATG (SEQ ID NO: 15) |
| LDHA | ATTCAGCCCGATTCCGTTAC (SEQ ID NO: 16) | GACACCAGCAACATTCATTCC (SEQ ID NO: 17) |
| SIRT6 | AAGTTCGACACCACCTTTGAGAGC (SEQ ID NO: 18) | ACGTACTGCGTCTTACACTTGGCA (SEQ ID NO: 19) |
| MT1-MMP | CTAAGACCTTGGGAGGAAAAC (SEQ ID NO: 20) | AAGCCCCATCCAAGGCTAACA (SEQ ID NO: 21) |
| MMP2 | CTTCTTCAAGGACCGGTTCAT (SEQ ID NO: 22) | GCTGGCTGAGTAGATCCAGTA (SEQ ID NO: 23) |
| MMP9 | GGGACGCAGACATCGTCATC (SEQ ID NO: 24) | TCGTCATCGTCGAAATGGGC (SEQ ID NO: 25) |
| MMP13 | TAACCGTATTGTTCGCGTCA (SEQ ID NO: 26) | TCCAGCCACGCATAGTCATA (SEQ ID NO: 27) |
| BSP | AAAGTGAGAACGGGGAACCTR (SEQ ID NO: 28) | GATGCAAAGCCAGAATGGAT (SEQ ID NO: 29) |
| OC | ACACTCCTCGCCCTATTG (SEQ ID NO: 30) | GATGTGGTCAGCCAACTC (SEQ ID NO: 31) |
| OPN | TTGCAGTGATTTGCTTTTGC (SEQ ID NO: 32) | GTCATGGCTTTCGTTGGACT (SEQ ID NO: 33) |
| β-actin | TGGCACCACACCTCTACAATGAGC (SEQ ID NO: 34) | GCACAGCTTCTCCTTAATGTCACGC (SEQ ID NO: 35) |

Western Blot Analysis

Whole cell lysates extracted in RIPA buffer (Upstate) were separated on 4-12% gradient SDS-PAGE and transferred to nitrocellulose membrane. The blots were incubated with specific antibodies for each protein overnight at 4° C. After antibody washing, the blots were reacted with their respective secondary antibody and detected with enhanced chemiluminescence reagents (Millipore) according to the supplier's protocol. Antibodies for proteins were purchased as below. RUNX1, RUNX2, CBF-β, ubiquitin and caspase-3 (Cell Signaling Technologies), S451-p-RUNX2 (Bioss Gentaur, Belgium), RUNX3 and Glut-1 (Millipore, Calif.), β-actin and RUNX2 antibody for IHC (Sigma-Aldrich), and Ki-67 for IHC (Bethyl Laboratories, Inc, TX).

Glucose Consumption and Lactate Production

For measurement of glucose level, cells (100,000/well) were plated in 24-well plates and incubated overnight. Cells were treated with compound 1 (50 μM) in phenol red-free growth medium and further incubated for 6 hrs or 24 hrs. The culture medium was collected and filtered through a 0.22 μm pore membrane. Glucose level in the medium was measured using Amplex Red Glucose/Glucose Oxidase Assay Kit (Invitrogen) as per manufacturer's instructions. For lactate level, cells were treated with compound 1 for 24 hrs, and the medium was washed and replaced with HEPES-buffered Krebs-Ringer solution (Boston BioProducts) supplemented with 10 mM Glucose. Cells were incubated for 30 min, and the medium was collected and filtered through a 0.22 μm pore membrane. Lactate level in the medium was measured using Lactate Assay Kit (Sigma-Aldrich) as per manufacturer's instructions. Cell growth assays using crystal violet staining were performed to verify equal number of cells and no significant difference was found in 24 hrs of compound 1 treatment (data not shown).

In Vivo Animal Studies and Immunohistochemical (IHC) Analysis

Animal maintenance and experimental protocols are in accordance with the guidelines of the University of Maryland's Institutional Animal Care and Use Committee. Results from the maximum tolerated dose (MTD) test performed prior to the in vivo study showed that doses of compound 1 up to 20 mg/kg mice for 2 weeks in athymic nude mice had no detectable influence on body weight or the general health of animals (data not shown).

For the MMTV polyoma middle T antigen (PyMT) mouse model, female mice were purchased from Jackson Laboratory. As mice developed first palpable mammary tumors after 5 weeks of age, mice were randomly assigned to 4 treatment groups at 6 weeks of age and received i.p. injections of compound 1 (1, 5 and 20 mg/kg/group) or equivalent volumes of vehicle (10% DMSO/90% PBS) (200 μl) twice a week. Palpable tumors were monitored every 1 to 2 days until 12 weeks of age to determine tumor incidence (number of tumors per mouse) and onset (the age of palpable tumors). Tumor weight was quantified at the final day after mice were euthanized and tumors were excised. Tumor volume [(length×width$^2$)/2] was measured by caliper.

For the PDX models, Br-001 tumor fragments derived from a patient with TNBC (University of Maryland, Translational Core Facility) were inoculated subcutaneously in female NOD scid gamma (NSG) mice (P1). After P1 tumors were grown, tumors were excised, fragmented and inoculated to a new group of NSG mice (P2). After P2 tumors were grown, they were excised, fragmented, and inoculated into nude mice (P3). When the size of the tumors reached 200~250 mm$^3$, mice were randomized into two groups, and received i.p. injection of vehicle or compound 1 (10 mg/kg) twice a week for 11 days.

To compare RUNX2 expression, protein lysates of normal mammary gland and mammary tumor samples were isolated from age-matched wild-type and MMTV-PyMT transgenic mice, respectively. Tumor tissues were dissected and processed for preparation of FFPE sections. After hematoxylin and eosin (H&E) staining was performed on each sample, IHC analysis was performed with specific antibodies recognizing RUNX2, Ki-67 (proliferation), caspase-3 (apoptosis), and Vector ABC kit (avidin-biotin-HRP) was used for detection.

For in vivo lung metastasis assay, MCF7-tet-off-Luc cells were grown for 3 days in the absence of Doxycyclin (−Doxy) and injected into the tail vein of the 8 week-old female NSG mice (1×10$^6$ cells/200 μl of PBS). After inoculation, the mice were randomly assigned to vehicle control and treatment groups. Vehicle (10% DMSO/90% PBS) and compound 1 (10 mg/kg) were injected i.p. 2 hrs after inoculation. The retention of the cells in the lung was monitored by noninvasive bioluminescence imaging for 24 hrs. For luciferase detection, 150 mg/mL D-luciferin (Caliper Life Sciences) in PBS was injected i.p. before imaging. Photometric measurement of metastasis was done by living Image software (Xenogen). In separate groups of mice, 231-Luc cells (1×10$^6$/200 μl of PBS) were injected, and the metastasis burden in the lung was quantified for 3 weeks.

Statistical Analysis

Results from cell culture assays were expressed as the mean±SD from at least three independent experiments. Comparisons of quantitative data between two groups were analyzed using the two-tailed Student's t-test. For in vivo study, data were expressed as the mean±SE. Multiple comparisons were followed by Mann-Whitney non parametrical tests. All statistical analyses were conducted using STATA version 14 (STATA Inc., College Station, Tex.). P values less than 0.05 were considered significant.

EXAMPLE 2

RUNX2 Inhibitor Compounds and Analogs

The lead compound 1, 3-(N-(3,4-Dichlorophenyl)Carbamoyl)-5-Norbornene-2-Carboxylic Acid (FIG. 1A) consists of a norbornene functional group (negatively charged carboxyl) coupled to a carbamoyl moiety with chlorine (Cl) atoms at position C-3 and C-4, (inhibitor of RUNX2 DNA binding, IC50 10 nM) was identified using the drug screen, Chembridge.com.

Ten 3D analogs (FIGS. 1B-1K) of compound 1 were similarly identified with structural identity between 72-97%. All drugs are small compounds (300-400 molecular weight), with high hydrophobicity (Log P >2.0), low solubility in water (Log SW <0), high flexibility (2-3 rotatable bonds), capable of hydrogen bonding (2-3 donor acceptor pairs; Hdon, Hacc), and low polar surface area (tPSA) for membrane permeability.

Figure 2A:
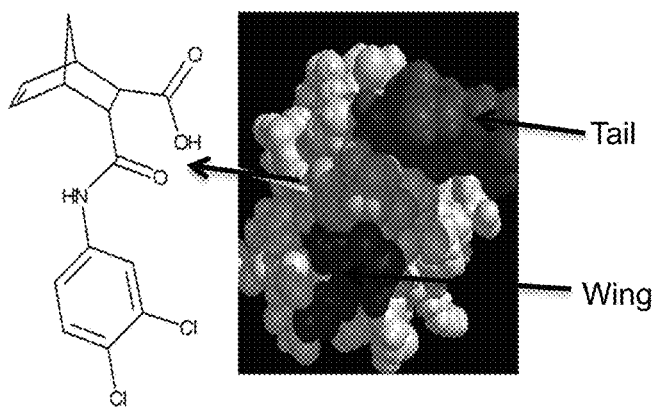
FIG. 2A shows that compound 1 (left) was identified from a computer-assisted drug design screen and validated in DNA binding assays to inhibit RUNX2 binding to its cognate DNA-binding domain It exhibits an IC50=10 nM in D-ELISA DNA binding assays. A best-fit model (right) predicts interaction with the tail, wing, and other adjacent residues of the Runx2 DNA-binding (Runt) domain.
Figure 2B:
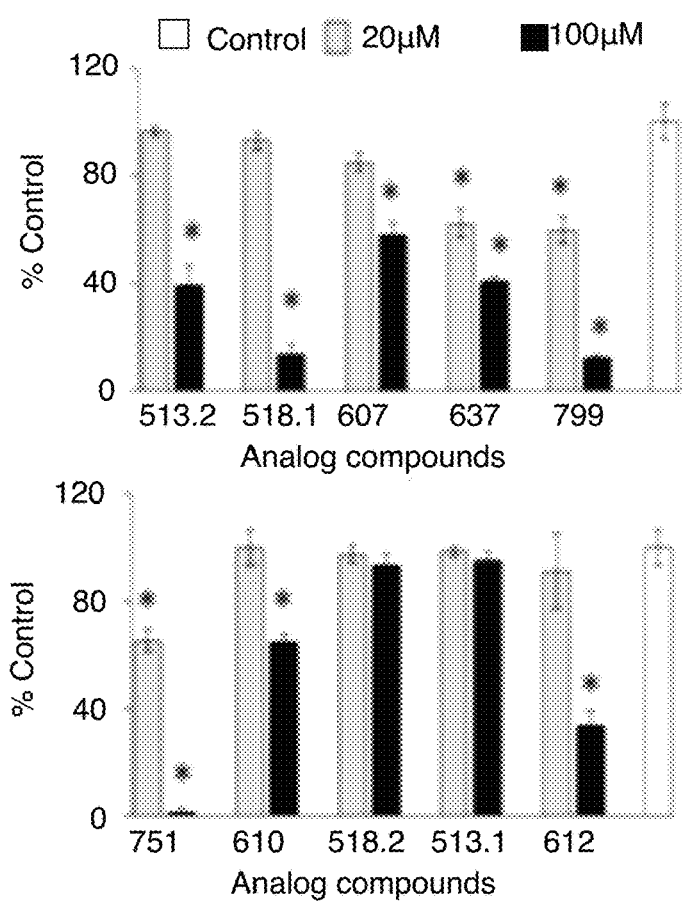
FIG. 2B shows inhibition of clonogenic growth by compound 1 analogs, compounds 2-10, to determine functional group specificity. Cells (500/well) were seeded in 6-well plates and grown in complete media appropriate for each cell. Treatment was with the analog compound (50 µM) for 2 weeks. Colony forming assays (CFA) were quantified at the end of the experiment with crystal violet (CV) staining and colony counts per high power field (n=3-6). Control cells treated with vehicle (Media+0.1% DMSO). Half maximal inhibition indicated (dotted line). Significant inhibition (p<0.05) observed for all cell lines tested.

Compound 1 was validated in DNA binding assays to inhibit RUNX2 binding to its cognate DNA-binding domain It exhibits an IC50=10 nM in D-ELISA DNA binding assays. A best-fit model predicts interaction with the tail, wing, and other adjacent residues of the Runx2 DNA-binding (Runt) domain (FIG. 2A). The analogs were tested for functional group specificity and biological activity. Most compounds (except compound 5 and compound 7) inhibited clonogenic growth (FIG. 2B). Compound 6 was very potent. Therefore, the C4-Cl or C4-Br group is essential for biological activity.

EXAMPLE 3

RUNX2 Activity in MCF7 Breast Cancer Cells

RUNX2 Protein Levels in Breast Cancer Patients

Figure 3A:
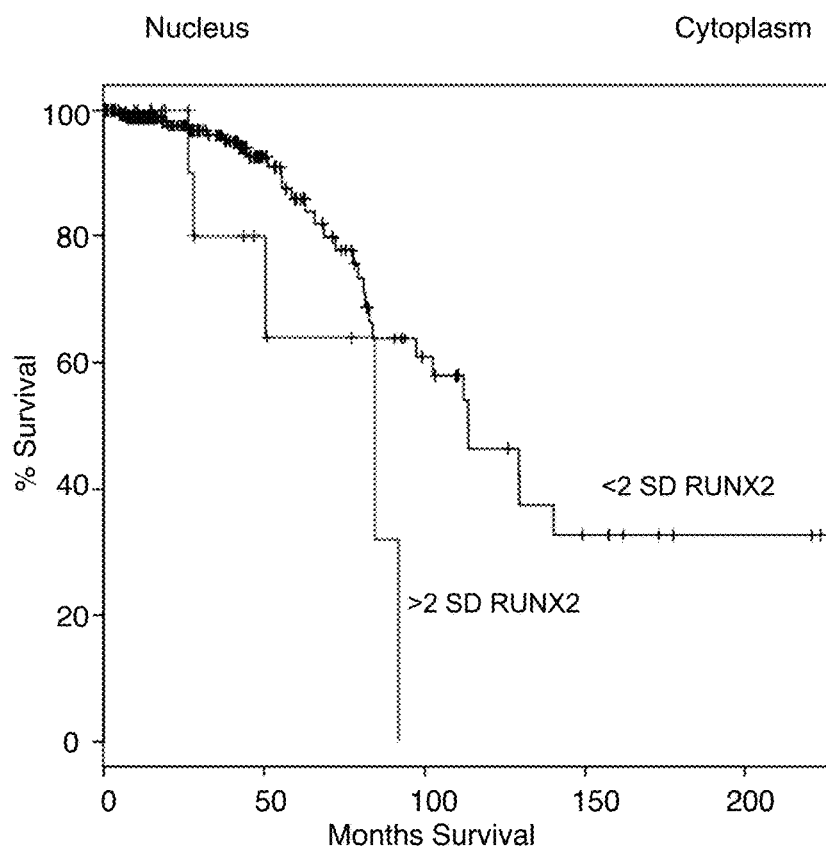
FIGS. 3A-3C depict RUNX2 expression in luminal breast cancers and anchorage independent growth. Upregulation of RUNX2 correlates with poor overall survival in patients with Luminal breast cancer. Cancer Genome Atlas (TCGA) results shown represent protein expression and are based upon data generated by the TCGA Research Network. Kaplan-Meier curves indicate % patients surviving (overall survival) as a function of months after diagnosis for patients with high RUNX2 protein expression (>2 SD) and patients with lower levels of RUNX2 protein (<2 SD).
Figure 18A:
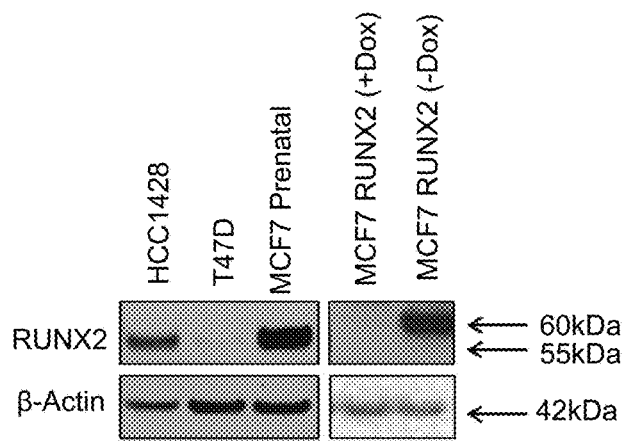
FIGS. 18A-18C illustrate RUNX2 expression in luminal breast cancer.

RUNX2 protein levels were examined in patients diagnosed with early stage luminal breast cancer (FIG. 3A). RUNX2 protein expression was associated with poor prognosis after diagnosis (overall survival; p=0.016) in those patients with high RUNX2 protein expression (>2 SD; median survival 80 months) compared to patients with lower levels of RUNX2 protein (<2 SD; median survival 117.5 months). To define models of luminal breast cancer, several cell lines were examined for RUNX2 expression. Variable levels of endogenous RUNX2 protein were detectable in luminal MCF7, HCC1428, and T47D breast cancer cells (see FIG. 18A).

Oncogenic Function of RUNX2

Figure 3B:
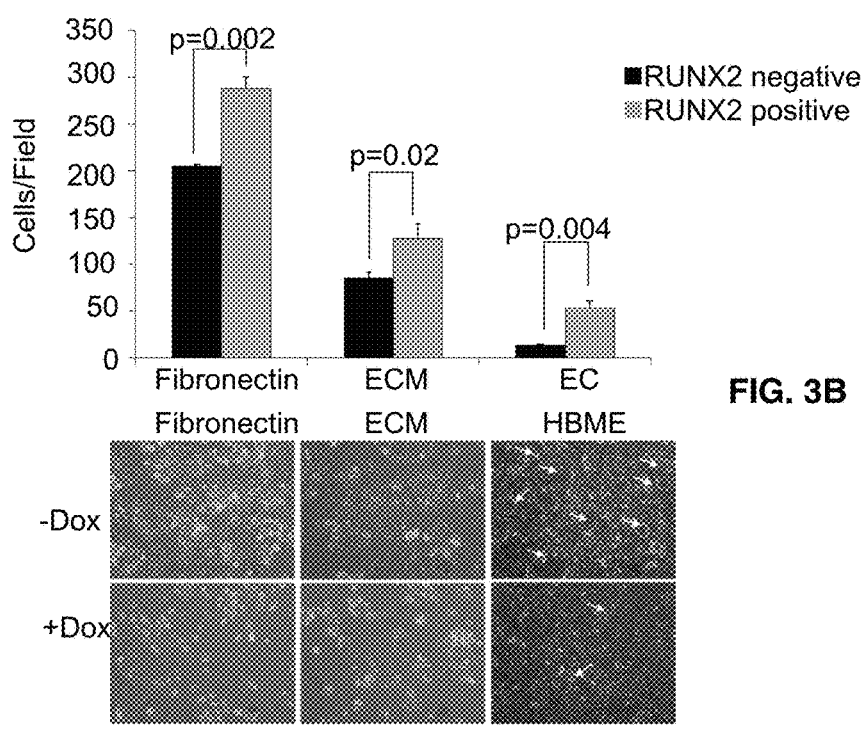
Figure 3C:
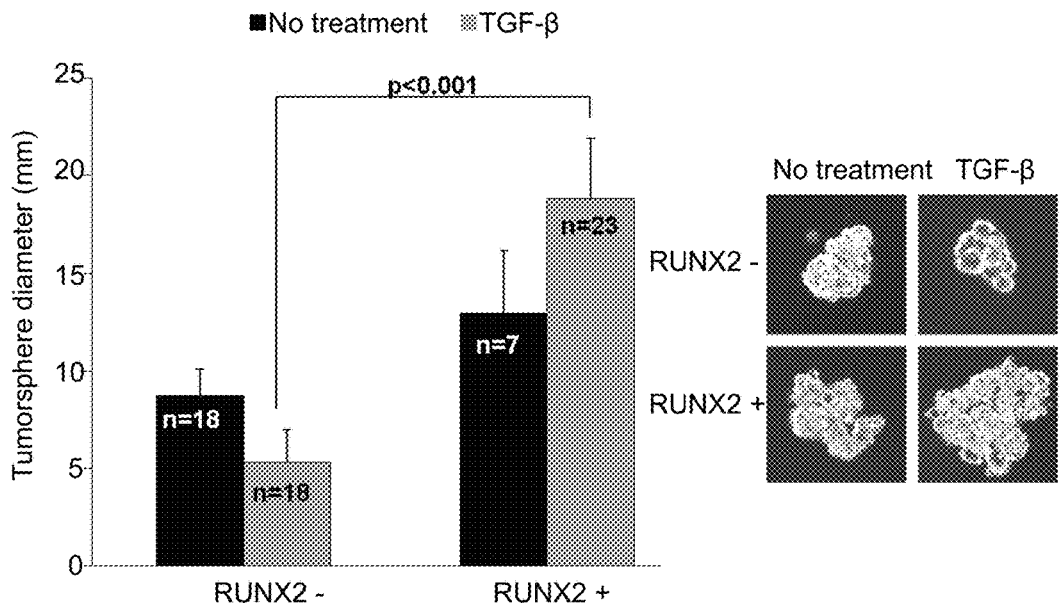

RUNX2 was expressed in the luminal breast cancer cell line, MCF7, under the control of a Tet.OFF promoter. RUNX2 expression increased attachment to extracellular matrix and fibronectin, and invasion through an endothelial cell monolayer (FIG. 3B). Culture of breast cancer cells in suspension as a model of anchorage-independent growth defines a transformed breast cancer cell phenotype (tumorspheres). Inducible RUNX2 expression in MCF7 cells resulted in tumorspheres that were significantly larger (3.6-fold; p<0.001) than MCF7 cells in which RUNX2 expression was repressed, especially in the presence of TGFβ (FIG. 3C).

EXAMPLE 4

Compound 1 Suppresses In Vitro Breast Cancer (BC) Cell Growth and Survival

Figure 4A:
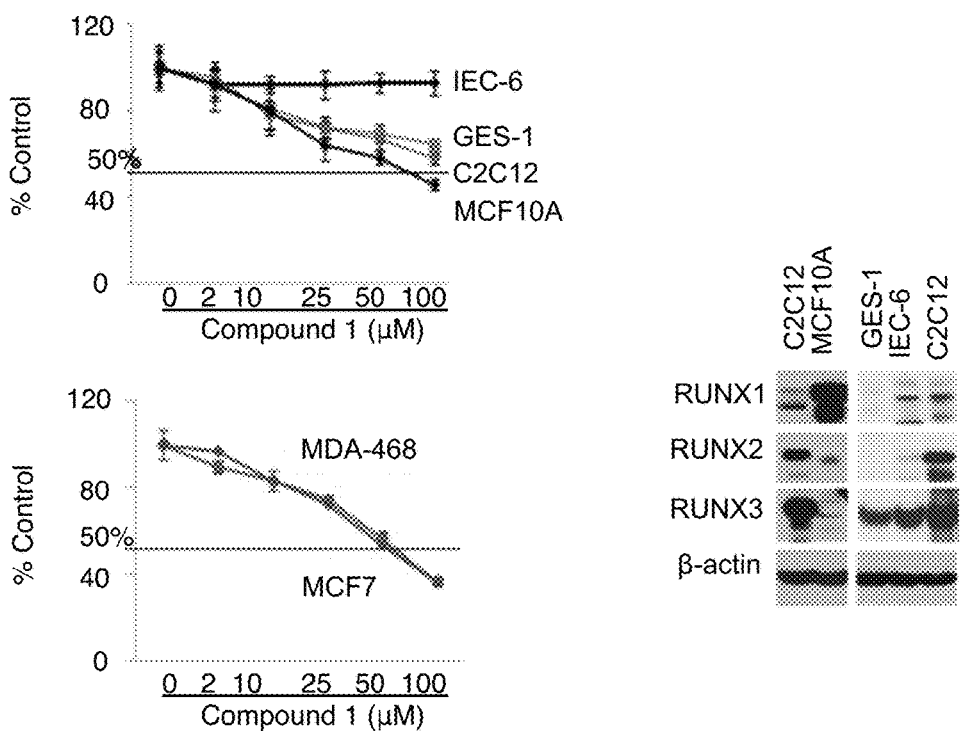
FIGS. 4A-4D illustrates the results of compound 1 on cell growth of breast cancer cells.
Figure 4B:
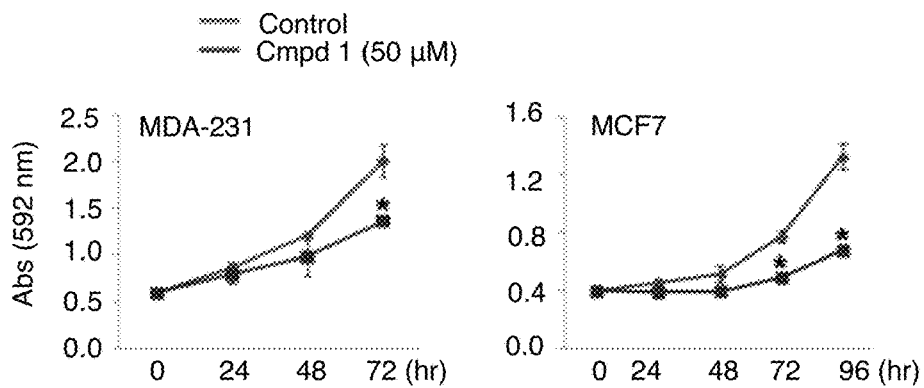

To determine the effect of compound 1 on cell viability and growth, breast cancer cells (MDA-MB-468, and MCF7) as well as non-malignant cells (MCF10A untransformed human mammary epithelial cells, IEC-6 undifferentiated rat intestinal cells, and GES-1 human gastric mucosal cells, and C2C12 murine myoblast cells) were treated with compound 1 (0~100 μM) for 24~72 hrs. There was no significant inhibition in cell viability over 24 hrs (data not shown), while compound 1 displayed a dose- and time-dependent cell growth inhibition over 72 hrs (FIGS. 4A-4B). However, the sensitivity of non-malignant cells to compound 1 was much lower than that of BC cell lines, indicating that compound 1 might not exhibit serious cytotoxicity for normal cell growth.

Figure 4C:
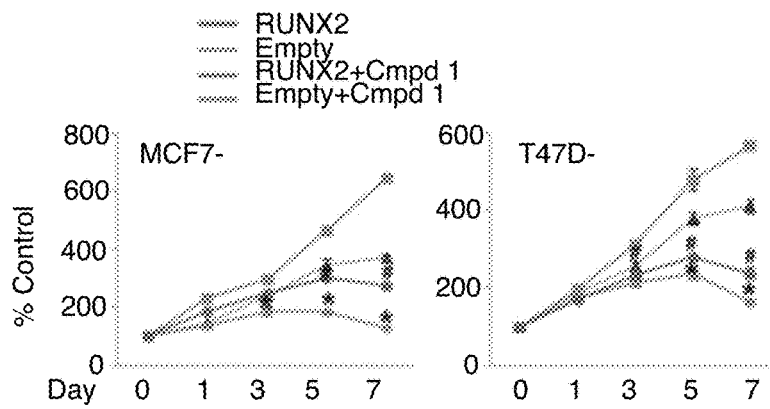
Figure 4D:
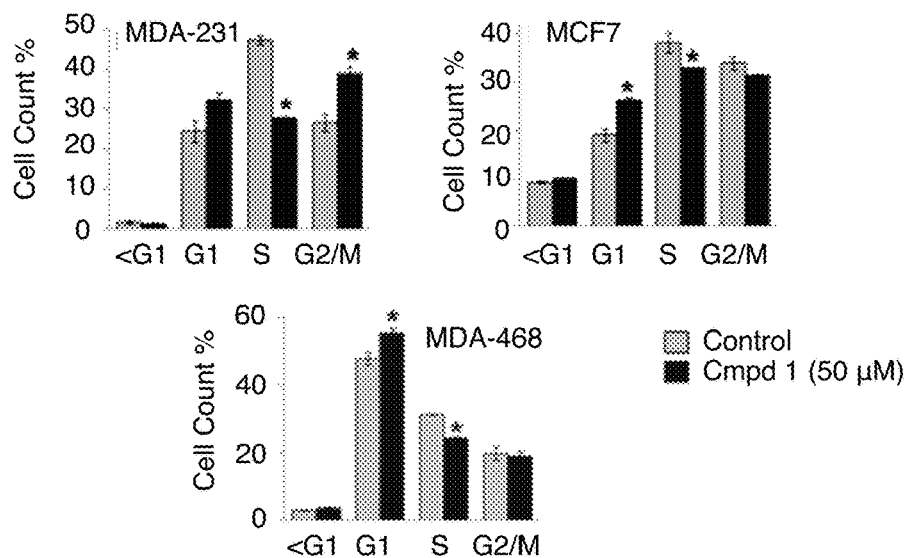
Figure 5A:
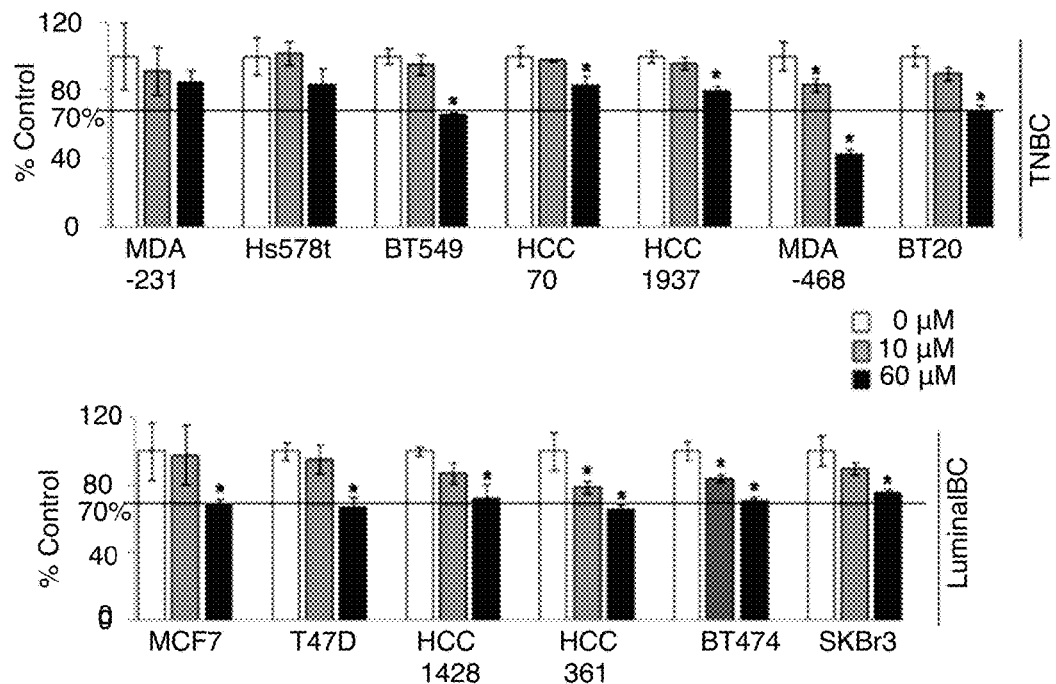
FIGS. 5A-5C illustrate the effect of compound 1 on the breast cancer cell growth and apoptosis.
Figure 5B:
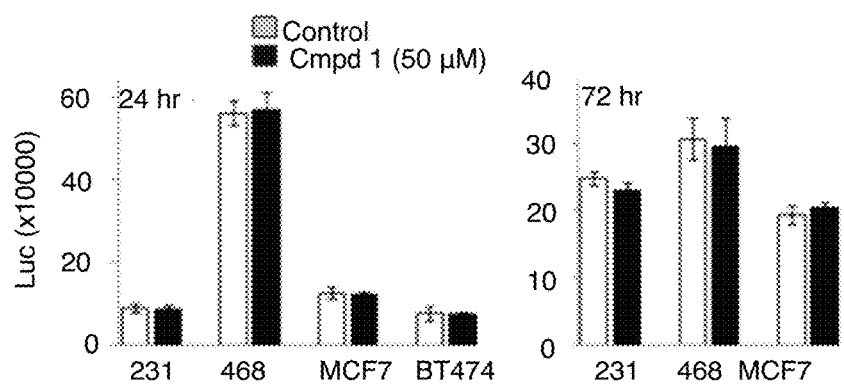
Figure 5C:
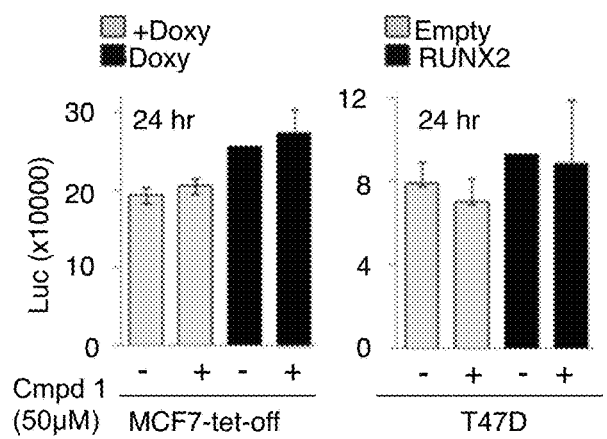

When ectopic RUNX2-expressing MCF7 and T47D cells were treated with compound 1 for 7 days, a dramatic decrease in cell proliferation relative to vehicle controls FIG. 4C was observed. Next, the growth inhibitory effect of compound 1 on other BC cell lines was examined. As shown in FIG. 5A, compound 1 at 50 µM for 72 hrs exerted mild but significant growth inhibition (<50%) in the majority of TNBC and luminal type BC cells. Among them, MDA-MB-468 (MDA-468) cells were most sensitive to compound 1 (>50%). Moreover, compound 1 at 50 µM within 72 hrs displayed no apoptotic cell death or necrosis under microscopic observations, no increase in the levels of cleaved caspase-3/7 expression (data not shown), and no change in caspase-3/7 activity compared to vehicle controls (FIGS. 5B-5C). However, compound 1 treatment increased cell populations at the G1 phase with reduction at the S phase (FIG. 4D) indicating that the anti-proliferative effect of compound 1 might be associated with cell cycle arrest.

Figure 6A:
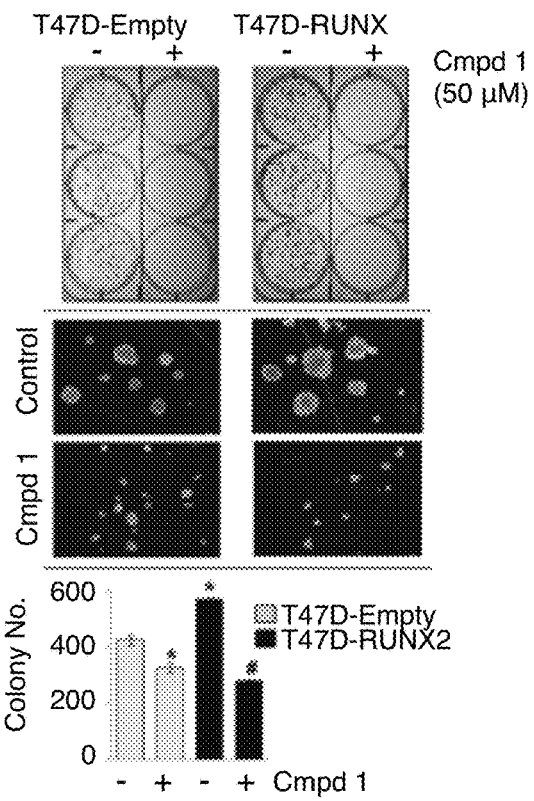
FIGS. 6A-6F illustrates that compound 1 diminishes clonogenic survival of breast cancer cells.
Figure 6B:
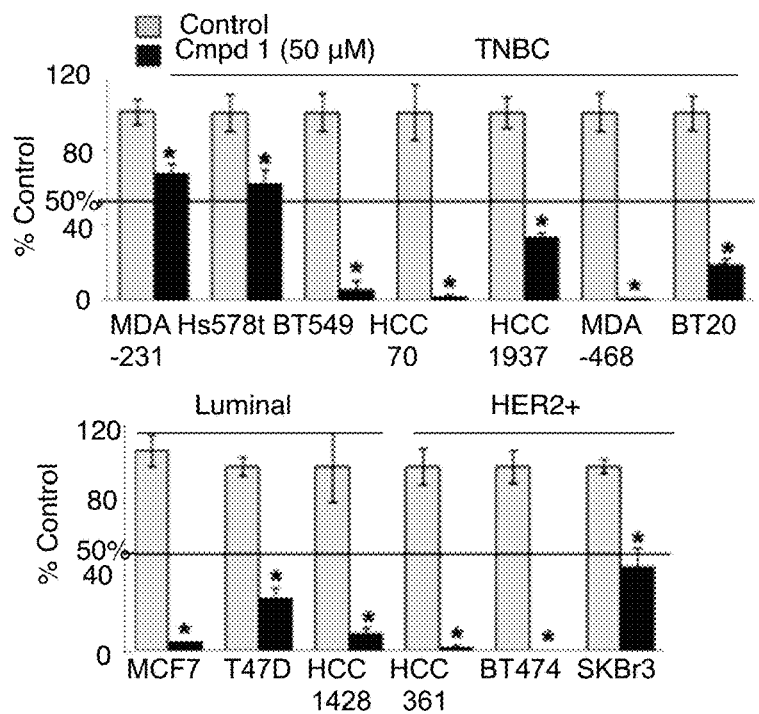
Figure 6C:
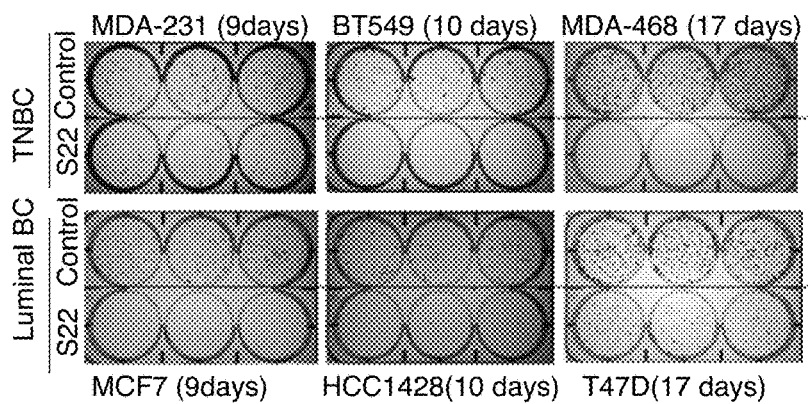
Figure 6D:
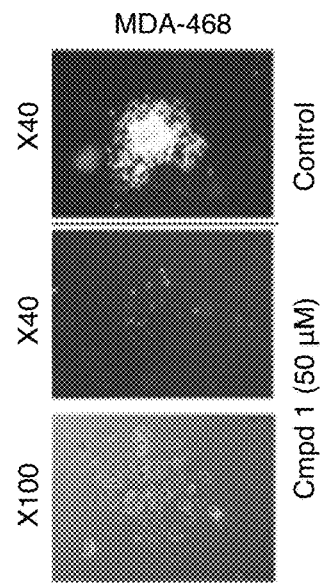
Figure 7A:
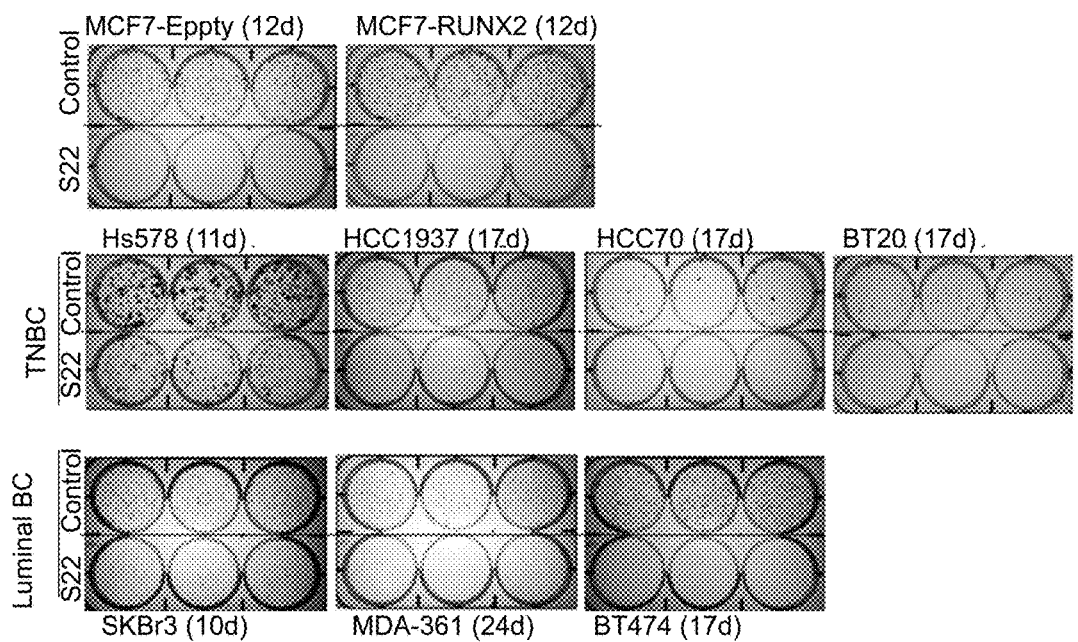
FIGS. 7A-7B show the results of a clonogenic assay and anchorage-independent growth assay.

The effect of compound 1 on long term cell survival was further investigated in BC cells in the presence or absence of compound 1 (50 µM) for 2~3 weeks. As shown in FIG. 6A, expression of RUNX2 in T47D cells enhanced the growth of colonies (both size and number) compared to Empty vector controls, but compound 1 dramatically diminished the clonogenicity of both T47D-Empty and T47D-RUNX2 cells. The suppression was slightly greater in T47D-RUNX2 cells than in Empty controls. The RUNX2-mediated increase in colony formation was also suppressed by compound 1 in ectopic RUNX2-expressing MCF7 cells (FIG. 7A). In addition, reduced clonogenicity was observed in compound 1-treated BC cells (11 out of 13 cells) that showed less than 50% survival after compound 1 treatment (FIG. 6B). In particular, less than 10% cell survival was observed in six cell lines (BT549, HCC70, MDA-468, MCF7, HCC361, and BT474), indicating that the growth inhibitory effect of compound 1 was not restricted to specific BC cell type. Microscopic images revealed that colonies in the compound-treated cells were sparse, disintegrated, and smaller than in the vehicle controls that were compact and well-integrated (FIGS. 6C-6D).

Figure 6E:
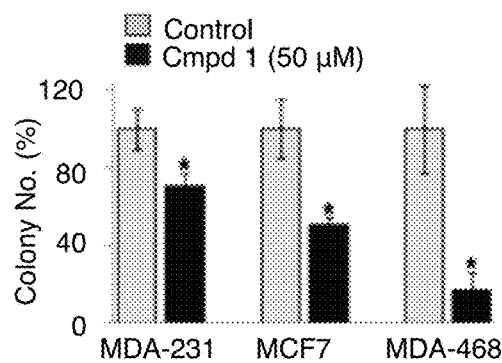
Figure 6F:
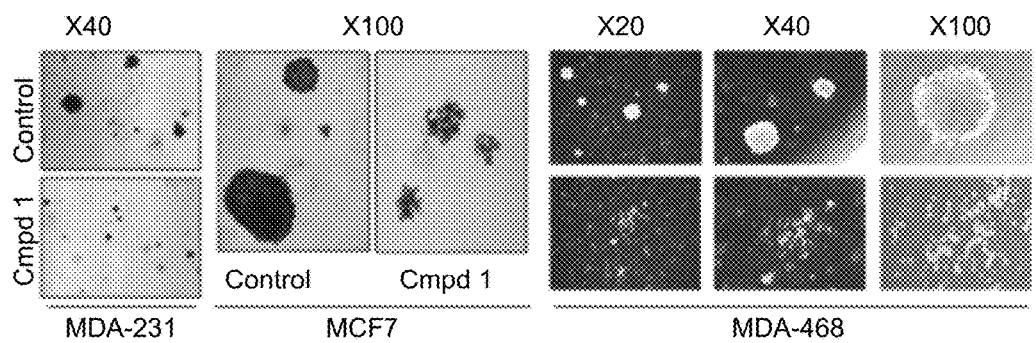
Figure 7B:
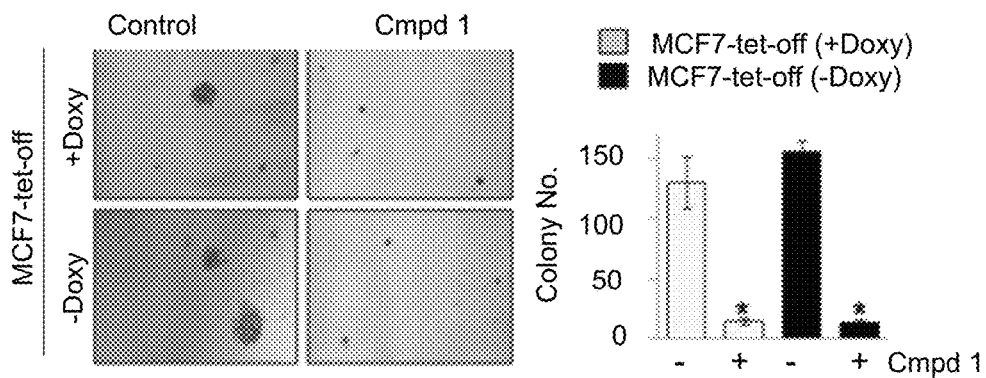

Moreover, compound 1 strongly inhibited anchorage-independent cell growth of BC cells (FIG. 6E); colonies of the compound 1-treated MDA-MB-231 (MDA-231), MCF7 and MDA-468 cells were highly disrupted, segregated and apoptotic, whereas those of vehicle controls were compact, tight and healthy (FIG. 6F). The size of colonies also was much smaller in the compound 1-treated cells than in the control (<1/10 in size). Similar results were observed for compound 1-treated MCF7-tet-off cells in which compound 1 treatment resulted in reduced colony formation (FIG. 7B). The colony number also was not significantly different in the MCF7-tet-off (+Doxy) and MCF7-tet-off (−Doxy) cells expressing ectopic RUNX2. Taken together, these results indicate that compound 1 has a strong inhibitory effect on BC cell growth and survival.

EXAMPLE 5

Figure 8:
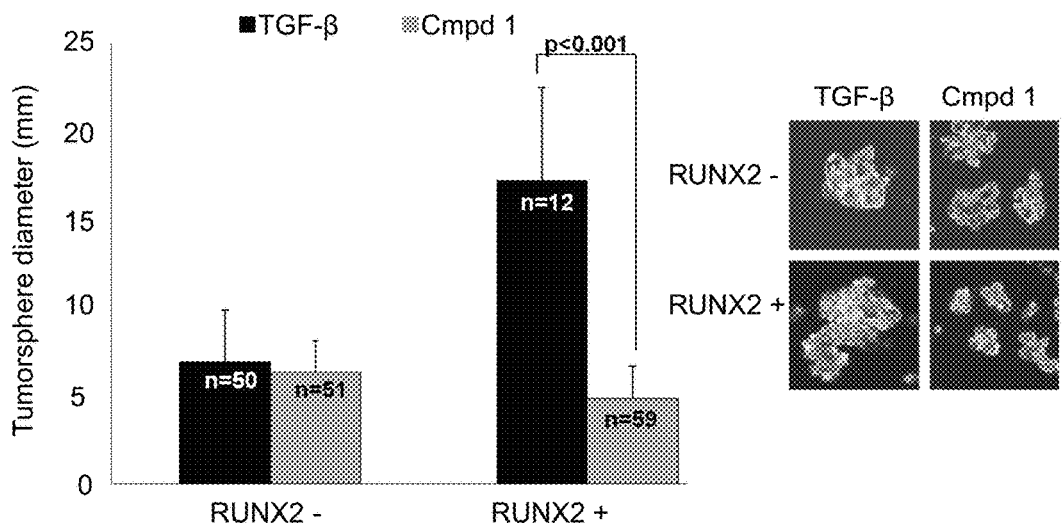
FIG. 8 shows the tumorsphere diameter of MCF7 RUNX2 Tet.OFF cells that were cultured in suspension for 12 days with (gray bar) or without (black bar) 50 µM compound 1. Representative photos of colonies are shown.

Compound 1 Inhibits Tumorsphere Formation and In Vitro Invasion of Breast Cancer (BC) Cells
Tumorsphere Growth is RUNX2 Dependent Compound 1 was used to treat MCF7 cells in suspension. Compound 1 significantly decreased the diameter of RUNX2 positive MCF7 tumorspheres (17.21±5.28 to 4.83±1.87; p<0.001), an almost 4-fold inhibition relative to vehicle-treated cells (FIG. 8). RUNX2 negative cells were unaffected (6.98±2.89 to 6.37±1.78; p=0.209). RUNX2 is necessary for luminal breast cancer cell tumorsphere formation.

Compound 1 Reduces Tumorsphere Size and Number

Figure 9A:
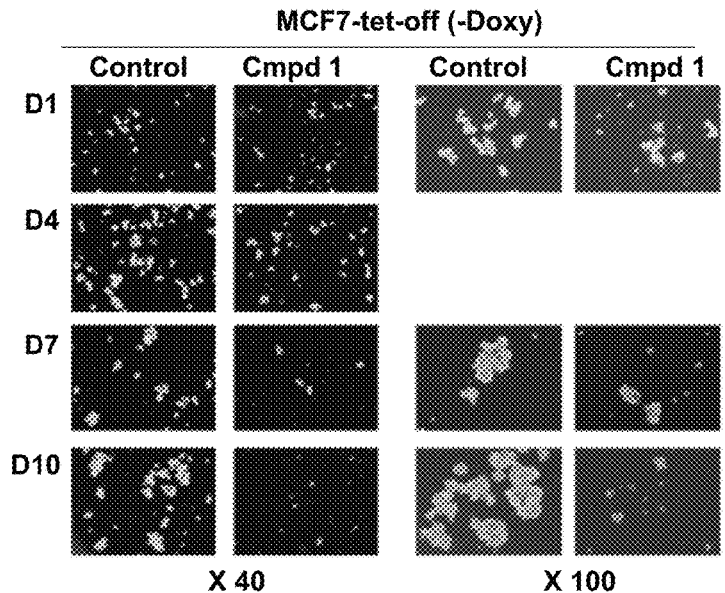
Figure 9F:
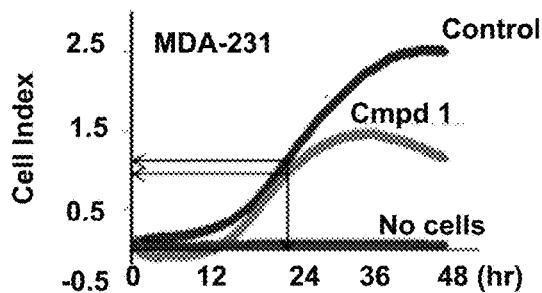

Even without TGF-β, MCF7-tet-off (−Doxy) cells (FIG. 9A) as well as MDA-231, MDA-468 and MCF7 cells (FIG. 9B) formed tumorspheres over 7~10 days. However, compound 1 dramatically decreased the size as well as the number of tumorspheres FIG. 9C. Tumorspheres were severely disrupted a few days after compound 1 treatment at the initial day of cell plating or even when cells were treated with compound 1 at day 4 (D4+) after tight tumorspheres had already formed (FIG. 9D). Importantly, treatment with compound 1 did not have a significant influence on mammosphere formation of the MCF10A non-malignant mammary epithelial cells (data not shown). These results suggest a relatively selective effect of compound 1 on BC cells.
Compound 1 Reduces Breast Cancer Cell Invasiveness To investigate if compound 1 impairs the invasive phenotype of the BC cells, in vitro cell invasion assays in 3D-culture were performed using both 96-well basement membrane extract (BME) cell invasion assay and xCELLigence System (the cell-electrode impedance invasion assay). The MCF7-tet-off (+Doxy) and -off (−Doxy) cells were plated on BME-coated wells and incubated in the presence or absence of compound 1 for 24 hrs. Cellular invasion was promoted by RUNX2 induced by removal of Doxycycline (−Doxy). However, compound 1 almost abrogated the invasiveness of both MCF7-tet-off (+Doxy) and MCF7-tet-off (−Doxy) cells (FIG. 9E, left). Substantial inhibition of the invasive behavior of MDA-231 cells by compound 1 also was observed in the xCELLigence System that monitors cellular events in real time (FIG. 3F). The cell index of the untreated control was 2.3675±0.1214 (mean±SD), and for the cells treated with compound 1 for 48 hrs 1.6636±0.1845 (P=0.0456), respectively. Importantly, compound 1 had little effect on the viability of MCF7-tet-off or MDA-231 cells over 24 hrs (FIG. 9E, right), indicating that compound 1 reduces BC cell invasiveness without cellular toxicity.

EXAMPLE 6

Figure 10A:
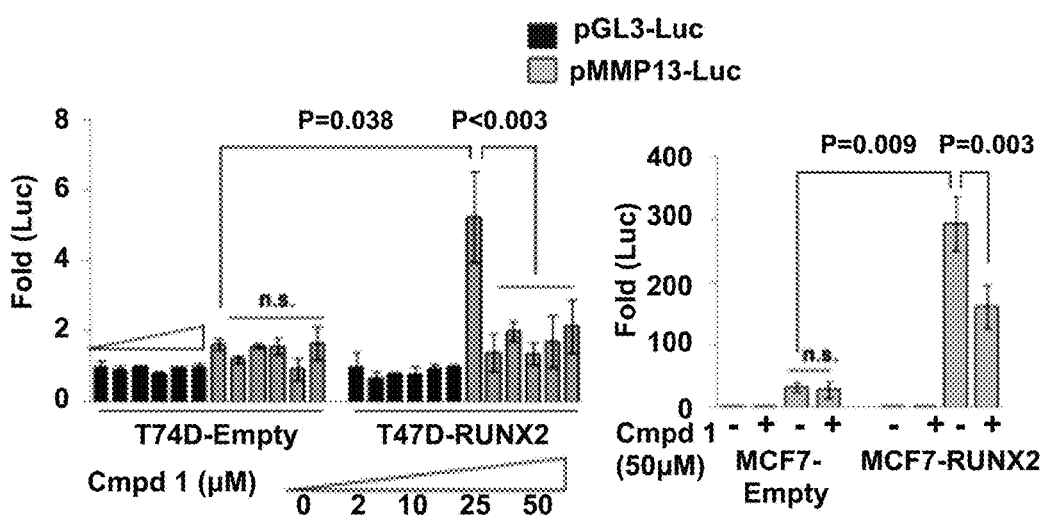
FIGS. 10A-10C show that compound 1 decreases RUNX2 transcriptional activity.
Figure 10B:
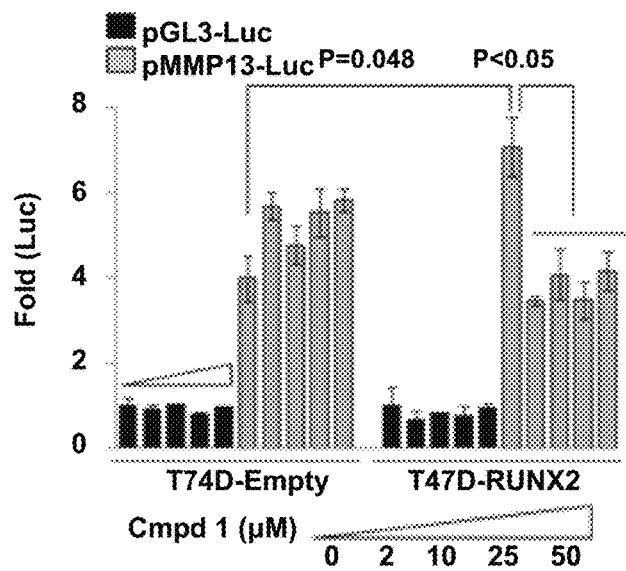
Figure 11A:
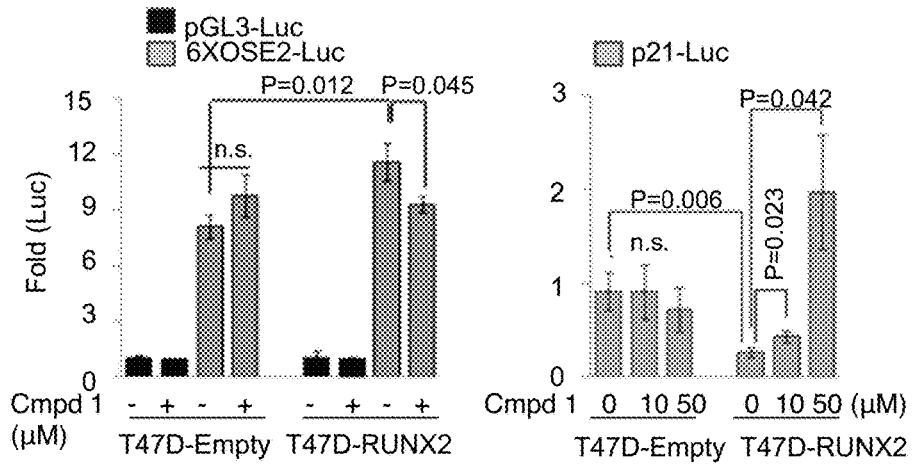
FIGS. 11A-11B illustrate the effect of compound 1 on activities of non-RUNX family transcription factors.

Compound 1 Inhibits RUNX2 Transcriptional Activity
Inhibition of Activity in RUNX2 Expressing Breast Cancer Cells Compound 1 treatment of ectopic RUNX2-expressing BC cells (T47D-RUNX2 and MCF7-RUNX2) resulted in a dramatic decrease of the promoter-luciferase (Luc) activities of RUNX2 downstream target genes such as MMP13 and VEGF (metastasis markers) (FIGS. 10A-10B) and OC (osteogenesis marker) (FIG. 11A). compound 1 had little effect on the activities of control cells that were stimulated without RUNX2 (T47D-Empty and MCF7-Empty). The inhibition of the promoter-Luc activities of MMP13 in T47D-RUNX2 cells was almost completely blocked by compound 1 at 2 µM, the lowest concentration tested (FIG. 10A, left). In particular, the MMP13 promoter-Luc activity of MCF7-RUNX2 cells was about 300-fold higher than pGL3-Luc activity, which was 10-fold higher than MCF7-Empty cells, but compound 1 repressed about 50% of the MMP13 promoter-Luc activity of MCF7-RUNX2 cells (FIG. 10A, right). The p6×OSE2-Luc activity was mildly increased in T47D-RUNX2 cells compared to T47D-Empty cells, but the activity was slightly but significantly reduced by compound 1 (FIG. 11A, left). On the contrary, RUNX2 expression in T47D was associated with about 4-fold lower promoter-Luc activity of the cyclin-dependent kinase inhibitor p21 (Cip1) compared to Empty cells, but compound 1 reactivated the RUNX2-repressed p21 promoter activity. These results indicate that compound 1 negatively regulates transcription of RUNX2 target genes.

Figure 10C:
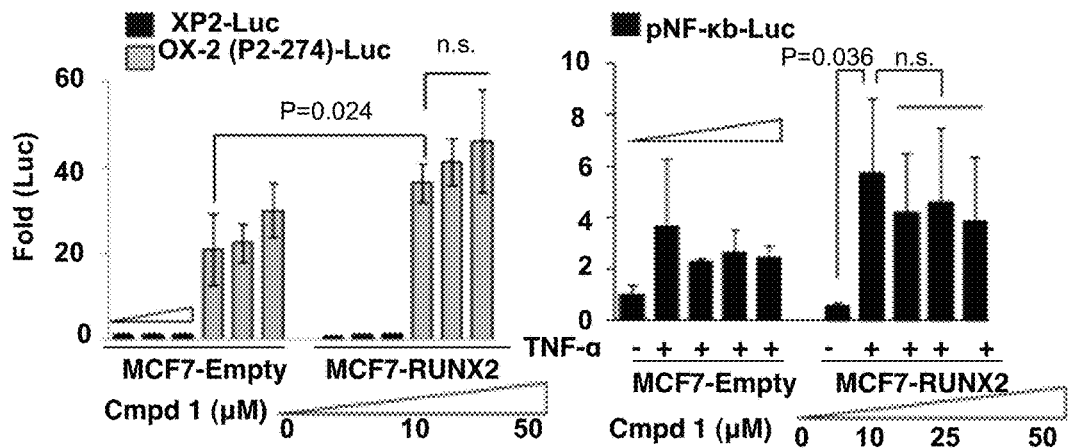
Figure 11B:
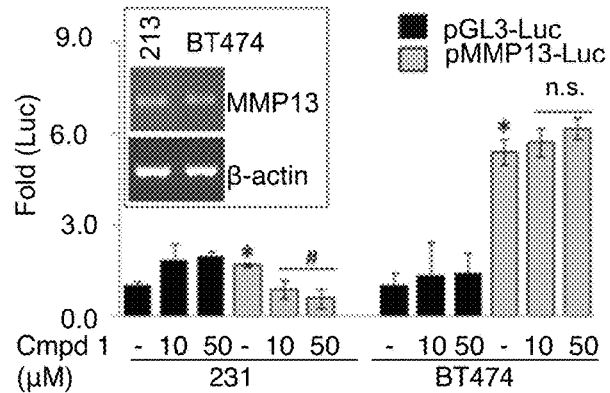

To determine if compound 1 could inhibit transcriptional activities of other transcription factors that do not belong to the RUNX family, the gene reporter analysis was performed with COX-2 and NF-κb promoter constructs without Runt binding sequences. The activity of the COX-2 P2-274-Luc showed 2-fold increase in MCF7-RUNX2 cells compared to MCF7-Empty cells, which might be through indirect action of RUNX2 (FIG. 10C, left), but the activity of pNF-κb-Luc Luc did not show significant increase (FIG. 10C, right). Notably, compound 1 had no inhibitory effect on either COX-2 (P2-274)-Luc or pNF-Kb-Luc promoter activities, indicating specific inhibition of Runt binding site-mediated transcription by compound 1. In addition, compound 1 did not attenuate the MMP13 promoter activity in BT474 cells that do not express RUNX2 (FIG. 11B), whereas it decreased significantly the activity in MDA-231 cells that express RUNX2, suggesting the potential specificity of compound 1 for RUNX2.

Compound 1 Inhibits RUNX2-DNA Binding

Figure 12A:
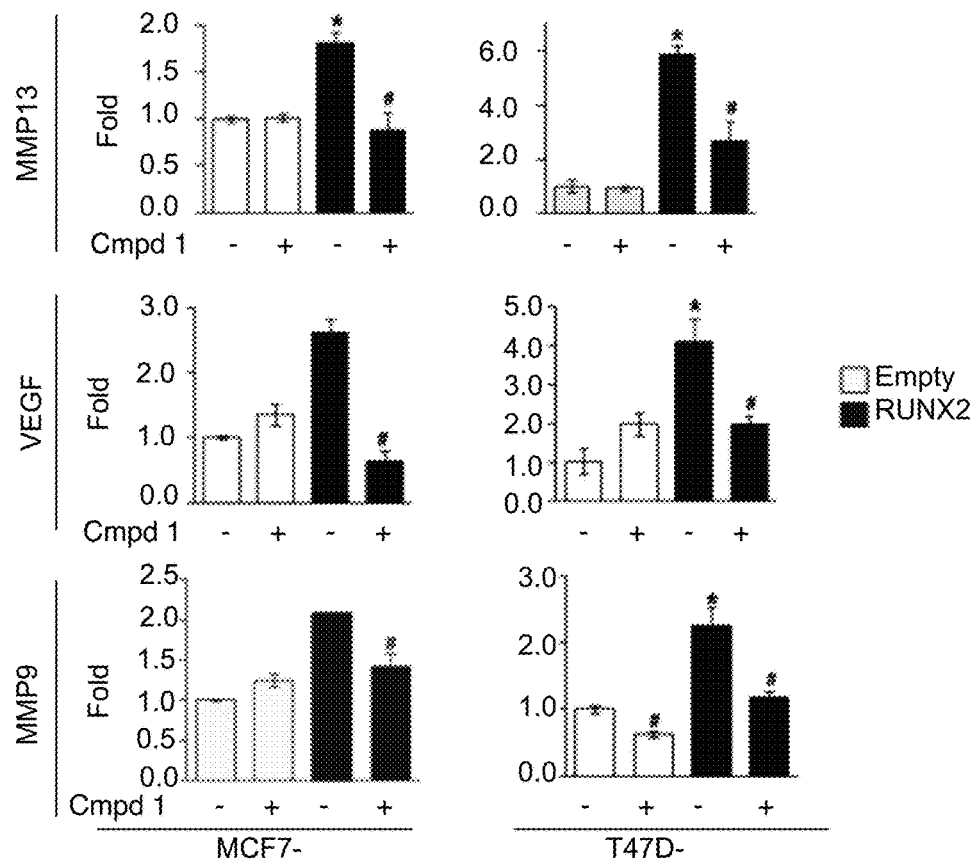
FIGS. 12A-12B show that compound 1 inhibits transcription of RUNX2 responsive genes.
Figure 12B:
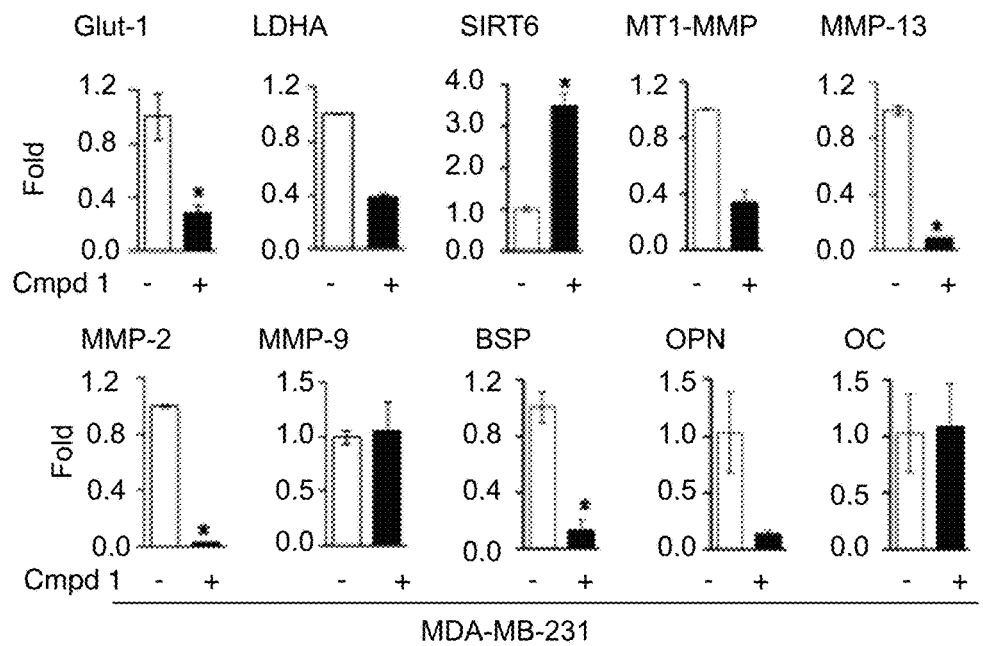
Figure 13A:
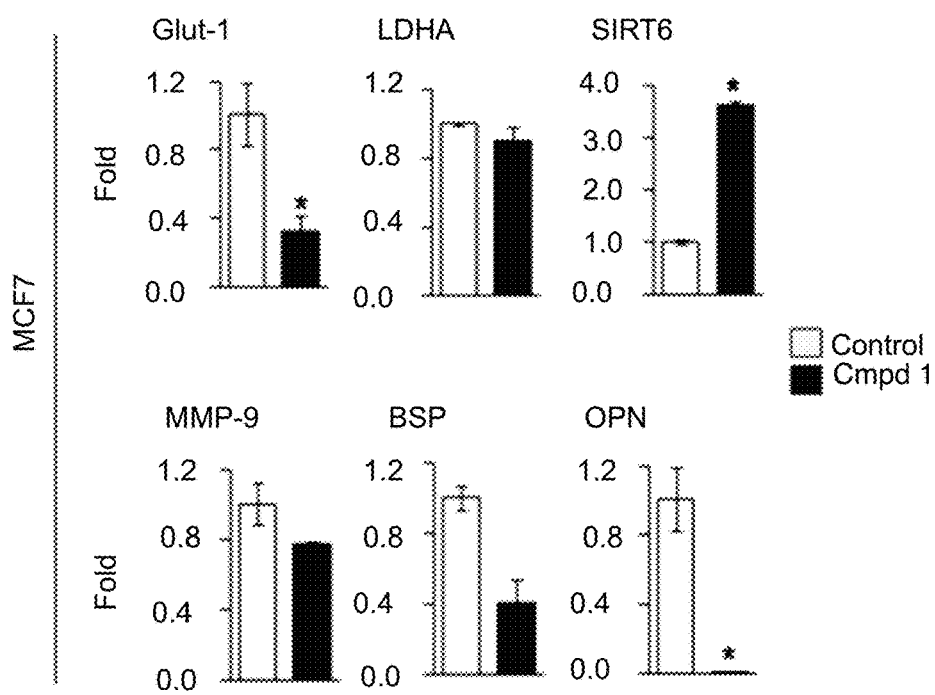
FIGS. 13A-13C show the Q-RT-PCR analyses of RUNX2 target genes in MCF7 (FIG. 13A) and MDA-468 cells (FIG. 13B). Cells were treated with or without compound 1 (50 μM) for 6 hrs.
Figure 13B:
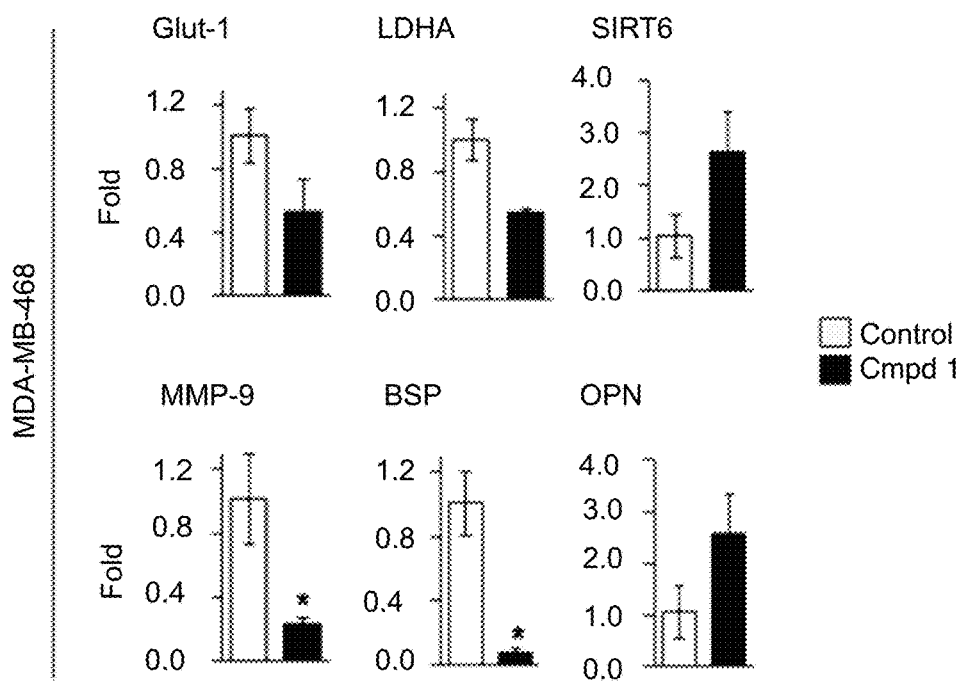

Consistent with these observations, compound 1 modulated the mRNA levels of RUNX2 responsive genes such as Glut-1, LDHA, and Sirt6 that regulate glucose metabolism, MMP-2, MMP-9, MMP13 and MT1-MMP that regulate tumor invasion/metastasis, and BSP, OPN and OC that regulate osteogenic differentiation. As shown in FIG. 12A, compound 1 repressed the mRNA expression levels of MMP13, VEGF, and MMP9 that were upregulated in the ectopic RUNX2-expressing MCF7 and T47D cells. In MDA-231 cells, compound 1 reduced the transcriptional levels of Glut-1 and LDHA but increased the level of Sirt6 (FIG. 12B), which was consistent with RUNX2 positively regulating Glut-1 and LDHA, but negatively regulating Sirt6 expression in glucose metabolism. Similar results were observed in MCF7 (FIG. 13A) and MDA-468 cells (FIG. 13B). These combined results suggest that compound 1 exerts its inhibitory function on the expression of RUNX2 target genes by inhibiting RUNX2-DNA binding.

Compound 1 and Inhibition of Glut-1 Expression in Breast Cancer Cells

Figure 13C:
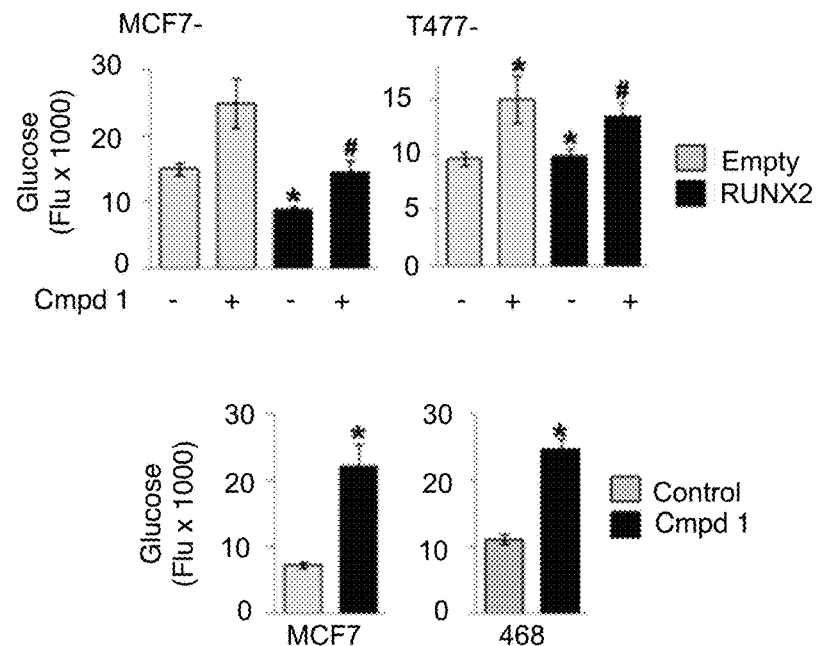
Figure 14A:
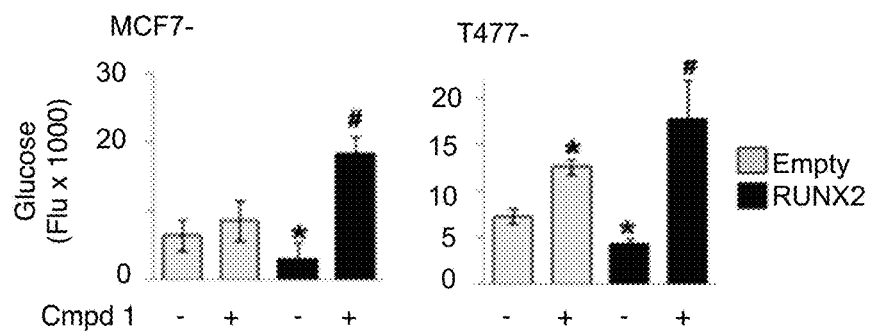
Figures 14B, 14C:
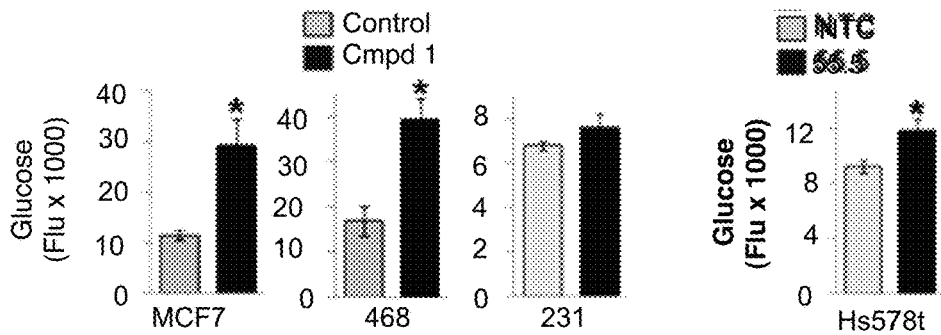
Figure 14D:
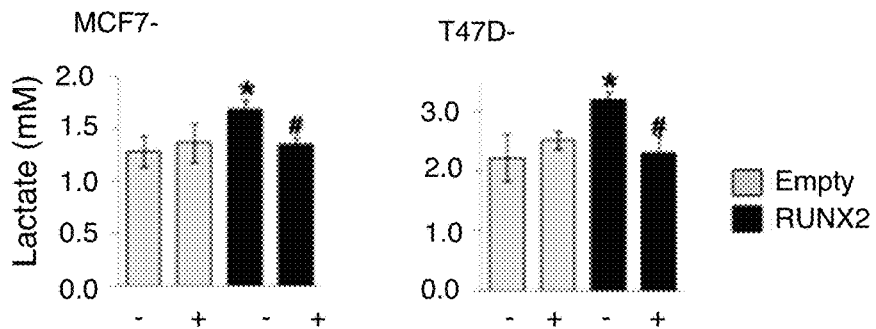
Figure 14G:
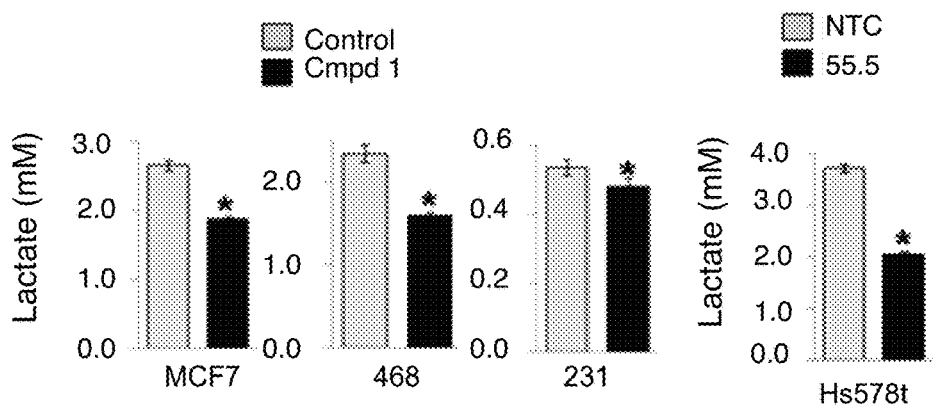
Figure 14G:
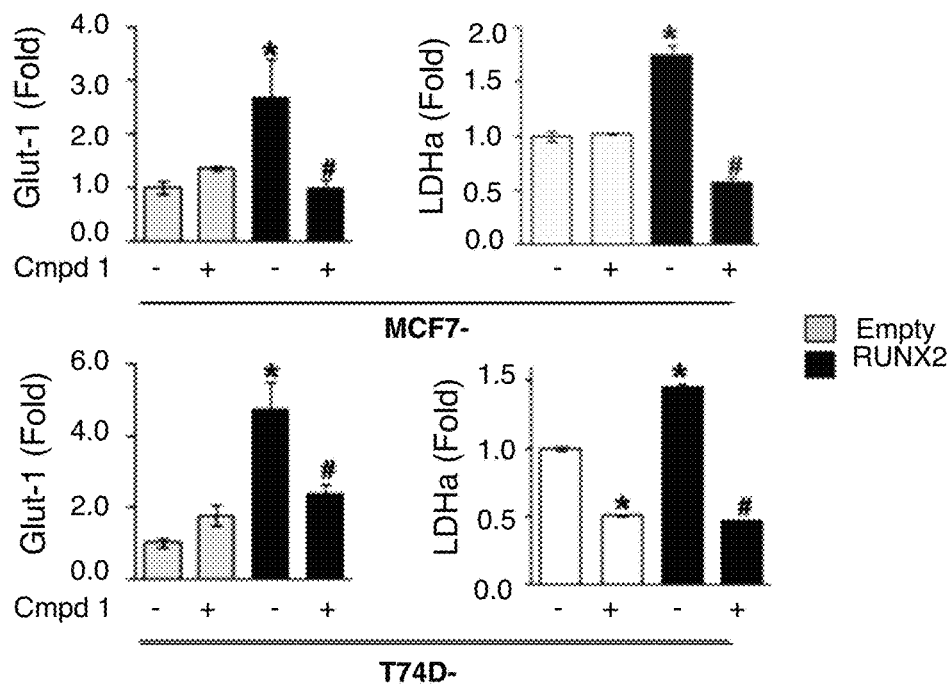

RUNX2 promoted glucose metabolism during BC progression by increasing glucose uptake and expression of genes regulating glycolytic pathways such as Glut-1. To examine if compound 1 modulates glycolytic phenotypes of BC cells, the levels of glucose and lactate in the cell culture medium were examined. Glucose levels significantly decreased in the medium collected from MCF7-RUNX2 and T47D-RUNX2 cells compared to those in Empty controls (i.e., increased glucose consumption/uptake) (FIG. 14A), whereas the level was increased in Hs578t cells with RUNX2 KD (55.5) (i.e., decreased glucose consumption/uptake) (FIG. 14C). Similar to RUNX2 KD, the glucose level increased in the medium collected from ectopic RUNX2-expressing MCF7 and T47D cells as well as MCF7 and MDA-468 cells after compound 1 treatment for 6 hrs (FIGS. 14A-14B) and 24 hrs (FIG. 13C). Slight but insignificant inhibition of glucose consumption after compound 1 treatment was also observed in MDA-231 cells (FIG. 14B). In contrast, compound 1 significantly reduced the lactate concentration (FIGS. 14D-14F). The effect of compound 1 on Glut-1 and LDHA transcription is examined by Q-RT-PCR analysis. RUNX2 increased the mRNA level of Glut-1 (up to 5-fold) and LDHA, which was significantly inhibited by compound 1 (FIG. 14G). Downregulation of Glut-1 and LDHA mRNA levels by compound 1 in BC cells was shown in FIG. 12B and FIGS. 13A-13B. Diminished Glut-1 protein levels were also observed in MDA-468 and MCF7 cells treated with compound 1 for 72 hrs (data not shown). Therefore, reduction of glucose uptake by compound 1 in BC cells may occur through inhibition of Glut-1 expression to inhibit glycolysis.

EXAMPLE 7

Compound 1 Upregulates RUNX2 Levels Through Increased RUNX2 Stability

Figure 15A:
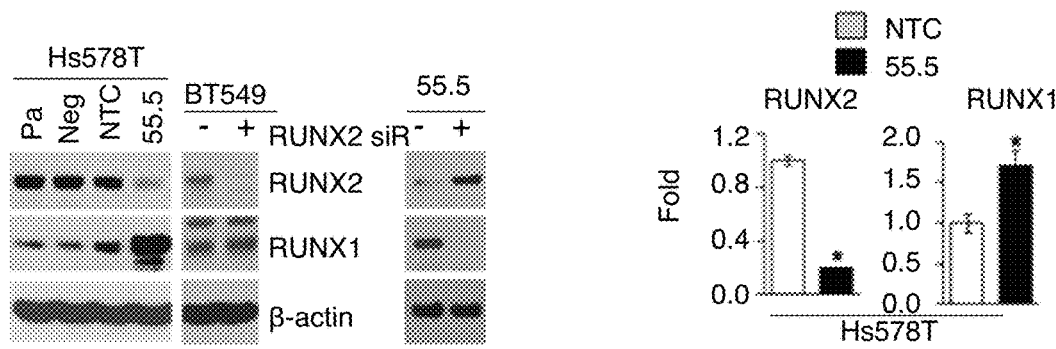
FIGS. 15A-15D show that compound 1 modulates RUNX2 expression.

The RUNX1 levels from the sample sets prepared from the same batches of cDNAs and protein lysates in which the determined RUNX2 levels were examined. As shown in FIG. 15A, both 55.5 cells that stably express RUNX2 shRNA and BT549 cells that were transfected with RUNX2 siRNA for RUNX2 knock-down (KD) exhibited increased RUNX1 protein expression compared to the non-targeting control (NTC) (left), which was also observed at the transcriptional level (right). Conversely, RUNX1 KD in the 55.5 cells resulted in RUNX2 re-expression (middle), supporting a potential compensatory mechanism between RUNX1 and RUNX2 in BC. Consistently, the MCF7 and T47D cells that stably express ectopic RUNX2 down-regulated RUNX1 levels compared to the Empty controls (FIG. 15B), which also was observed in the RUNX1 mRNA levels (FIG. 15C, $2^{nd}$ and $4^{th}$ graphs), indicating RUNX1 and RUNX2 could cross-regulate each other in BC cells.

Figure 15B:
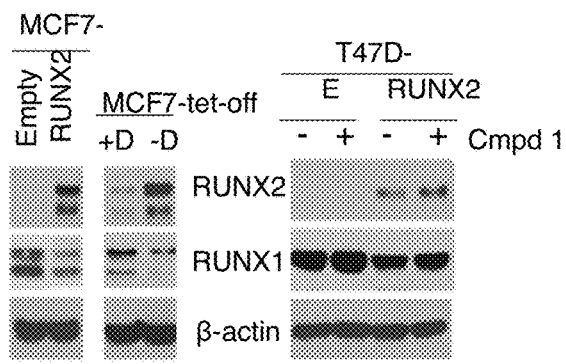
Figure 15C:
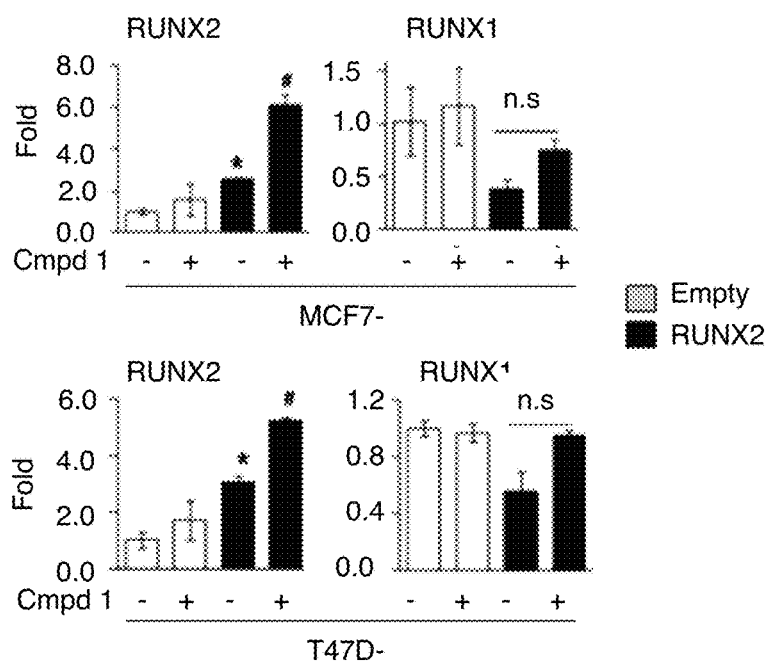
Figure 15D:
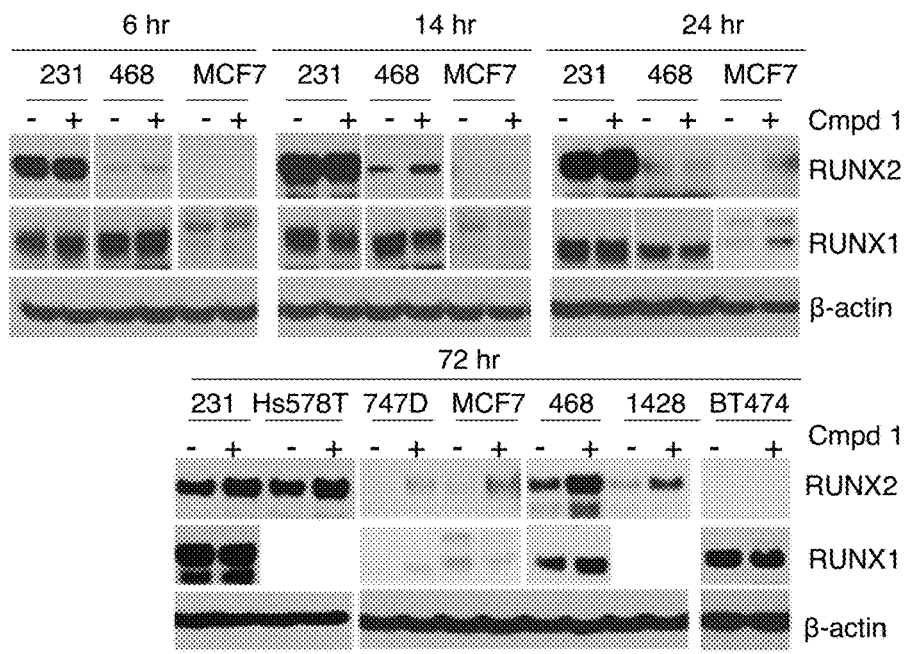

Since compound 1 inhibited the transcriptional activation of RUNX2 downstream genes, it is contemplated that compound 1 alters RUNX1 and/or RUNX2 levels. T47D-RUNX2 and MCF7-RUNX2 cells were treated with compound 1 (50 µM) for 72 hrs and Western blot analysis was run to determine RUNX2 expression. Unexpectedly, compound 1 further enhanced both mRNA and protein expression of RUNX2 (FIGS. 15B-15C). The increase of RUNX2 proteins by compound 1 was commonly observed in other BC cells (FIG. 15D). On the contrary, no further inhibition of RUNX1 protein and mRNA expression by compound 1 in T47D-RUNX2 (FIG. 15B) and MCF7-RUNX2 cells was observed (data not shown). Consistently, RUNX1 protein levels were not altered by compound 1 in most BC cells compared to vehicle controls (FIG. 15D), indicating no further cross-regulation by RUNX2 in the presence of compound 1. Therefore, the biological activity of inhibiting RUNX2-DNA binding by compound 1 could be different from RUNX2 KD.

Figure 16A:
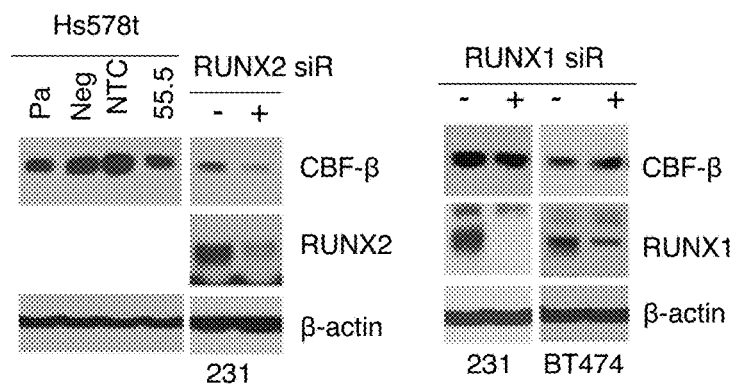
FIGS. 16A-16F show that compound 1 increases RUNX2 stability.
Figure 16B:
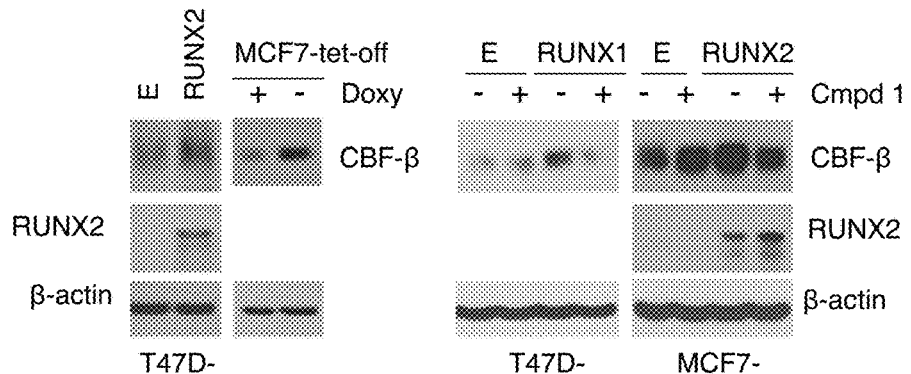
Figure 16C:
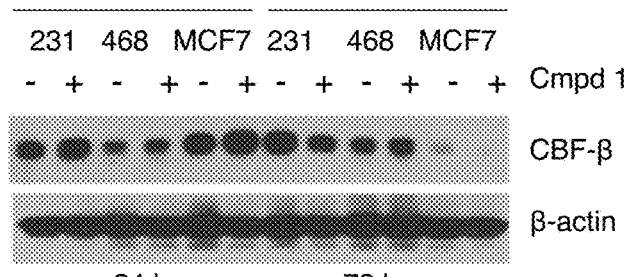
Figure 16C:
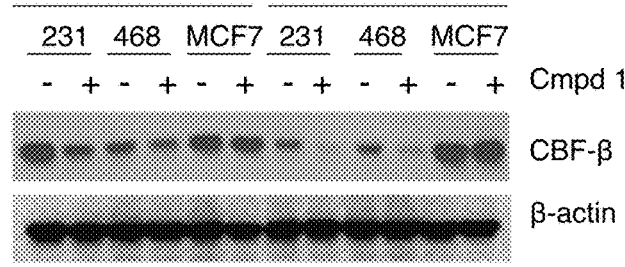

Studies have suggested that the non-DNA-binding subunit of mammalian core binding factor CBF-β stabilizes the RUNX proteins in a conformation that is favorable for DNA binding, which facilitates RUNX-mediated gene transcription. Therefore, compound 1 might regulate CBF-β expression to inhibit transcriptional activity of RUNX2. The protein level of CBF-β decreased in Hs578t (55.5) and MDA-231 cells with RUNX2 KD compared to the non-targeting controls, whereas the level did not change in MDA-231 and BT474 cells with RUNX1 KD (FIG. 16A). In addition, ectopic RUNX2 in both T47D and MCF7 cells resulted in increased CBF-β expression, but compound 1 reduced the CBF-β level (FIG. 16B). In MDA-231, MDA-468 and MCF7 cells, CBF-β levels were increased by compound 1 after 6 hrs of treatment, but the levels decreased after 24 hrs (FIG. 16C). These results suggest that RUNX2, but not RUNX1 might regulate CBF-β expression, which might be modulated by compound 1 in a BC cell type- and time-dependent manner.

Figure 16D:
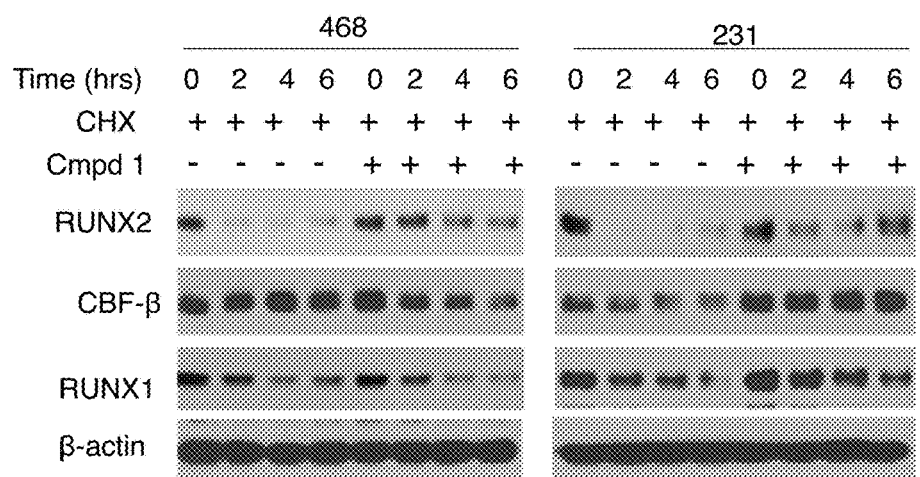
Figure 16E:
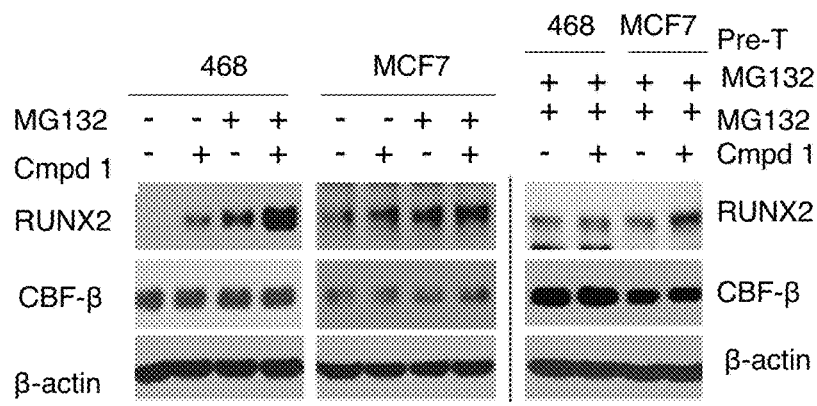

Whether compound 1 could alter RUNX2 stability was examined. MDA-468 and MDA-231 cells were treated with cycloheximide (CHX), a protein synthesis inhibitor, in the presence or absence of compound 1 (50 µM). Compound 1 increased RUNX2 stability in both MDA-468 and MDA-231 cells by delaying protein degradation (FIG. 16D). In contrast, the stability of RUNX1 or of CBF-β was not increased by compound 1 in the presence of CHX (FIG. 16D). Moreover, RUNX2 is normally degraded by the ubiquitin-proteasome pathway. Therefore, MDA-468 and MCF7 cells were co-treated with compound 1 and the proteasome inhibitor MG132 (10 µM) for 18 hrs. RUNX2 protein stability was increased by MG132 alone, which was consistent with known findings, and further increased in the presence of compound 1 (FIG. 16E, left). The increase appeared additive for both MDA-468 and MCF7 cells. In MDA-468 and MCF7 cells pre-treated with MG132 for 1 hr and then co-treated with or without compound 1 for 18 hrs, the RUNX2 level was clearly increased in MCF7 cells by compound 1, and slightly increased in MDA-468 cells (FIG. 16E, right), whereas CBF-β protein stability was not altered by MG132. In addition, ubiquitin expression was decreased by compound 1 in MDA-468 cells and MCF7 cells (data not shown). These results indicate that both proteasome-dependent and -independent pathways might be involved in the increase of RUNX2 stability by compound 1.

Figure 16F:
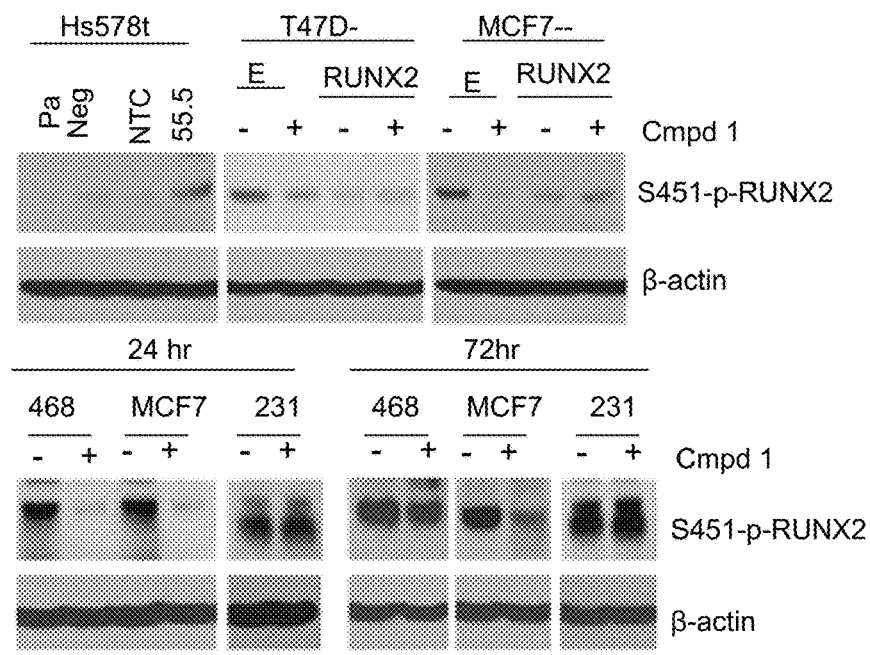

Phosphorylation is an important post-translational mechanism for regulation of RUNX2 stability and activity. It has been shown that the alanine substitution at the S451 residue (S451A) of RUNX2 reduces phosphorylation, leading to decreased DNA binding activity. cdc2 (CDK1) is known to phosphorylate RUNX2 on Ser-451 in vitro, but little is known about the functional significance and regulation of the S451 phosphorylation of RUNX2 in BC. RUNX2 KD cells (55.5) expressed higher level of S451 phosphorylation compared to the non-targeting controls (FIG. 16F), but T47D-RUNX2 and MCF7-RUNX2 cells expressed lower levels of the S451-p-RUNX2 compared to the Empty controls, indicating that RUNX2 could regulate its stability and activity through regulation of phosphorylation at the S451 residue. In contrast, in Empty controls, MDA-468 and MCF7 that express relatively low levels of RUNX2, compound 1 clearly reduced the S451-p-RUNX2 levels, which might contribute to the increased stability of RUNX2 protein. However, little difference was observed in cells that express high levels of RUNX2 (T47D-RUNX2, MCF7-RUNX2 and MDA-231), implying that a negative feedback mechanism suppressing further S451 phosphorylation might be activated to balance the higher levels of RUNX2 by compound 1 or that BC cells might have different biological response to compound 1, which might be related to cellular levels of RUNX2. Furthermore, dynamic shuttling of RUNX2 between cytoplasmic and nuclear compartments could be linked to its gene regulatory activity, promoting post-translational modifications of RUNX2 and/or interactions with co-factors. It is known that RUNX2 distribution and compartmentalization between the cytoplasm and nucleus could be altered by Paclitaxel treatment. In the western blot analysis, however, compound 1 did not block or attenuate nuclear translocation of RUNX2 protein. Taken together, in addition to its interference with RUNX2-DNA binding, compound 1 may increase RUNX2 stability and reduce phosphorylation and CBF-β levels, which may be through direct or indirect mechanisms.

EXAMPLE 8

Therapeutic Targeting in Hippo Pathway with Compound 1
RUNX2 Inactivates the Hippo Tumor Suppressor Pathway in Luminal Breast Cancer The Hippo tumor suppressor pathway is active in the context of stable E-Cadherin interactions that promote epithelial cell:cell polarity. Under these conditions, E-Cadherin signaling maintains TAZ localization to 14-3-3 complexes in the cytosol and eventual ubiquitination and degradation. Upon induction of oncogenic events, which include sE-Cad production and cooperation with HER2 receptors, the Hippo pathway is inactivated and in this context TGFβ signaling promotes TAZ translocation to the nucleus where it can interact with transcription factors, such as RUNX2, which are responsible for activation of genes that promote cell invasion, survival, and tumorsphere formation.

Figure 17:
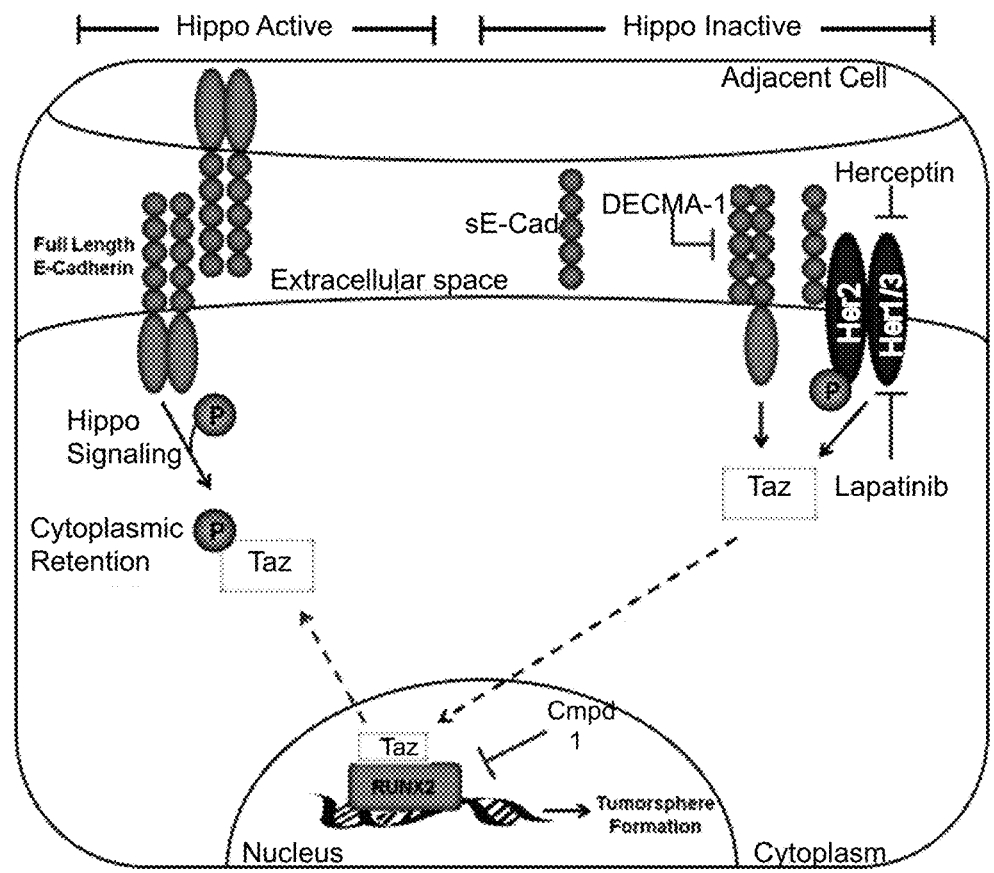
FIG. 17 shows that inactivation of the Hippo tumor suppressor pathway by RUNX2 promotes a tumorigenic phenotype in luminal breast cancer cells. Several therapeutic targets are indicated that inhibit the tumorigenic phenotype described herein (tumorsphere formation), including Herceptin/Lapatinib targeting of HER2, DECMA-1 targeting of sE-Cad, and compound 1 targeting of RUNX2.

RUNX2 expression supported a TGFβ-driven oncogenic signaling pathway that involves TAZ-mediated activation of tumorsphere formation, the production of soluble E-cadherin (sE-Cad), and cooperation with HER2, which was increased in RUNX2 expressing cells. The data indicate that E-Cad stabilizes HER2 and sensitizes breast cancer cells to HER2 targeted drugs and that luminal breast cancer cells expressing RUNX2 rely on HER2 signaling to potentiate their tumorigenic phenotype. The effects on tumorsphere formation are consistent with known roles for RUNX2 and TAZ in tumor-initiating functions. These results have identified several therapeutic targets that converge on RUNX2: TAZ transcriptional regulation in breast cancer cells. The combined signaling pathways may be responsible for a transcriptional program that mediates breast cancer tumorsphere formation and anchorage-independent growth (FIG. 17).

Role of RUNX2 Cofactor TAZ in Anchorage Independent Growth

Figure 18B:
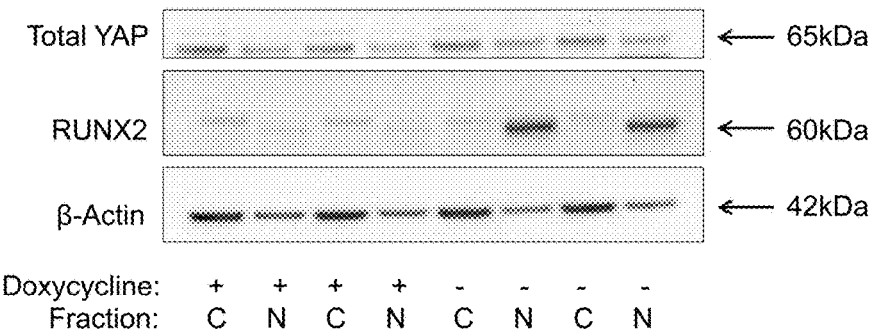
Figure 18C:
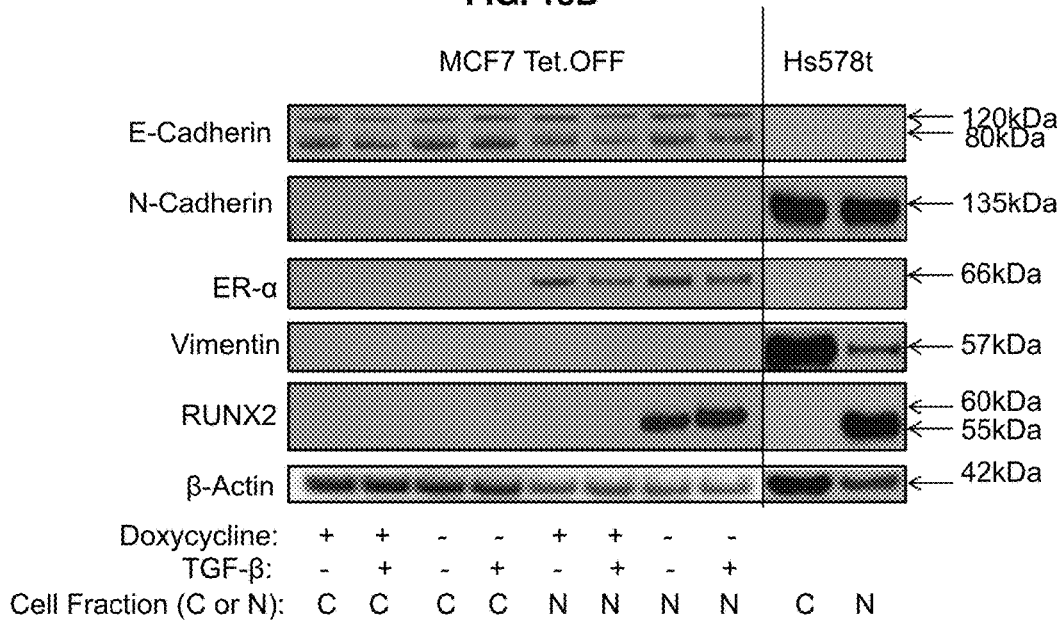
Figure 19A:
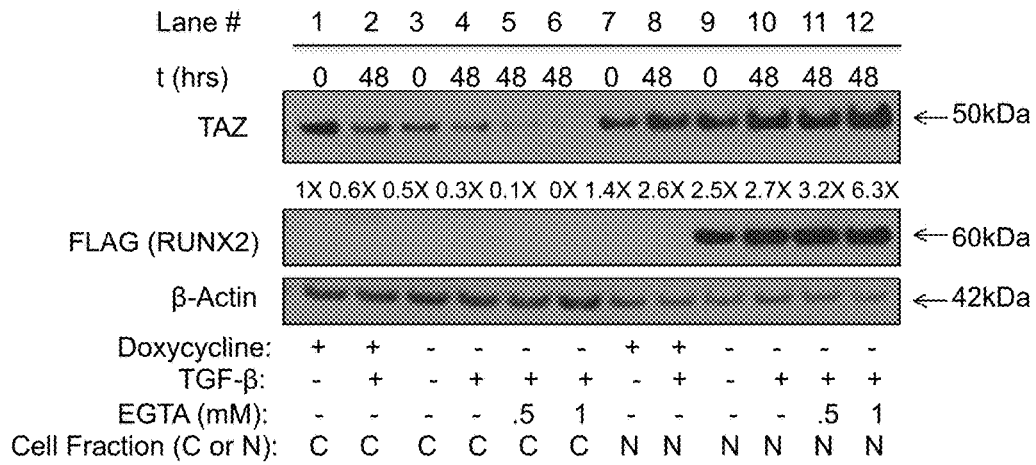
FIGS. 19A-19E illustrate that TAZ cooperates with RUNX2 to promote tumorsphere formation.
Figure 19B:
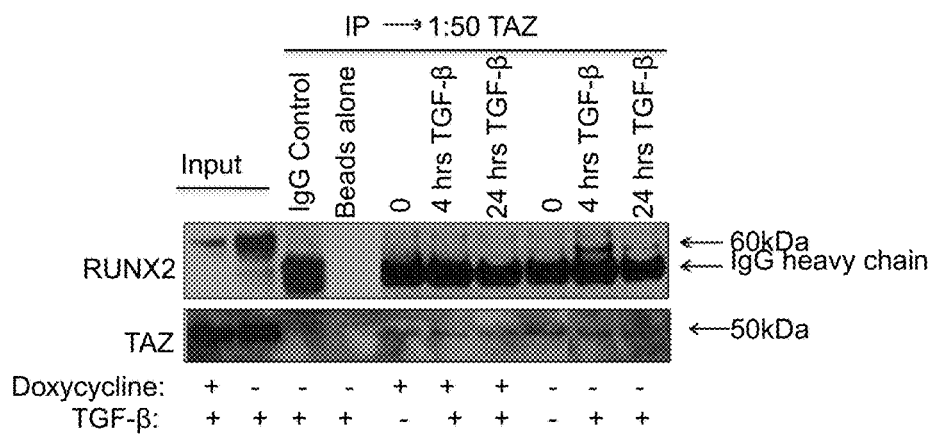
Figure 19C:
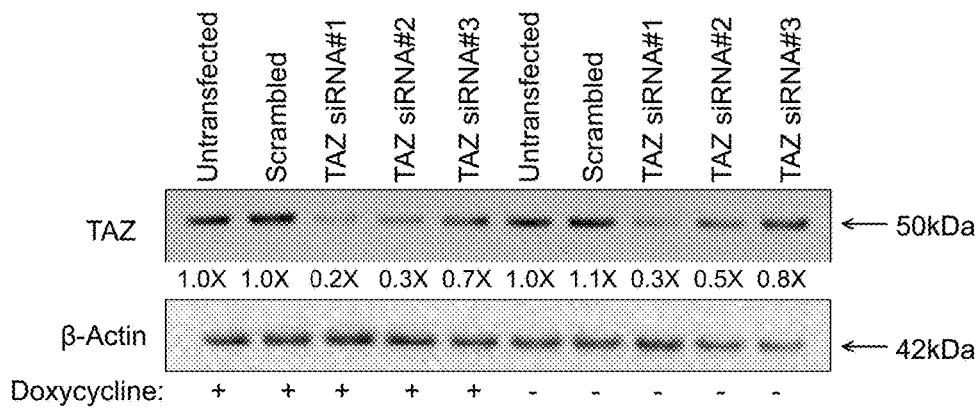
Figure 19D:
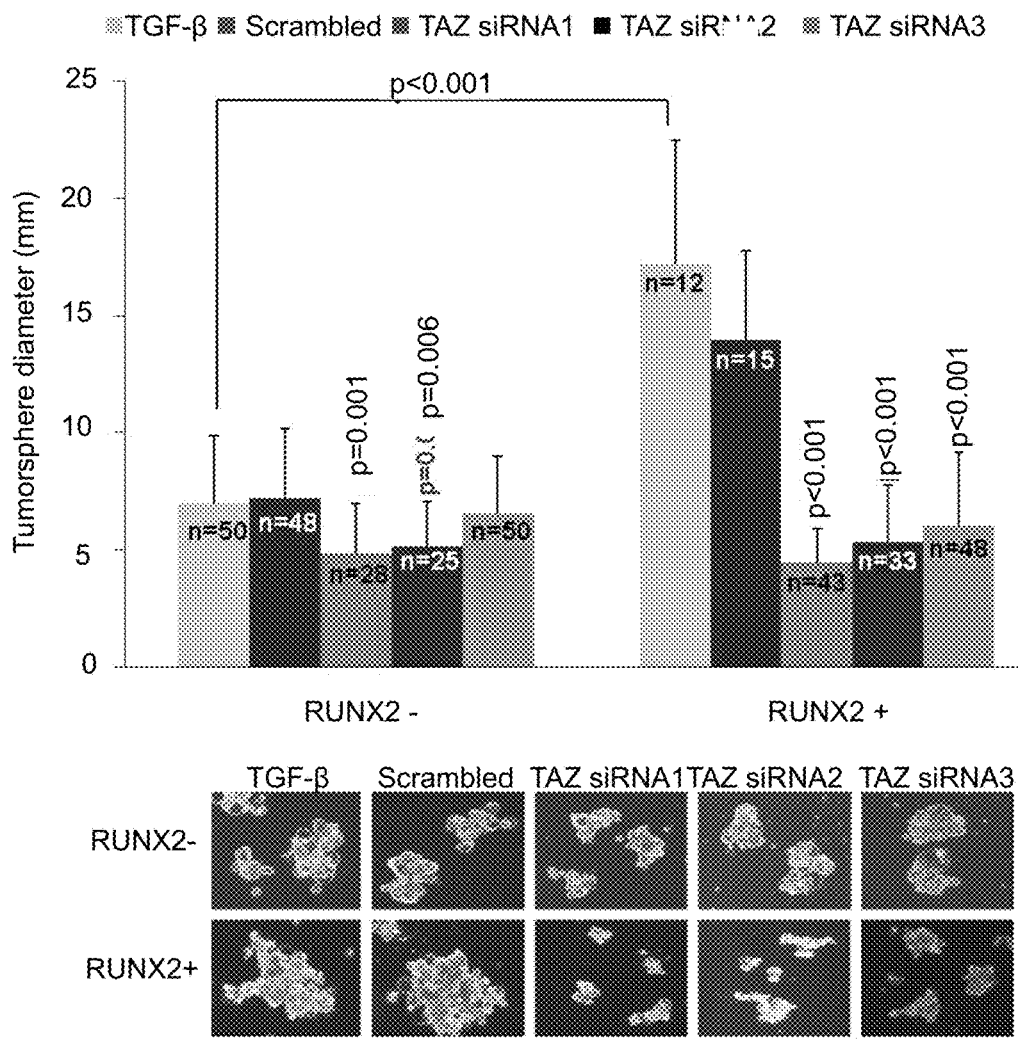

The Hippo signaling effectors, TAZ and YAP, are important RUNX2 transcriptional cofactors that interacts with the RUNX2 C-terminal domain. YAP expression in MCF7 cells was low and levels in response to RUNX2 expression did not change in these cells (FIG. 18B). However, TAZ nuclear levels were higher upon induction of RUNX2 expression compared to cells with low RUNX2 expression (FIG. 19A, lanes 7 and 9). Disruption of cell:cell contacts with EGTA resulted in additional increases in TAZ nuclear levels (lanes 11 and 12) with a concomitant decrease in cytosolic TAZ (lanes 5 and 6). Immunoprecipitation of TAZ showed that RUNX2 and TAZ were associated within the same immune complex only in RUNX2 positive MCF7 cells treated with TGFβ (FIG. 19B). To determine if RUNX2 and TAZ cooperativity was necessary for tumorsphere formation, MCF7 cells expressing inducible RUNX2 were transfected with scrambled siRNA or three specific siRNAs targeting TAZ. TAZ knockdown to levels 70-80% (siRNA1), 50-70% (siRNA2) or 30% (siRNA3) of control (scrambled siRNA) was observed in cells expressing low (doxycycline +) or high (doxycycline −) RUNX2 (FIG. 19C). Tumorsphere formation of RUNX2 positive cells was inhibited by all three specific siRNAs about 3-fold compared to untreated or scrambled siRNA over 12 days (FIG. 19D). Although significant (p=0.001 and p=0.006), TAZ siRNA#1 (4.85±2.11) and siRNA#2 (5.16±1.91) knockdown produced a modest decrease in tumorsphere size compared to controls in RUNX2 negative cells (6.97±2.89 for TGFβ treated and 7.18±2.98 for scrambled). TAZ siRNA#3 had no significant effect in these cells. However, TAZ siRNA #1, 2, and 3 (4.43±1.47, 5.35±2.42, and 6.05±3.12 respectively) inhibited tumorsphere formation 2.5 to 4-fold in the RUNX2 positive MCF7 cells compared to controls (17.21±5.28 and 13.97±3.81 for TGFβ and scrambled controls respectively).

Figure 19E:
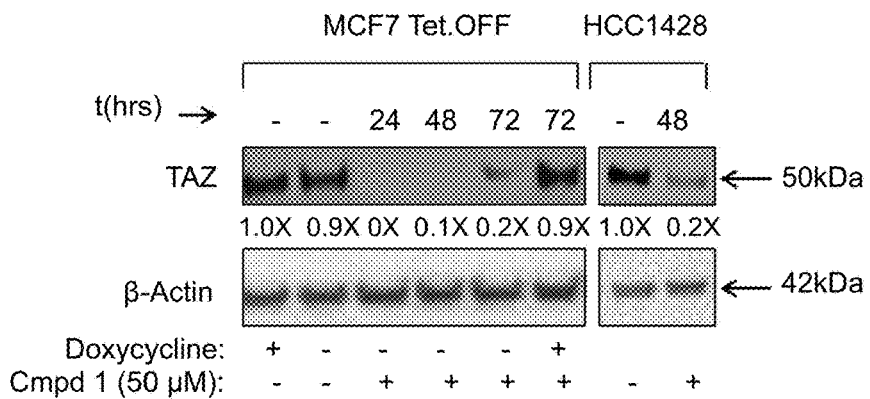

Interestingly, a 30% reduction in TAZ protein levels (FIG. 19C) was sufficient to significantly decrease tumorsphere formation by 65% in RUNX2 positive cells (p<0.001) while having no effect in RUNX2 negative cells. Further, breast cancer cell targeting with the RUNX2-selective compound 1 lowered TAZ nuclear levels within 24 hr in RUNX2 positive cells (FIG. 19E; doxycycline –). However, compound 1 treatment of RUNX2 negative cells (doxycycline+) had no affect on nuclear TAZ levels over 72 hr. Similarly, in HCC1428 breast cancer cells expressing endogenous RUNX2, treatment with compound 1 led to an 80% reduction in nuclear TAZ levels compared to vehicle-treated controls (FIG. 19E).

Figure 20A:
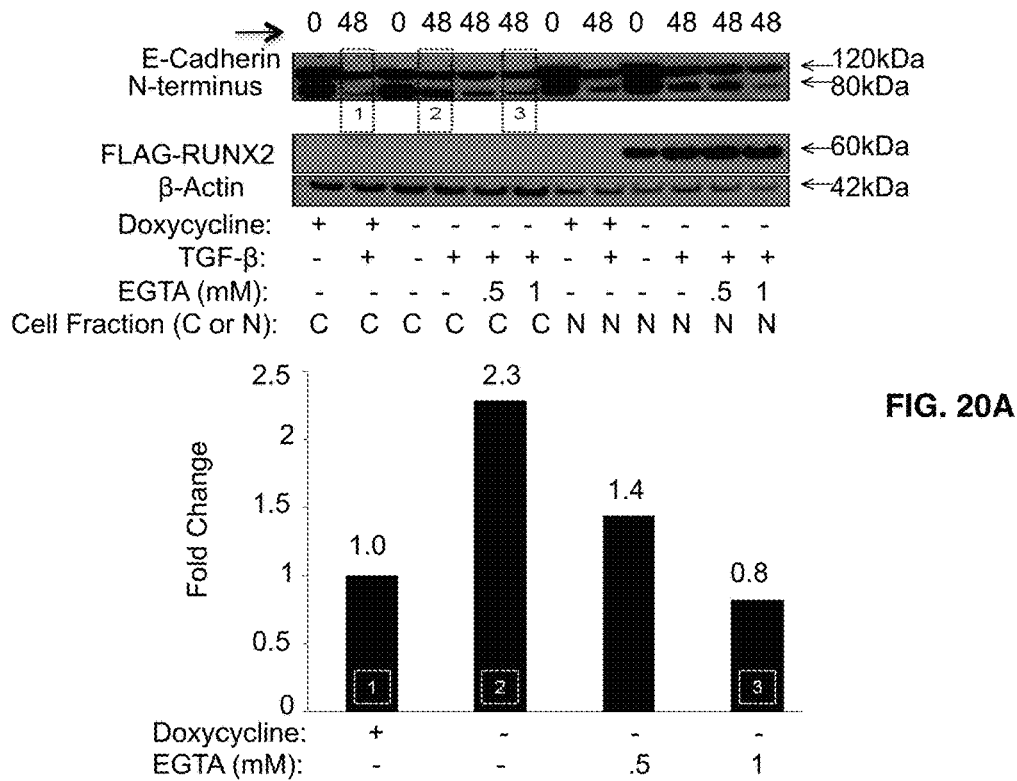
FIGS. 20A-20E show RUNX2 expression is associated with production of soluble E-Cadherin (sE-Cad) and tumorsphere formation.
Figure 20B:
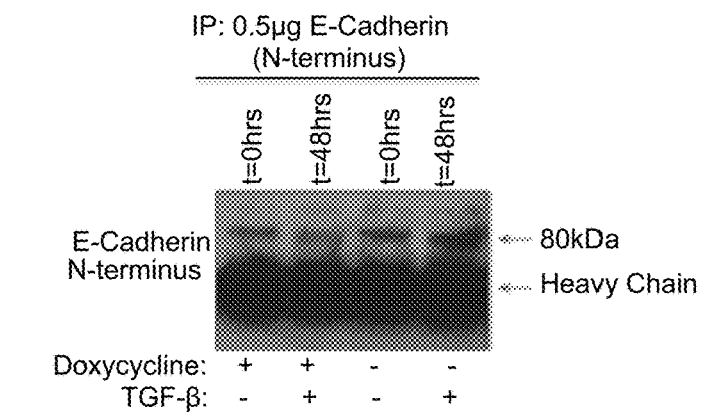
Figure 20B:
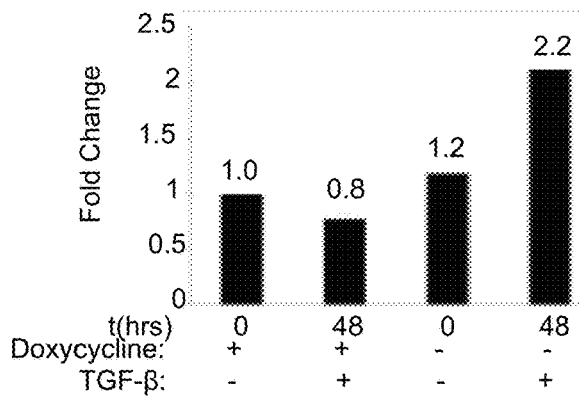
Figure 20C:
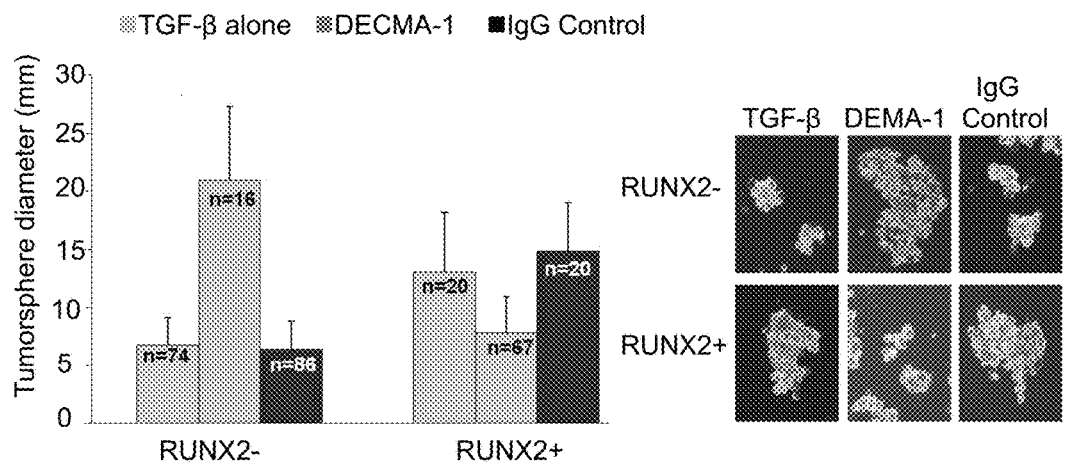
Figure 20D:
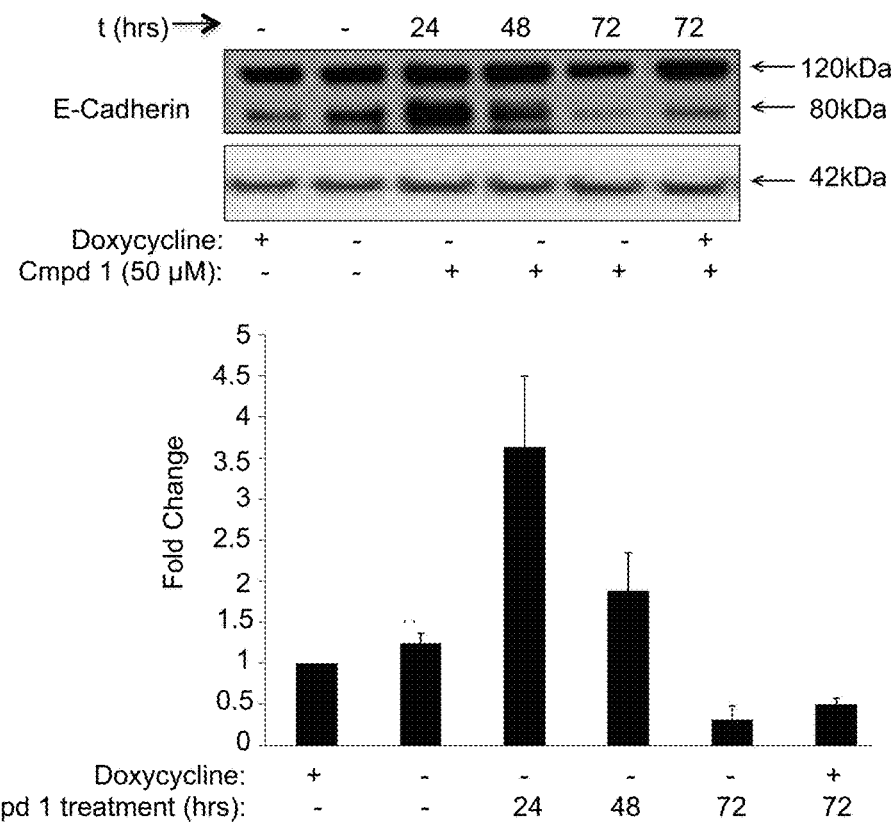
Figure 20E:
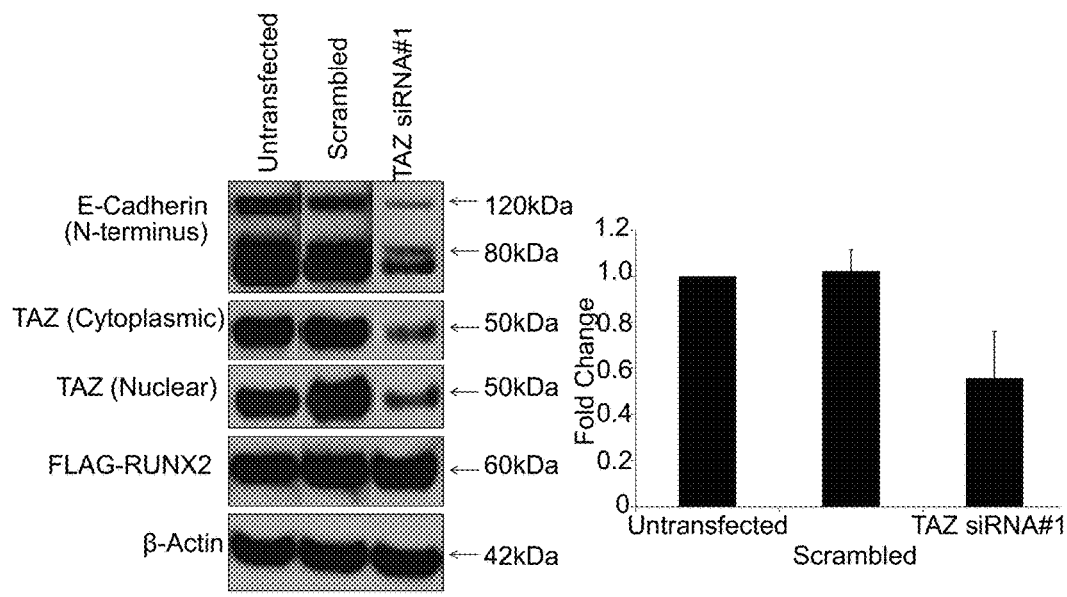

Production of Oncogenic E-Cadherin Ectodomain (sE-Cad) is Dependent on RUNX2 and TAZ The EMT can be regulated by RUNX2 in some breast cancer cells. However, in luminal breast cancer cells, RUNX2 did not promote the loss of E-Cadherin, the downregulation of ER or the expression of N-Cadherin and Vimentin, which are indicative of an EMT progression (FIG. 20C). Instead, RUNX2 was associated with a 129% increase in oncogenic E-Cadherin fragment, sE-Cadherin (sE-Cad; 80 kDa) consisting of the E-Cadherin ectodomain (FIG. 20A). RUNX2 positive cells expressed 2.5-fold more sE-Cad in response to TGFβ treatment (48 hr), compared to RUNX2 negative MCF7 cells (FIG. 20A, boxes 1 and 2). sE-Cad protein levels were reduced after treatment with the $Ca^{+2}$ chelator EGTA suggesting that sE-Cad was associated with the cell surface. sE-Cad is an established biomarker for metastatic prostate cancer and has been found in the conditioned media of DU145 prostate cancer cells where it promotes tumorigenesis and mediates invasion. Conditioned media from MCF7 cells expressing RUNX2 contained 2.3-fold higher levels of sE-Cad ectodomain compared to RUNX2 negative cells (FIG. 20B). In contrast to RUNX2 positive cells, after 48 hr treatment with TGFβ there was a 30% reduction in sE-Cad secreted into the conditioned media by RUNX2 negative cells. Baseline levels of sE-Cad released by the MCF7 Tet.OFF cells were similar in RUNX2 positive and RUNX2 negative cells at t=0. E-Cadherin and sE-Cad are neutralized using the ectodomain-specific E-Cadherin antibody, DECMA-1. Tumorsphere size was significantly inhibited in RUNX2 positive cells treated with DECMA-1 over 10 days (7.85±3.11; p<0.001) compared to TGFβ and IgG controls (13.06±5.16 and 14.88±4.14 respectively) indicating RUNX2 positive cells rely on sE-Cad for tumorsphere formation (FIG. 20C). However, DECMA-1 promoted larger tumorsphere formation in RUNX2 negative cells, perhaps through its ability to prevent E-Cadherin-dependent growth suppression, thus increasing cell proliferation. The RUNX2-selective compound 1 increased sE-Cad production 3.5-fold within the first 24 hr of treatment, but sE-Cad levels declined by almost 20-fold by 72 hr in RUNX2 positive cells (FIG. 20D). Baseline levels of sE-Cad were significantly higher in RUNX2 positive cells prior to treatment with compound 1 (p=0.02). A 2-fold decrease in sE-Cad production in RUNX2 negative cells (doxycycline +) (FIG. 20D) may be due to compound 1 inhibition of endogenous RUNX2 or of low amounts of RUNX2 produced by the Tet.OFF system even in the presence of doxycycline. Further, siRNA-targeted knockdown of the RUNX2 cofactor TAZ resulted in a 50% reduction in sE-Cad ectodomain expression without affecting RUNX2 levels (FIG. 20E). In summary, MCF7 cells naturally produce sE-Cad, its levels can be modulated by the expression of RUNX2 and TAZ, and expression of sE-Cad ectodomain mediates tumorsphere formation in RUNX2-expressing luminal breast cancer cells.

Figure 21A:
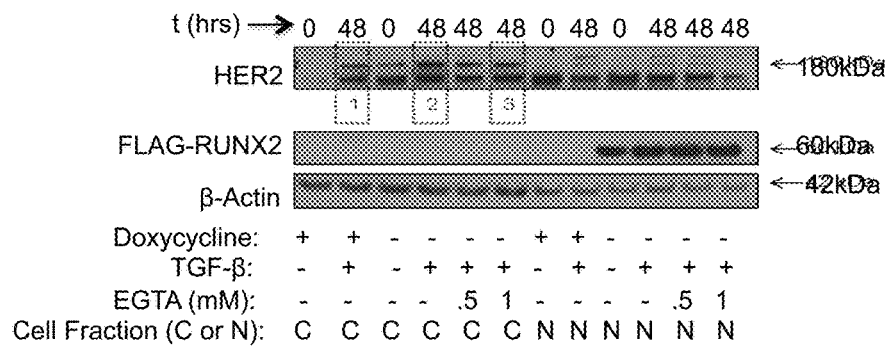
FIGS. 21A-21C demonstrate HER2 expression in RUNX2 positive cells that express elevated sE-Cad levels sensitizes cells to HER2-targeted drugs.
Figure 21A:
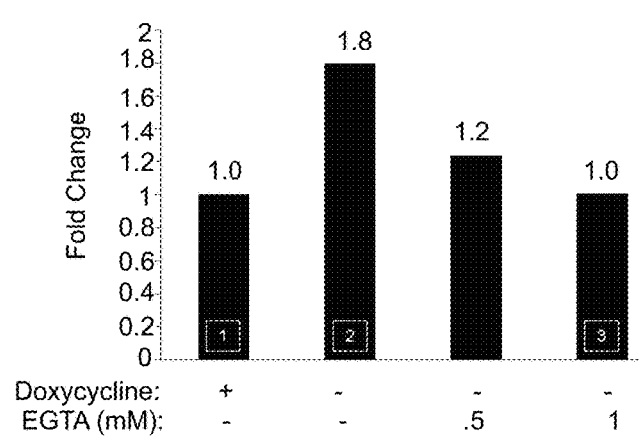

Therapeutic Targeting of sE-Cad/HER2 Signaling in RUNX2-Expressing Luminal BC Cells The ErbB2/HER2 receptor family member is expressed in a subset of luminal breast cancer cells in the absence of gene amplification and HER2 is one of the main targets of sE-Cad. HER2 interacts with sE-Cad to promote ligand-independent cell signaling in triple negative breast cancer cells, but its role in luminal breast cancers (in the absence of gene amplification) is undefined. After 48 hr treatment with TGFβ, RUNX2 positive MCF7 cells expressed 2-fold higher HER2 levels than RUNX2-negative cells (FIG. 21A, boxes 1 & 2) suggesting that RUNX2-mediated production of secreted sE-Cad (FIG. 20A) may stabilize HER2. Inhibition of sE-Cad levels at the cell surface with EGTA treatment (E-Cadherin destabilization to remove sE-Cad bound at the cell surface; FIG. 20A) correlated with a decrease in HER2 to levels observed in RUNX2 negative cells (FIG. 21A, box 3).

Figure 21B:
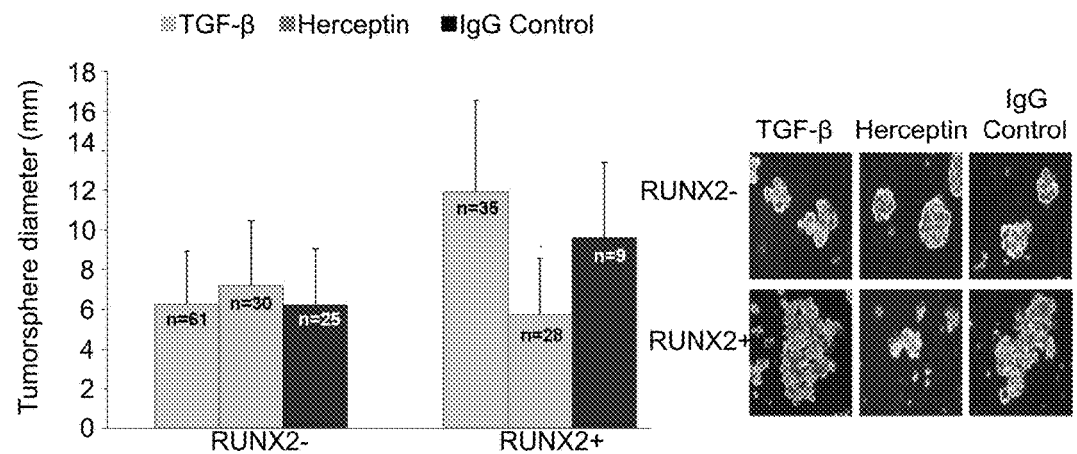
Figure 21C:
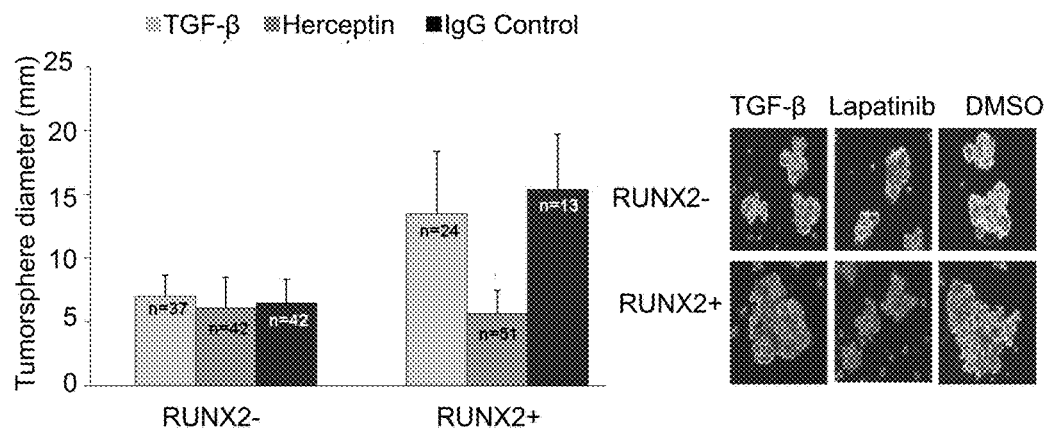

To test for functional HER2, the effect of HER2-targeted agents on tumorsphere formation was determined. The Herceptin monoclonal antibody binds the extracellular domain of HER2 and promotes receptor internalization and degradation, prevents homo/heterodimerization, and mediates antibody-dependent cellular cytotoxicity. Herceptin inhibited tumorsphere formation in RUNX2 positive MCF7 cells by 2-fold (11.91±4.65 to 5.76±2.83; p<0.001), without affecting tumorsphere formation in RUNX2 negative cells (6.25±2.68 to 7.2±3.27; p=0.145) (FIG. 21B). Isotype-matched IgG had no significant impact on tumorsphere size. Lapatinib is a small molecule receptor tyrosine kinase inhibitor that is able to cross lipid bilayers and bind the intracellular kinase domain of HER2 to inhibit receptor activation. RUNX2 positive cells were very sensitive to lapatinib treatment, with tumorsphere size reduced by 2.5-fold relative to vehicle control over 15 days (13.48±4.87 to 5.68±1.78; p<0.001) (FIG. 21C). Lapatinib had no effect on the tumorsphere formation capacity of RUNX2 negative cells (6.99±1.67 to 6.08±2.38). These results are consistent with a cooperative function for HER2 and sE.Cad in promoting a tumorigenic phenotype in luminal breast cancer cells expressing RUNX2.

Figure 22A:
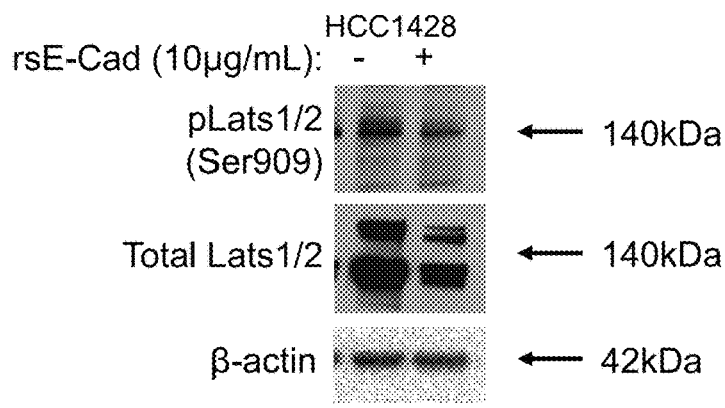
FIGS. 22A-22B demonstrate that Hippo signaling is regulated by both oncogenic soluble E-Cadherin and RUNX2 targeting compound 1.
Figure 22B:
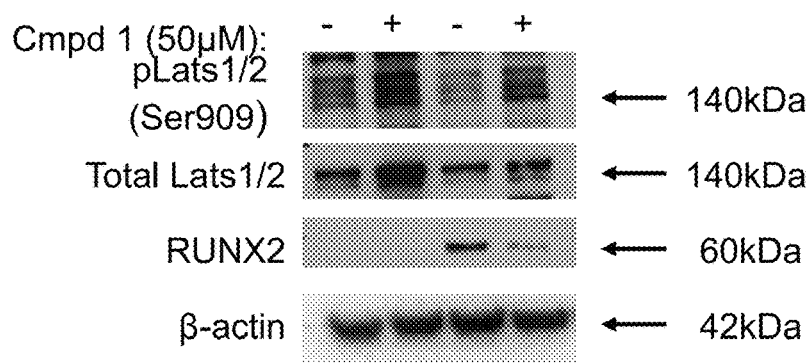

Hippo Tumor Suppressor Pathway Activated by Compound 1 in Luminal Breast Cancer Cells It was demonstrated that RUNX2 inactivates and RUNX2 inhibitors (compound 1) activate the tumor suppressor pathway Hippo signaling (FIGS. 22A-22B) in HCC1428 luminal breast cancer cells. Treatment with recombinant soluble E-Cadherin showed a decline in phosphorylation of the Lats1/2 tumor suppressors (FIG. 22A). Compound 1 treatment demonstrated an increase in phosphorylation of the tumor suppressors (FIG. 22B) which is consistent with activation of Hippo signaling and TAZ translocation to the cytosol.

EXAMPLE 9

RUNX2 Oncogenic Function Reversed and Mitochondrial Enzyme Activity Restored by Compound 1

Compound 1 Increases Pyruvate Dehydrogenase Activity (PDH)

Figure 23A:
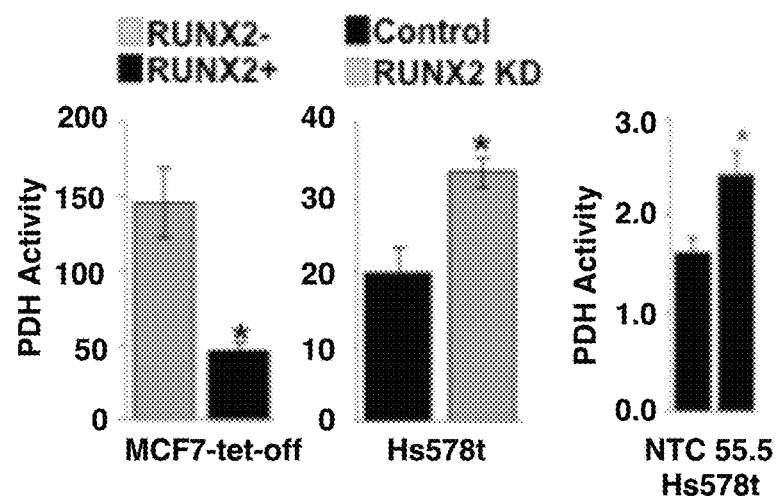
FIGS. 23A-23B demonstrate that RUNX2 inhibits PDH activity, which increases in response to RUNX2-targeting compound 1 drug treatment.
Figure 23B:
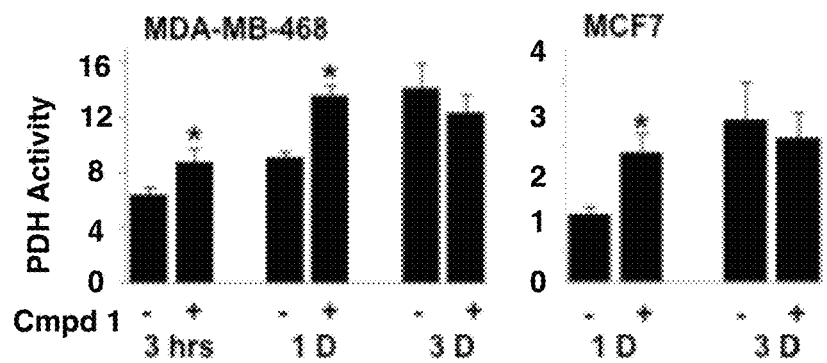
Figure 24A:
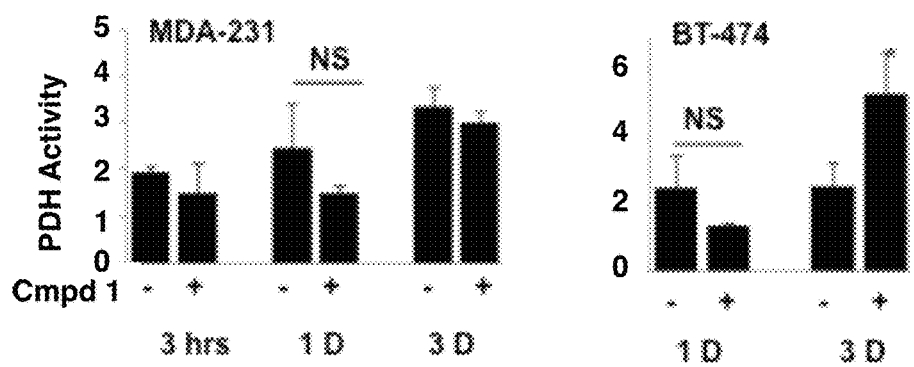
FIGS. 24A-24B demonstrate that PDH activity increases in response to RUNX2-targeting compound 1 drug treatment. PDH activity (ΔOD/min/mg protein) was determined as in FIGS. 10A-10B.
Figure 24B:
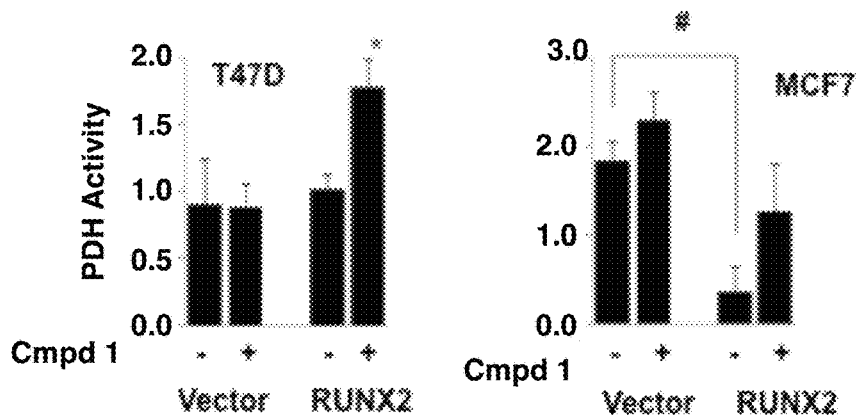

It was shown in an antibody-specific microtiter plate assay that there is an increase in PDH activity in RUNX2 knockdown cells (FIG. 23A). It is shown in two breast cancer cell lines, MDA-MB-468 and MCF7, that compound 1 increases PDH activity. Compound 1 is a metabolic targeting agent because it increases PDH enzymatic activity (FIG. 23B) consistent with RUNX2 inhibition. As confirmation it was shown that overexpressing RUNX2 in MCF7 cells inhibits PDH activity but compound 1 increases PDH activity in same cells (FIG. 24A-24B). Furthermore using either luminal or TNBC cells it was demonstrated that compound 1 inhibits RUNX2 transcriptional activity and increases PDH activity (FIGS. 25A-25D).

Compound 1 Increases Complex I Activity

Figure 26A:
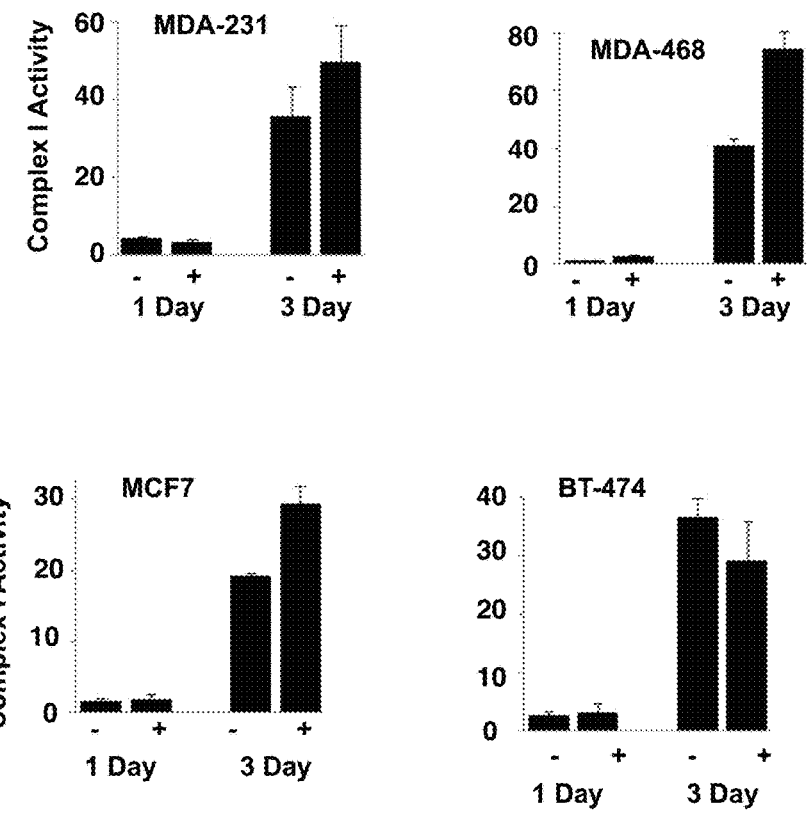
FIGS. 26A-26B demonstrate that Complex I Activity measures the ability of NADH Dehydrogenase to transfer electrons to the electron transport chain in mitochondria (ΔOD/min/mg protein).
Figure 26B:
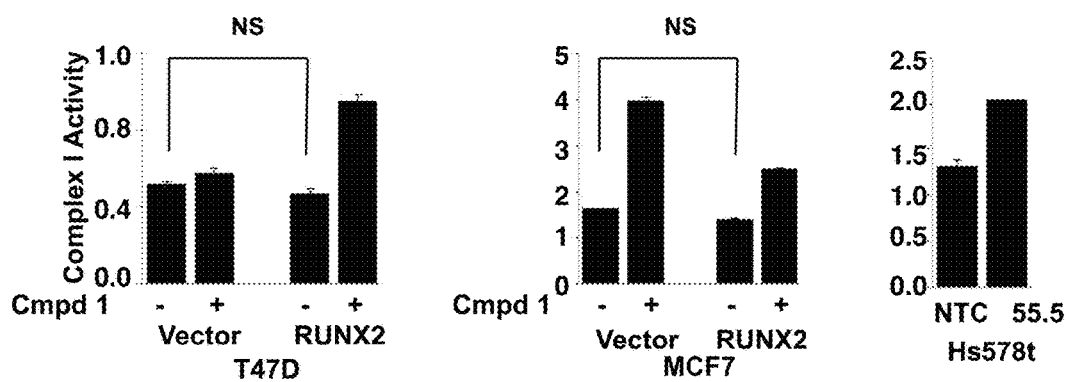

Complex I is a rate-limiting step in oxidative phosphorylation. It was demonstrated that compound 1 increased Complex I activity in MDA-468 and MCF7 cells (FIG. 26A) compared to controls (FIG. 26B).

Compound 1 Increases Mitochondrial Reactive Oxygen Species (ROS) Production

Figure 27A:
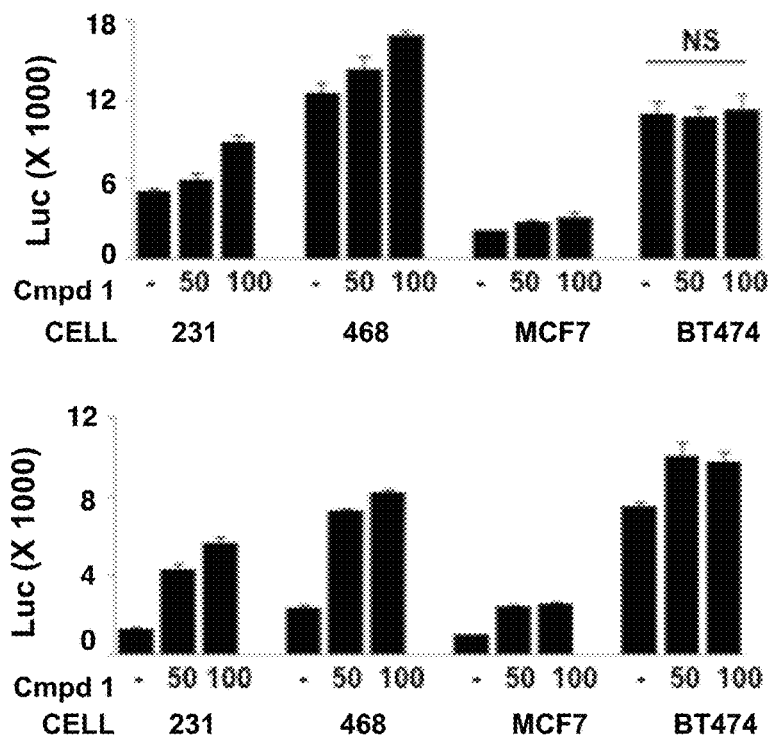
FIGS. 27A-27B demonstrate that ROS levels in breast cancer cells treated with anti-RUNX2 compound 1.
Figure 27B:
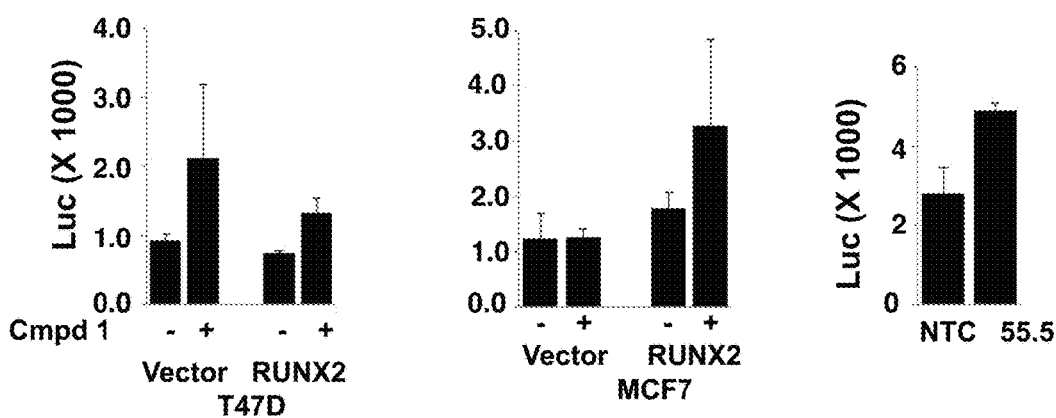

The ability of mitochondria to produce reactive oxygen species is a measure of increased electron flow through the electron transport chain. It was demonstrated that MDA-231, MDA-468, MCF7 and BT474 breast cancer cells treated with compound 1 showed an increase in mitochondrial ROS production (FIG. 27A) compared to control (FIG. 27B).

EXAMPLE 10

Compound 1 Suppresses In Vivo Tumor Growth and Metastasis

Figure 28A:
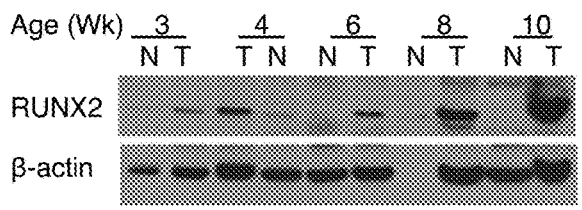
FIGS. 28A-28E show the effects of compound 1 on RUNX expression in MMTV-PyMT transgenic mice.

To assess the in vivo activity of compound 1, the MMTV-PyMT transgenic model was used, in which the polyoma middle-T oncogene is activated under control of the mouse mammary tumor virus promoter (MMTV-PyMT). This model was suitable since it mimics human breast cancer from the stages of initial hyperplasia to ductal carcinoma in situ and invasive ductal carcinoma. Conditional RUNX2 deletion in the MMTV-PyMT transgenic mouse model of BC has been shown to delay tumor incidence and enhance overall survival. MMTV-PyMT females developed palpable mammary gland tumors at approximately 5~6 weeks of age, and high levels of RUNX2 were expressed in tumor tissues compared to normal mammary gland in age-matched control mice over 10 weeks of observation (FIG. 28A). RUNX2 expression also increased with disease progression. 45-day-old mice were assigned randomly to control and compound 1 treatment groups. Tumor incidence was measured every 1 to 2 days, and mice were observed for up to 90 days of age (total of 45 days of compound 1 treatment) at which time the mice were sacrificed, tumor volume was calculated in Example 1, and tumors were excised and weighed. The intraperitoneal (i.p.) administration of compound 1 into the MMTV-PyMT mice (up to 20 mg/kg) delayed tumor development and reduced tumor burden in transgenic MMTV-PyMT mice. We observed compound 1 significantly delayed the onset of the tumors (FIG. 29A). Statistical analysis by the two-sample Wilcoxon rank-sum (Mann-Whitney) test revealed significance between vehicle control group and each of the compound 1-treated groups (p<. 05).

Cancer Cell Migration Inhibited by Compound 1

Figure 29E:
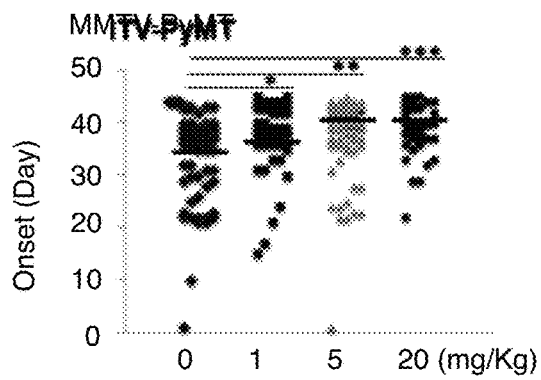
Figure 29E:
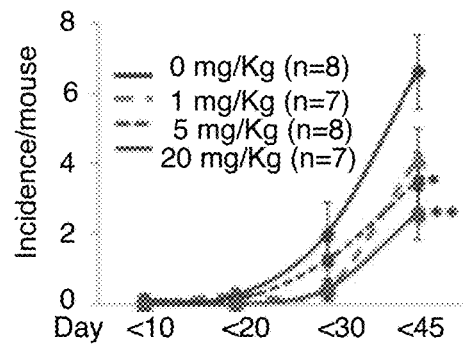
Figure 29E:
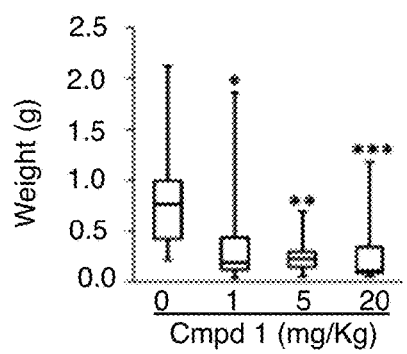
Figure 29E:
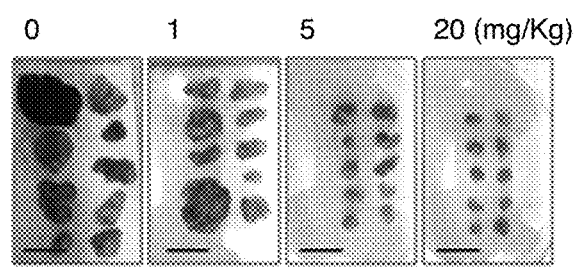
Figure 29E:
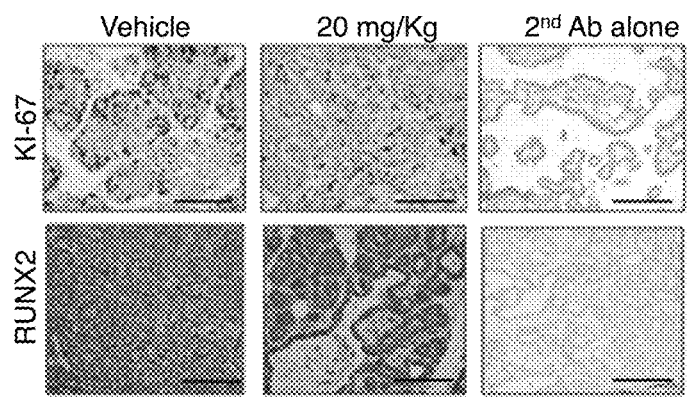

Compound 1-treated MMTV-PyMT mice exhibited significant decrease in tumor incidence compared to vehicle control animals. The incidence per mouse at the final day was 6.63±1.05 (mean±SEM) in vehicle-treated mice, 4.14±0.88 in 1 mg/Kg, 3.05±2.57 in 5 mg/Kg (P=0.037), and 2.57±0.72 in 20 mg/Kg compound 1-treated group (P=0.008) (FIG. 9B, left). The fraction (%) of mice with over 6 tumors was 60±20% (mean±SEM) in control group, but no mice in 20 mg/Kg compound 1-treated group had over 6 tumors (P=0.05) (FIG. 29B, right). Mice with less than 3 tumors were only 10% of the control group, but increased to 40% and 55% of 5 mg/Kg and 20 mg/Kg compound 1-treated groups, respectively. A reduction in the tumor weight was found (FIG. 29C) in compound 1-treated mice. Representative tumors are shown in FIG. 9D. Since compound 1 had an inhibitory effect on in vitro BC cell growth, it was determined whether compound 1-driven inhibition of mammary tumorigenesis is due to an effect of compound 1 on cell proliferation. IHC analysis of Ki67 (proliferative index) in tumor sections showed that staining of Ki67 was much weaker in tumors from compound 1-treated mice than in control mice (FIG. 29E, upper panel).

Figure 28B:
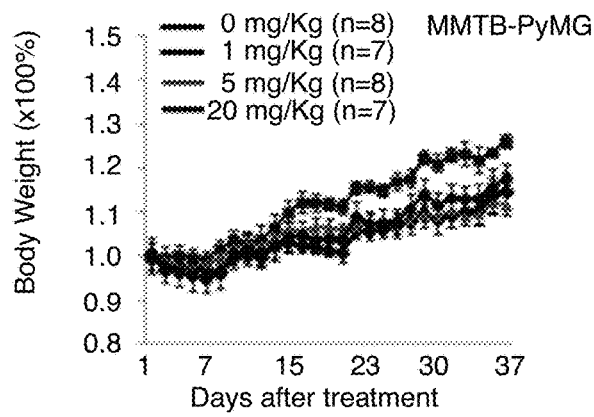
Figure 28C:
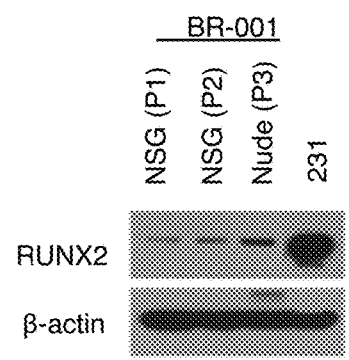
Figure 29F:
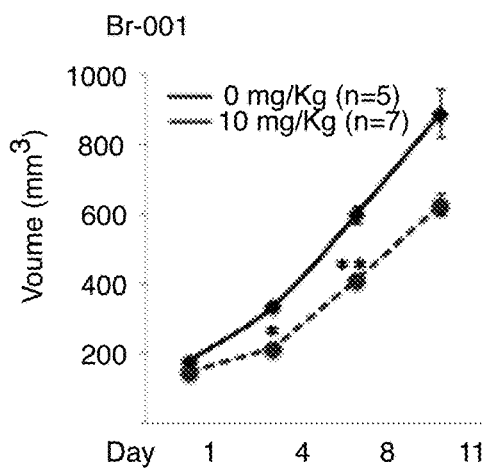
Figure 29G:
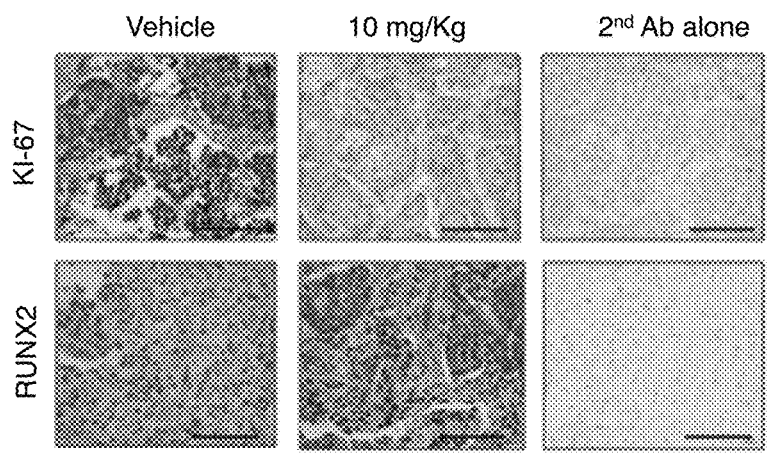

Patient-derived tumor xenografts (PDX) are powerful pre-clinical models to recapitulate the diversity of human tumors. In a TNBC-PDX Br-001 model, RUNX2 expression was positive during continuous passage from P1 to P3 (FIG. 28C), and a significant decrease of tumor volume was observed in the compound 1-injected Br-001-bearing athymic mice (10 mg/kg, i.p.) (FIG. 29F). In this PDX model, Ki-67 expression was markedly reduced in mice injected with compound 1 (FIG. 29G). In both MMTV-PyMT mammary and PDX tumors, higher RUNX2 staining was observed in most of the tumor sections from compound 1-injected mice compared to vehicle control mice (FIGS. 29E, 29G, lower panel), but only negligible caspase-3 staining and no necrosis were observed in the tumor sections from vehicle control or compound 1-injected mice (data not shown), which suggest that compound 1 might delay detectable tumor growth in mice without inducing apoptosis.

Figure 28D:
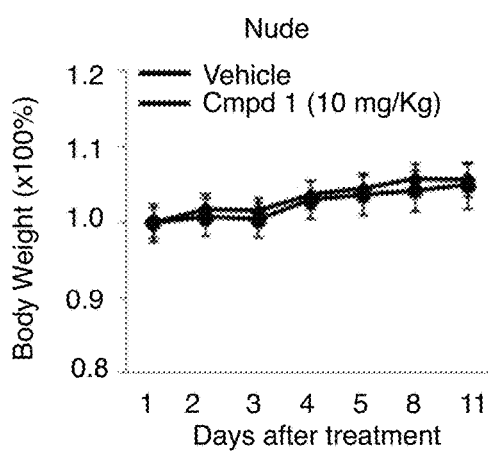
Figure 28E:
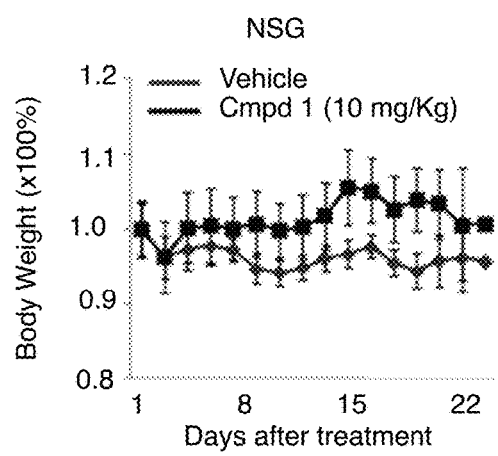
Figure 29H:
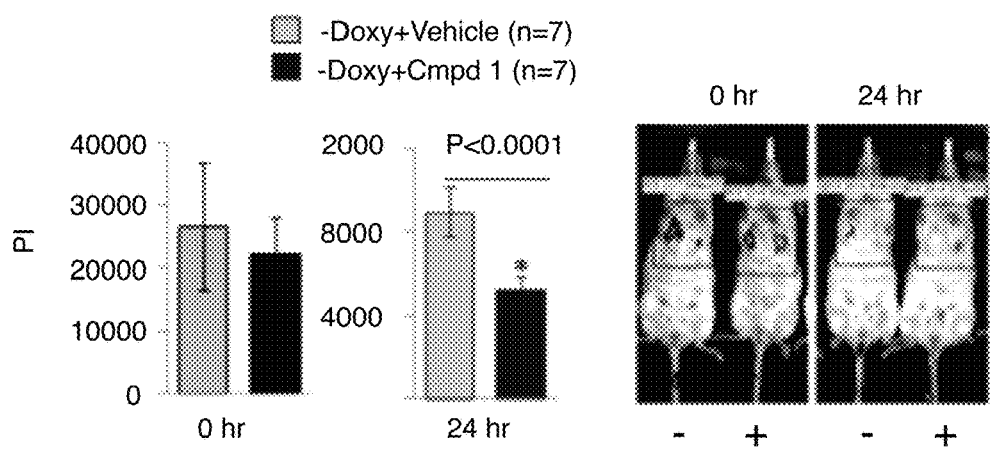
Figure 29I:
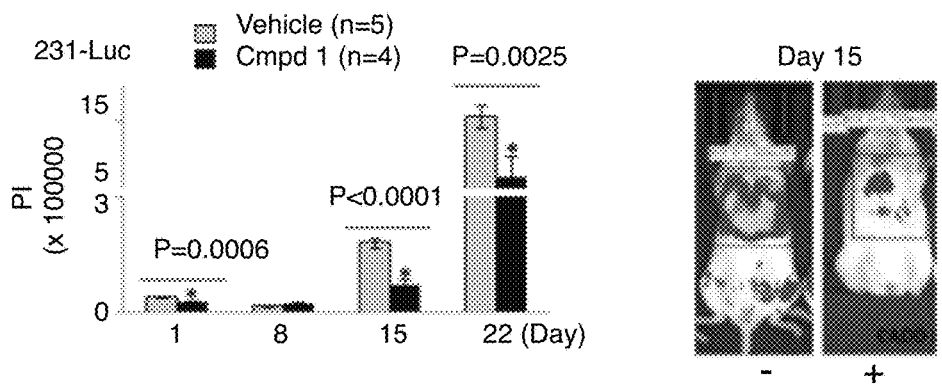

Bioluminescence Imaging (BLI) analysis is useful for sensitive in vivo tumor detection and quantification, and permits earlier detection of tumor growth and metastasis. To further examine the effects of compound 1 on the metastasis of breast cancer, BLI analysis was performed using BC cell lines stably expressing firefly luciferase (MCF7-tet-off-Luc (−Doxy) and 231-Luc) after intravenous delivery of cells into NSG mice. MCF7-tet-off-Luc (−Doxy) cells express RUNX2 when the cells are maintained without Doxycycline (Doxy). compound 1 had no influence on metastatic homing of the MCF7-tet-off-Luc (−Doxy) cells to the mouse lungs (FIG. 29H, left) but significantly reduced the lung retention of the cells (FIG. 29H, right). As the MCF7-tet-off-Luc (−Doxy) cells did not form stable tumors in the lungs of NSG mice (data not shown), we injected 231-Luc cells in the tail vein of mice and repeated the BLI analysis. Colonization and outgrowth of the 231-Luc cells were significantly lower in the compound 1-treated groups than in the vehicle-treated groups (FIG. 29I), indicating that compound 1 inhibits experimental metastasis of BC cells in vivo. Doses of compound 1 up to 20 mg/kg in MMTV-PyMT mice (FIG. 28B), and 10 mg/kg of compound 1 in the nude (FIG. 28D) and NSG mice (FIG. 28E) did not significantly decrease body weight or influence the general health of animals.

EXAMPLE 11

Combination Compound 1 and CDK Inhibitors Therapy

Figure 30A:
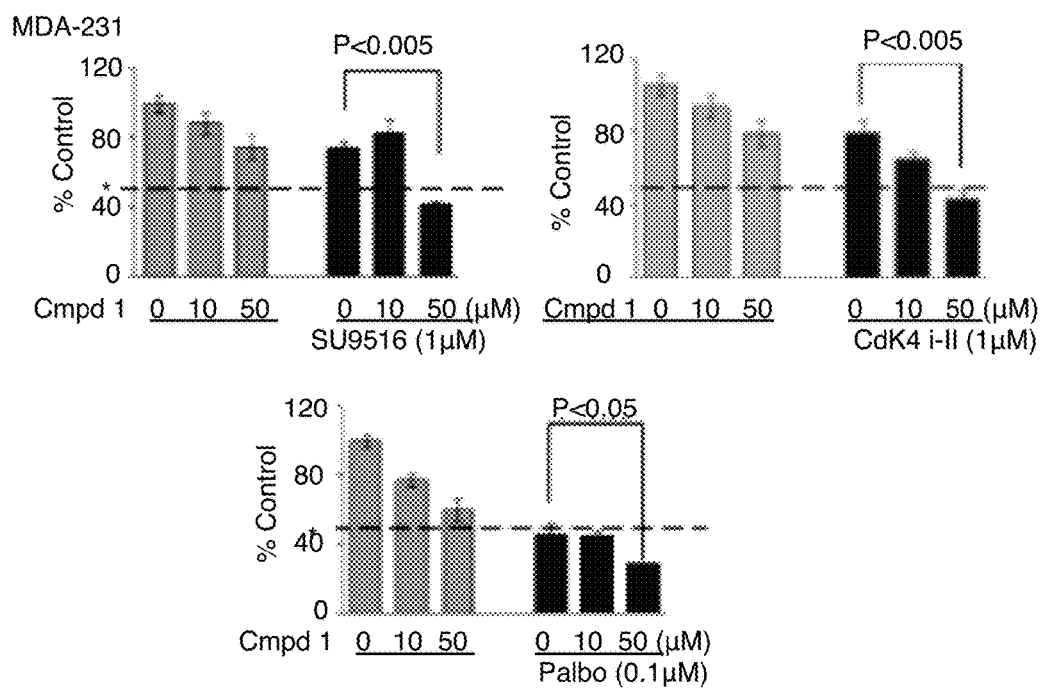
FIGS. 30A-30B show that the combination of compound 1 and CDK inhibitors and BC growth.

MDA-231 cells, which are modestly resistant to compound 1, were treated with compound 1 and the combination of a CDK2 inhibitor (SU99516), CDK4 inhibitor NSC625987 (Cdk4.I-II) or the CDK4/6 inhibitor Paloma/palbociclib (FIG. 30A). Each CDK inhibitor increased compound 1 inhibitory activity and reduced cell proliferation by more than 50% relative to compound 1 alone. Lower doses of Palbociclib and compound 1 were also superior at reducing clonogenic growth of MDA-231 (TNBC) and MCF7

Figure 30B:
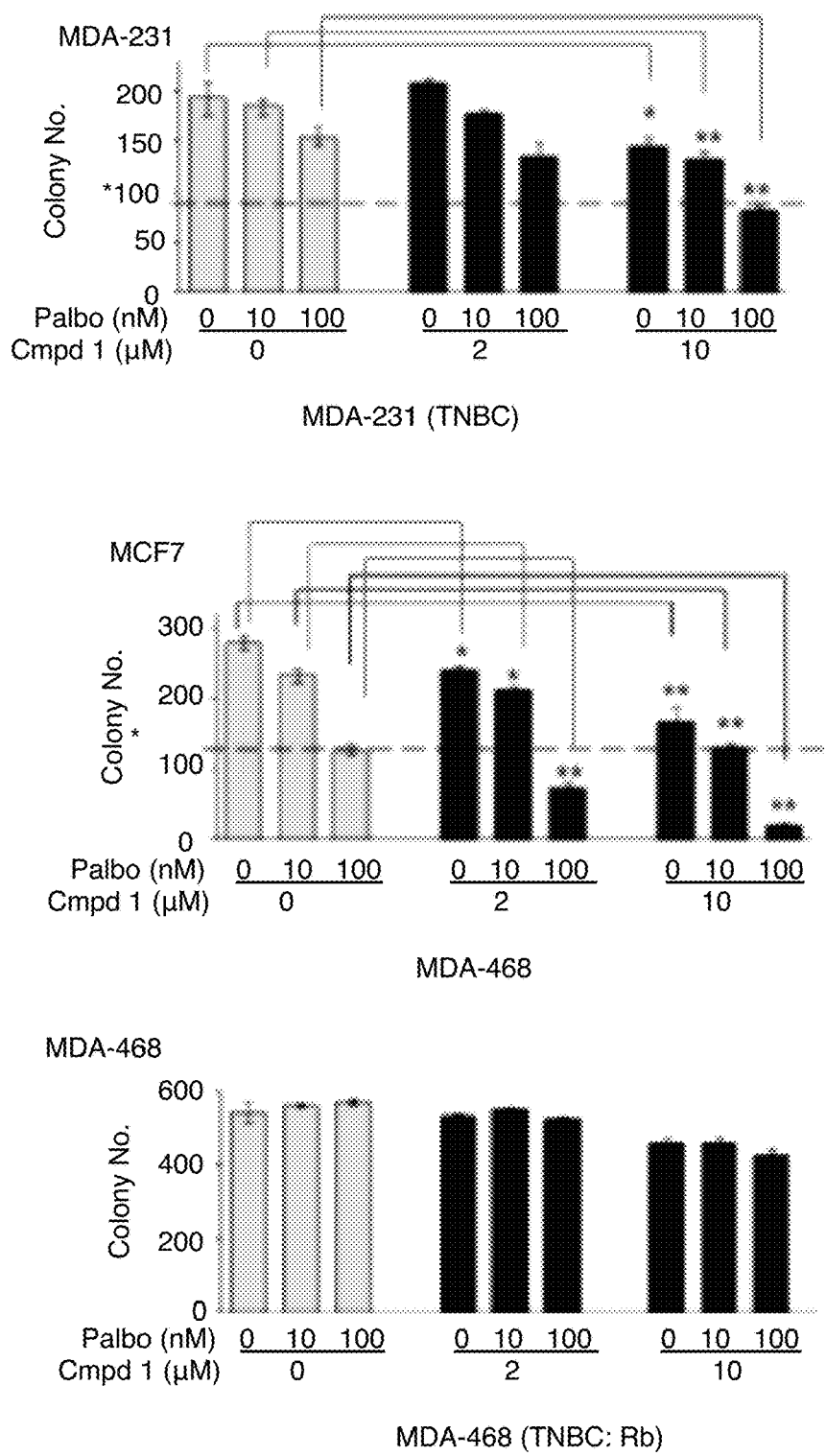

(ER+) but not the MDA-468 TNBC cells, which harbor a retinoblastoma gene mutation (Rb−) (FIG. 30B). There was significant growth inhibition at 10 μM compound 1 for MDA-231 or 2-10 μM compound 1 for MCF7 (ER+) cells, which were also more sensitive than MDA-231 cells to single agent compound 1 treatment.

Interestingly, MDA-468 (TNBC) cells, although very sensitive to compound 1, were resistant to CDK inhibition (FIG. 30B), perhaps because these cells have a mutation in the Rb gene63. However, other TNBC (MDA-231) were sensitive to combination CDK and RUNX2 inhibition. HER2+BT474 cell response was examined and these cells are sensitive to compound 1-mediated growth inhibition as well as Palbociclib (0.1 μM) but no increased sensitivity to combination drugs was observed (data not shown). It is well-known that BC tumors develop resistance even to targeted therapies such as CDK inhibitors. RUNX2 targeting may be effective even for tumors that have lost their sensitivity to CDK inhibitors. Some limitations include the dose profile for compound 1 in live cells (2-50 μM).

Combination Therapy with Compound 1 Analogs

To determine which compounds to choose for in vivo combination chemotherapy with CDK inhibitors, a BC cell panel of ER+ BC (MCF7; T47D) or TNBC (MDA231; Hs578t; HCC70) (Table 2) and CDK inhibitors at defined doses: CDK2i (0.1-10 μM; 24-72 hr) or CDK4i (0.1-10 μM; 24-48 hr) or CDK4/6i Palbociclib or Trilaciclib (0.01-1.0 μM; 24-48 hr) are used. Proliferation (24-96 hr), viability (24-96 hr; Luciferase label), cell death (24-96 hr; caspase or PARP cleavage), clonogenic assays (7-14 days), and metastatic potential (invasion; 6-24 hr) are measured. MCF7 and T47D cells are used to test the effect of RUNX2 (wild-type; mutant) overexpression on GLUT1. MDA-MB-231, Hs578t, and MDA-MB-468 cells are used for RUNX2 gene knockdown approaches. MDA-MB-231 also are used for lung metastasis assays.

TABLE 2

Clinically relevant cell lines for testing combination therapy

| BC Type: | Luminal | | TNBC | HER2+ |
|---|---|---|---|---|
| | ER+ | ER+ | ER− | |
| | RUNX2$^{Low}$ | RUNX2+ | RUNX2++ | RUNX2+/− |
| Cells: | MCF7 | HCC1428 | MDA-MB-231 | BT474 (ER+) |
| | T47D | | MDA-MB-468 | SkBr3 (ERneg) |
| | | | Hs578t; | MDA-MB-361 |
| | | | HCC1937 | (ER+) |
| | | | HCC70; BT20; | |
| | | | BT549 | |

Specific single doses of the CDKi are tested in combination with compound 1 or analog compound dose responses. If the IC50 of a particular compound=x, 0, 0.25×, 0.5×, 1×, 2.5×, 5× dose increments are chosen for combination treatments. Quantitative measurements of cell number over time for each compound analog dose are determined in triplicate±SD and p-values<0.05 are considered significant. Data analysis considers synergistic versus additive or antagonistic criteria The CompuSyn program evaluates drug response in translational studies using these criteria. p.RUNX2, CBFβ levels, and pRb are monitored to confirm that drug treatments alter RUNX2 activity and pRb phosphorylation, which is a substrate of CDK4/6 kinases.

CDK4/6 inhibitors Palbociclib or Trilaciclib (G1T28) are administered to athymic nude mice bearing BC PDX tumors by oral gavage (25-200 mg/kg formulated in vehicle, 2×/wk). Compound 1 and compound analogs 2-10 (1-20 mg/kg, 5×/wk, i.p.) selected from cell culture experiments also are administered for treatment. The University of Maryland collection (UMD-PDX) currently consists of three TNBC (Br-001, Br-002, Br-003) and one ER+/PR+/HER2+ specimen (Br-004, luminal B) banked from tumors grown in mammary fat pads of NSG mice. Five Huntsman Cancer Institute tumors (HCl-PDX) consist of: HCl-001 (TNBC basal-like), HCl-003 (luminal B, ER+, HER2neg), HCl-004 (TNBC basal-like), HCl-008 (basal-like, HER2+), HCl-009 (TNBC) and are maintained at the University of Maryland. The Champions Oncology (CO-PDX) samples are from a collection of eleven TNBC, five HER2+, and three ER+ available tumors (Champions Oncology; Baltimore, Md.). These different PDX experiments are used to examine if compound 1 analogs are predictive of clinical response. CADD compounds (2-10 mg/kg) will be administered i.p. 3-5 times weekly for up to 8 weeks. Tumors will be monitored by caliper measurements and isolated, weighed, and processed at the end of the experiment for IHC and Western blotting with specific antibodies (Ki67, RUNX2, p.RUNX2, GLUT1 (membrane, intracellular)5, MMP13, cleaved caspase-3 (Cell Signaling; #9661), and pRb (CDK biomarker)). As observed for both PDX and PyMT models, proliferative index (Ki67 expression) and RUNX2 levels in vivo, will evaluate drug efficacy.

ER+ BC cells overexpressing RUNX2 (MCF7.RUNX2, T47D.RUNX2) are more invasive than cells expressing low levels of RUNX2. Therefore, these ER+ and the TNBC expressing RUNX2 (MDA-231, Hs578t, HCC70) are useful to examine the effects of drug combinations on in vitro invasion with chambers or the continuously monitored xCELLigence system (Acea Biosciences, Inc). Dosing profiles are as for proliferation assays. Selected compounds from compounds 1-10 combined with Palbociclib or Trilaciclib are tested in the PyMT-GEM model of BC, which allows assessment of spontaneous ER+ BC tumor growth and lung metastasis. As defined for PDX tumors, the ability of the combination treatments to inhibit MDA-231 (TNBC) and MCF7.RUNX2 (ER+) lung metastatic potential (Luciferase-labeled cells) is quantified via tail-vein experimental metastasis assays. Since Palbociclib (CDK4/6 inhibitor) is indicated clinically for ER+ tumors, the ER+ metastatic model provides an accurate baseline for the efficacy of combination CDK and RUNX2 targeted treatments relative to TNBC cells.

The following references were cited herein.
1. Eroles et al., Cancer Treat Rev 2012; 38:698-707.
2. Cadoo et al., Q J Nucl Med Mol Imaging 2013; 57:312-321.
3. Siegel et al., 2013. CA Cancer J Clin 2013; 63:11-30.
4. Foley et al., Semin Cell Dev Biol 2010; 21:951-960.
5. Ganapathy et al., Clin Exp Metastasis 2012; 29: 493-509.
6. Ithimakin et al., Cancer Res 2013; 73:1635-1646.
7. Ferrari et al., J Cell Physiol 2013; 228:1137-1142.
8. McDonald et al., Dis Model Mech 2014.
9. Das et al., Eur J Cancer 2009; 45:2239-2248.
10. Onodera et al., Cancer Sci 2010; 101:2670-2675.
11. Barnes et al., Cancer Res 2004; 64:4506-4513.
12. Pratap et al., Mol Cell Biol 2005; 25:8581-8591.
13. Pratap et al., Cancer Metastasis Rev 2006; 25:589-600.
14. Yagi et al., Embo J 1999; 18:2551-2562.
15. Cui et al., Mol Cell Biol 2003; 23:1004-1013.
16. Vitolo et al., Cancer Biol Ther 2007; 6:856-863.
17. Varelas et al., Nat Cell Biol 2008; 10:837-848.
18. Cordenonsi et al., Cell 2011; 147:759-772.
19. Hiemer et al., J Biol Chem 2014; March 27.
20. Kim J et al., Proc Natl Acad Sci USA 2012; 109:6124-6129.

21. Liu et al., Int J Biochem Mol Biol 2011; 2:247-256.
22. Chan et al., Cancer Res 2008; 68:2592-2598.
23. Lei et al., Mol Cell Biol 2008; 28:2426-2436.
24. Matteucci et al., Eur J Cancer 2013; 49:231-244.
25. Lee et al., J Cell Biol 2006; 172:973-981.
26. Thiery et al., Cell 2009; 139:871-890.
27. Valastyan et al., Cell 2011; 147: 275-292.
28. Hollestelle et al., Breast Cancer Res Treat 2013; 138: 47-57.
29. David et al., Cancer Res 2012; 72:2917-2923.
30. Grabowska et al., Front Biosci (Landmark Ed) 2012; 17:1948-1964.
31. Chunthapong et al., J Cell Biochem 2004; 91 649-661.
32. Inge et al., Exp Cell Res 2011; 317:838-848.
33. Kuefer et al., Clin Cancer Res 2003; 9:6447-6452.
34. Najy et al., J Biol Chem 2008; 283:18393-18401.
35. Brouxhon et al., Clin Cancer Res 2013; 19:3234-3246.
36. Brouxhon et al., Mol Carcinog 2013.
37. Hofmann et al., Clin Biochem 2013; 46:1585-1589.
38. Kuefer et al., Br J Cancer 2005; 92:2018-2023.
39. Turner et al., Semin Cancer Biol 2012; 22:374-378.
40. Underwood et al., J Vis Exp 2013; Issue 78.
41. Qiao et al., J Biol Chem 2006; 281:7118-7128.
42. Rajgopal et al., J Cell Biochem 2007; 100:1509-1517.
43. Chimge et al., Breast Cancer Res 2011; 13:R127.
44. St. Croix et al., J Cell Biol 1998; 142:557-571.
45. Nahta et al., Nat Clin Pract Oncol 2006; 3:269-280.
46. Berman et al., Cancer Prev Res (Phila) 2010; 3:579-587.
47. Chimge et al., Clin Cancer Res 2012; 18:901-911.
48. Chimge et al., Oncogene 2013; 32:2121-2130.
49. Yeh et al., Curr Opin Oncol 2013; 25:652-658.
50. Underwood et al., J Bone Min Res 2012; 27:913-925.
51. Frangou et al., Oncotarget 2014; 5: 2166-12176.
52. Onder et al., Cancer Res 2008; 68:3645-3654.
53. Choe et al., J Cell Biochem. 2015; 116: 2210-2226.

In the foregoing specification the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for treating breast cancer in a subject, comprising:
   administering to the subject a dose of one or more compounds having the chemical structure

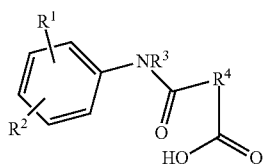

wherein
   $R_1$ and $R_2$ independently are H, Cl, F, Br, $CH_3$, $CF_3$, SH, $-N(C_{1-3}alkyl)_2$, $-NHC(O)C_{1-3}alkyl$, or $-NHC(O)C_{5-7}cycloalkyl$;
   $R_3$ is H or $C_{1-3}$ alkyl; and
   $R_4$ is

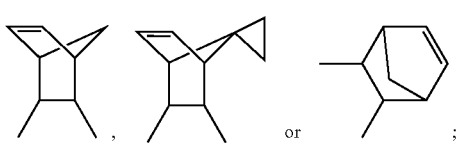

or a pharmaceutically acceptable salt thereof effective to inhibit a RUNX2 activity, thereby treating the breast cancer.

2. The method of claim 1, further comprising administering one or more other cancer drugs.

3. The method of claim 2, wherein the other cancer drugs are Herceptin, Lapatinib, or E-Cadherin monoclonal antibody (DECMA1) antibody.

4. The method of claim 1, wherein the breast cancer is a metastatic cancer.

5. A method for treating a metastatic cancer originating from a breast cancer in a subject, comprising:
   administering to the subject a dose of one or more compounds having the chemical structure

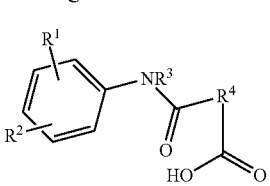

wherein
   $R_1$ and $R_2$ independently are H, Cl, F, Br, $CH_3$, $CF_3$, SH, $-N(C_{1-3}alkyl)_2$, $-NHC(O)C_{1-3}alkyl$, or $-NHC(O)C_{5-7}cycloalkyl$;
   $R_3$ is H or $C_{1-3}$ alkyl; and
   $R_4$ is

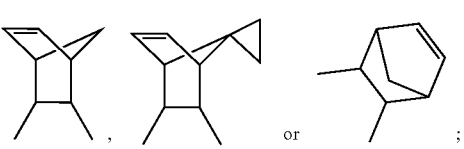

or a pharmaceutically acceptable salt thereof effective to inhibit a RUNX2 activity, thereby treating the metastatic cancer.

6. The method of claim 5, further comprising administering one or more other cancer drugs.

7. The method of claim 6, wherein the other cancer drugs are Herceptin, Lapatinib, or E-Cadherin monoclonal antibody (DECMA1).

8. A method for treating breast cancer in a subject, comprising
   administering to the subject a dose of a compound having the chemical structure:

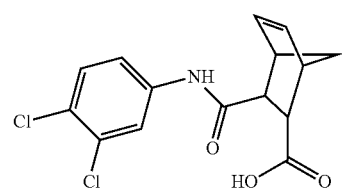 [SMILES: O=C(O)C1C2C=CC(C2)C1C(=O)Nc1ccc(Cl)c(Cl)c1]

or a pharmaceutically acceptable salt thereof effective to inhibit RUNX2, thereby treating the breast cancer.

9. The method of claim 8, further comprising administering one or more other cancer drugs.

10. The method of claim 9, wherein the other cancer drugs are Herceptin, Lapatinib, or E-Cadherin monoclonal antibody (DECMA1).

11. The method of claim 8, wherein the breast cancer comprises metastases thereof.

12. The method of claim 8, wherein treatment inhibits metastasis of the breast cancer.

13. The method of claim 1, wherein $R_3$ is H.

14. The method of claim 1, wherein $R_1$ and $R_2$ are independently H, Cl, Br, or $-NHC(O)CH_3$, $R_3$ is H and $R_4$ is

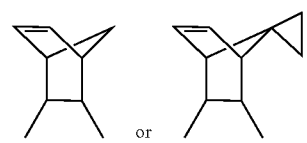

15. The method of claim 1, wherein $R_1$ and $R_2$ are independently H, Cl, $CH_3$, $-NHC(O)CH_3$, $-NHC(O)$cyclohexane, or $N(CH_3)_2$, $R_3$ is H and $R_4$ is

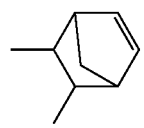

16. The method of claim 1, wherein $R_1$ and $R_2$ are each Cl and $R_3$ is H.

17. The method of claim 1, wherein the chemical structure is:

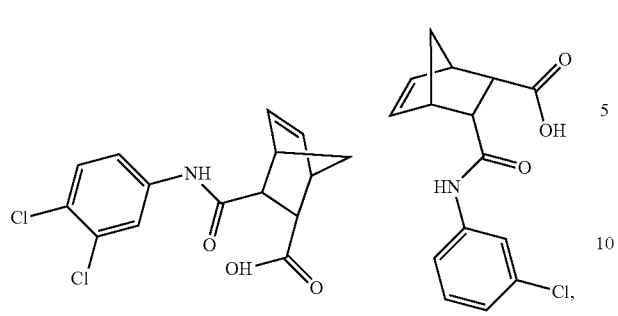
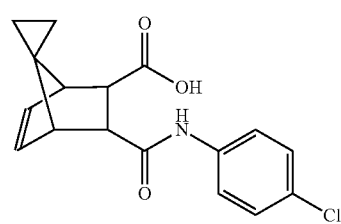
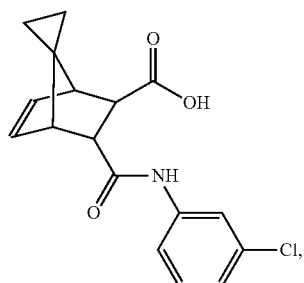
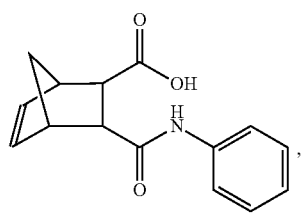
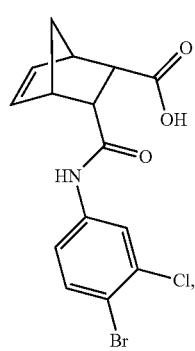
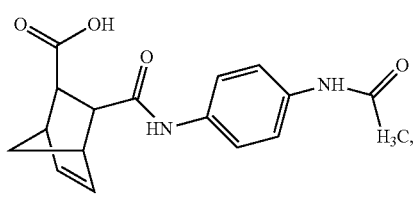
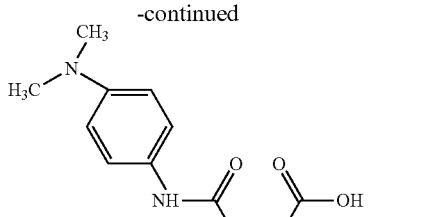
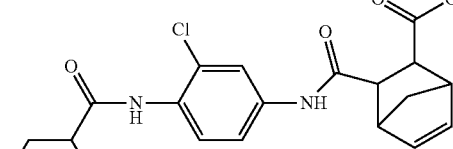
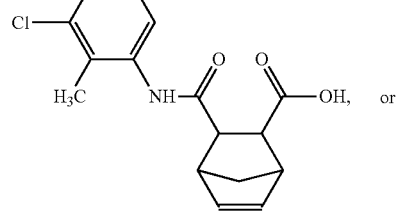
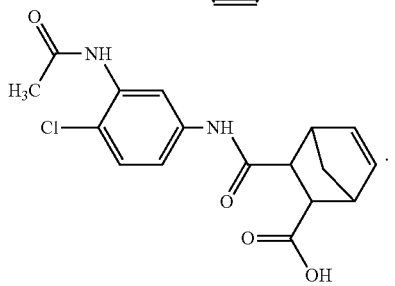
18. The method of claim 5, wherein $R_3$ is H.
19. The method of claim 5, wherein $R_1$ and $R_2$ are independently H, Cl, Br, or —NHC(O)CH$_3$, $R_3$ is H and $R_4$ is
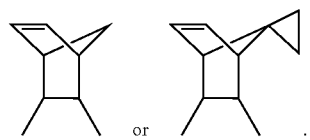
20. The method of claim 5, wherein $R_1$ and $R_2$ are independently H, Cl, CH$_3$, —NHC(O)CH$_3$, —NHC(O)cyclohexane, or N(CH$_3$)$_2$, $R_3$ is H and $R_4$ is
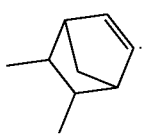
21. The method of claim 5, wherein $R_1$ and $R_2$ are each Cl and $R_3$ is H.

22. The method of claim 5, wherein the chemical structure is:
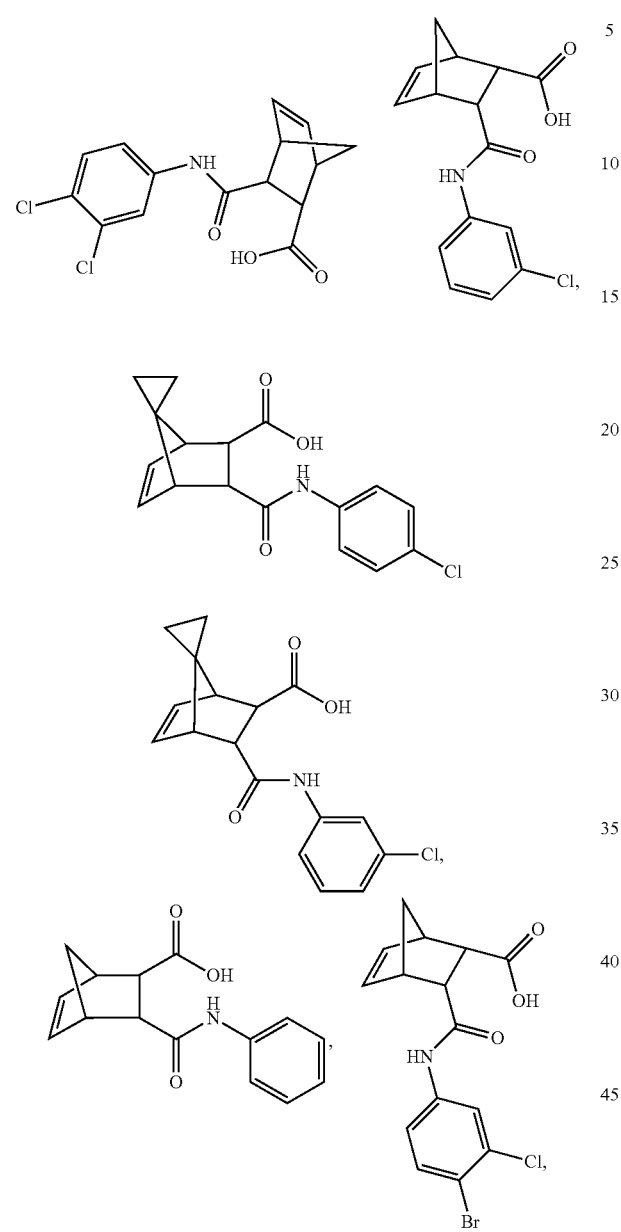
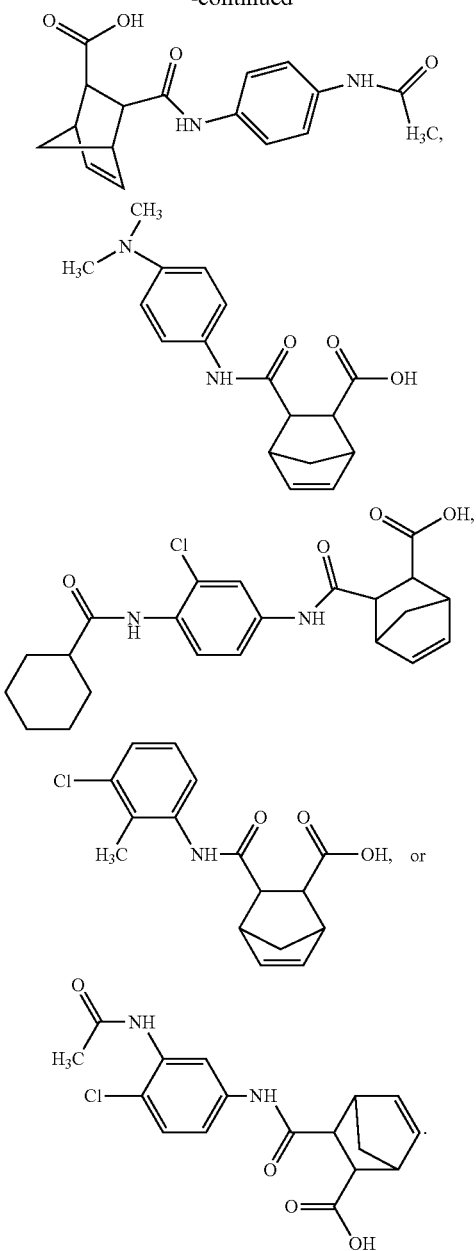
* * * * *

SEQUENCE LISTING

<160> NUMBER OF SEQ ID NOS: 35

<210> SEQ ID NO 1
<211> LENGTH: 21
<212> TYPE: RNA
<213> ORGANISM: Artificial Sequence
<220> FEATURE:
<223> OTHER INFORMATION: TAZ siRNA sequence

<400> SEQUENCE: 1
gacaugagau ccaucacuau u                                              21

<210> SEQ ID NO 2
<211> LENGTH: 21
<212> TYPE: RNA
<213> ORGANISM: Artificial Sequence
<220> FEATURE:
<223> OTHER INFORMATION: TAZ siRNA sequence

<400> SEQUENCE: 2
ggacaaacac ccaugaacau u                                              21

<210> SEQ ID NO 3
<211> LENGTH: 21
<212> TYPE: RNA
<213> ORGANISM: Artificial Sequence
<220> FEATURE:
<223> OTHER INFORMATION: TAZ siRNA sequence

<400> SEQUENCE: 3
aagccuagcu cguggcggau u                                              21

<210> SEQ ID NO 4
<211> LENGTH: 63
<212> TYPE: DNA
<213> ORGANISM: Artificial Sequence
<220> FEATURE:
<223> OTHER INFORMATION: Forward primer for human osteocalcin and MMP13
      oligonucleotides

<400> SEQUENCE: 4
ttctaccaca aaccacactc gttctaccac aaaccacact cgttctacca              50
caaaccacac tcg                                                      63

<210> SEQ ID NO 5
<211> LENGTH: 63
<212> TYPE: DNA
<213> ORGANISM: Artificial Sequence
<220> FEATURE:
<223> OTHER INFORMATION: Reverse primer for human osteocalcin and MMP13
      oligonucleotides

<400> SEQUENCE: 5
cgagtgtggt ttgtggtaga acgagtgtgg tttgtggtag aacgagtgtg            50
gtttgtggta gaa                                                    63

<210> SEQ ID NO 6
<211> LENGTH: 20
<212> TYPE: DNA
<213> ORGANISM: Artificial Sequence
<220> FEATURE:
<223> OTHER INFORMATION: Forward primer for MMP13 proximal promoter
      region

<400> SEQUENCE: 6
ggttttgaga ccctgctgaa                                             20

<210> SEQ ID NO 7
<211> LENGTH: 20
<212> TYPE: DNA
<213> ORGANISM: Artificial Sequence
<220> FEATURE:
<223> OTHER INFORMATION: Reverse primer for MMP13 proximal promoter
      region

<400> SEQUENCE: 7
cgtggcgact ttttcttttc                                             20

<210> SEQ ID NO 8
<211> LENGTH: 24
<212> TYPE: DNA
<213> ORGANISM: Artificial Sequence
<220> FEATURE:
<223> OTHER INFORMATION: Forward primer for RUNX1 gene

<400> SEQUENCE: 8
tgtcggtcga agtggaagag ggaa                                        24

<210> SEQ ID NO 9
<211> LENGTH: 20
<212> TYPE: DNA
<213> ORGANISM: Artificial Sequence
<220> FEATURE:
<223> OTHER INFORMATION: Reverse primer for RUNX1 gene

<400> SEQUENCE: 9
agctcccggg cttggtctga                                             20

<210> SEQ ID NO 10
<211> LENGTH: 19
<212> TYPE: DNA
<213> ORGANISM: Artificial Sequence
<220> FEATURE:
<223> OTHER INFORMATION: Forward primer for RUNX2 gene

<400> SEQUENCE: 10
tgcctgcctg gggtctgta                                              19

```
<210> SEQ ID NO 11
<211> LENGTH: 19
<212> TYPE: DNA
<213> ORGANISM: Artificial Sequence
<220> FEATURE:
<223> OTHER INFORMATION: Reverse primer for RUNX2 gene

<400> SEQUENCE: 11
cgggccctcc ctgaactct                                           19

<210> SEQ ID NO 12
<211> LENGTH: 18
<212> TYPE: DNA
<213> ORGANISM: Artificial Sequence
<220> FEATURE:
<223> OTHER INFORMATION: Forward primer for VEGF gene

<400> SEQUENCE: 12
cttgccttgc tgctctac                                            18

<210> SEQ ID NO 13
<211> LENGTH: 19
<212> TYPE: DNA
<213> ORGANISM: Artificial Sequence
<220> FEATURE:
<223> OTHER INFORMATION: Reverse primer for VEGF gene

<400> SEQUENCE: 13
tggcttgaag atgtactcg                                           19

<210> SEQ ID NO 14
<211> LENGTH: 20
<212> TYPE: DNA
<213> ORGANISM: Artificial Sequence
<220> FEATURE:
<223> OTHER INFORMATION: Forward primer for Glut-1 gene

<400> SEQUENCE: 14
cgggccaaga gtgtgctaaa                                          20

<210> SEQ ID NO 15
<211> LENGTH: 20
<212> TYPE: DNA
<213> ORGANISM: Artificial Sequence
<220> FEATURE:
<223> OTHER INFORMATION: Reverse primer for Glut-1 gene

<400> SEQUENCE: 15
tgacgatacc ggagccaatg                                          20

<210> SEQ ID NO 16
<211> LENGTH: 20
<212> TYPE: DNA
<213> ORGANISM: Artificial Sequence
<220> FEATURE:
<223> OTHER INFORMATION: Forward primer for LDHA gene

<400> SEQUENCE: 16
attcagcccg attccgttac                                          20

<210> SEQ ID NO 17
<211> LENGTH: 21
<212> TYPE: DNA
<213> ORGANISM: Artificial Sequence
<220> FEATURE:
<223> OTHER INFORMATION: Reverse primer for LDHA gene
```

```
<400> SEQUENCE: 17
gacaccagca acattcattc c                                              21

<210> SEQ ID NO 18
<211> LENGTH: 24
<212> TYPE: DNA
<213> ORGANISM: Artificial Sequence
<220> FEATURE:
<223> OTHER INFORMATION: Forward primer for SIRT6 gene

<400> SEQUENCE: 18
aagttcgaca ccacctttga gagc                                           24

<210> SEQ ID NO 19
<211> LENGTH: 24
<212> TYPE: DNA
<213> ORGANISM: Artificial Sequence
<220> FEATURE:
<223> OTHER INFORMATION: Reverse primer for SIRT6 gene

<400> SEQUENCE: 19
acgtactgcg tcttacactt ggca                                           24

<210> SEQ ID NO 20
<211> LENGTH: 21
<212> TYPE: DNA
<213> ORGANISM: Artificial Sequence
<220> FEATURE:
<223> OTHER INFORMATION: Forward primer for MT1-MMP gene

<400> SEQUENCE: 20
ctaagacctt gggaggaaaa c                                              21

<210> SEQ ID NO 21
<211> LENGTH: 21
<212> TYPE: DNA
<213> ORGANISM: Artificial Sequence
<220> FEATURE:
<223> OTHER INFORMATION: Reverse primer for MT1-MMP gene

<400> SEQUENCE: 21
aagccccatc caaggctaac a                                              21

<210> SEQ ID NO 22
<211> LENGTH: 21
<212> TYPE: DNA
<213> ORGANISM: Artificial Sequence
<220> FEATURE:
<223> OTHER INFORMATION: Forward primer for MMP2 gene

<400> SEQUENCE: 22
cttcttcaag gaccggttca t                                              21

<210> SEQ ID NO 23
<211> LENGTH: 21
<212> TYPE: DNA
<213> ORGANISM: Artificial Sequence
<220> FEATURE:
<223> OTHER INFORMATION: Reverse primer for MMP2 gene

<400> SEQUENCE: 23
gctggctgag tagatccagt a                                              21

<210> SEQ ID NO 24
<211> LENGTH: 20
```

```
<212> TYPE: DNA
<213> ORGANISM: Artificial Sequence
<220> FEATURE:
<223> OTHER INFORMATION: Forward primer for MMP9 gene

<400> SEQUENCE: 24
gggacgcaga catcgtcatc                                                  20

<210> SEQ ID NO 25
<211> LENGTH: 20
<212> TYPE: DNA
<213> ORGANISM: Artificial Sequence
<220> FEATURE:
<223> OTHER INFORMATION: Reverse primer for MMP9 gene

<400> SEQUENCE: 25
tcgtcatcgt cgaaatgggc                                                  20

<210> SEQ ID NO 26
<211> LENGTH: 20
<212> TYPE: DNA
<213> ORGANISM: Artificial Sequence
<220> FEATURE:
<223> OTHER INFORMATION: Forward primer for MMP13 gene

<400> SEQUENCE: 26
taaccgtatt gttcgcgtca                                                  20

<210> SEQ ID NO 27
<211> LENGTH: 20
<212> TYPE: DNA
<213> ORGANISM: Artificial Sequence
<220> FEATURE:
<223> OTHER INFORMATION: Reverse primer for MMP13 gene

<400> SEQUENCE: 27
tccagccacg catagtcata                                                  20

<210> SEQ ID NO 28
<211> LENGTH: 21
<212> TYPE: DNA
<213> ORGANISM: Artificial Sequence
<220> FEATURE:
<223> OTHER INFORMATION: Forward primer for BSF gene

<400> SEQUENCE: 28
aaagtgagaa cggggaacct r                                                21

<210> SEQ ID NO 29
<211> LENGTH: 20
<212> TYPE: DNA
<213> ORGANISM: Artificial Sequence
<220> FEATURE:
<223> OTHER INFORMATION: Reverse primer for BSF gene

<400> SEQUENCE: 29
gatgcaaagc cagaatggat                                                  20

<210> SEQ ID NO 30
<211> LENGTH: 18
<212> TYPE: DNA
<213> ORGANISM: Artificial Sequence
<220> FEATURE:
<223> OTHER INFORMATION: Forward primer for OC gene

<400> SEQUENCE: 30
```

```
acactcctcg ccctattg                                                 18

<210> SEQ ID NO 31
<211> LENGTH: 18
<212> TYPE: DNA
<213> ORGANISM: Artificial Sequence
<220> FEATURE:
<223> OTHER INFORMATION: Reverse primer for OC gene

<400> SEQUENCE: 31
gatgtggtca gccaactc                                                 18

<210> SEQ ID NO 32
<211> LENGTH: 20
<212> TYPE: DNA
<213> ORGANISM: Artificial Sequence
<220> FEATURE:
<223> OTHER INFORMATION: Forward primer for OPN gene

<400> SEQUENCE: 32
ttgcagtgat ttgcttttgc                                               20

<210> SEQ ID NO 33
<211> LENGTH: 20
<212> TYPE: DNA
<213> ORGANISM: Artificial Sequence
<220> FEATURE:
<223> OTHER INFORMATION: Reverse primer for OPN gene

<400> SEQUENCE: 33
gtcatggctt tcgttggact                                               20

<210> SEQ ID NO 34
<211> LENGTH: 24
<212> TYPE: DNA
<213> ORGANISM: Artificial Sequence
<220> FEATURE:
<223> OTHER INFORMATION: Forward primer for beta-actin gene

<400> SEQUENCE: 34
tggcaccaca cctctacaat gagc                                          24

<210> SEQ ID NO 35
<211> LENGTH: 25
<212> TYPE: DNA
<213> ORGANISM: Artificial Sequence
<220> FEATURE:
<223> OTHER INFORMATION: Reverse primer for beta-actin gene

<400> SEQUENCE: 35
gcacagcttc tccttaatgt cacgc                                         25
```